(12) United States Patent
Donson et al.

(10) Patent No.: US 6,448,046 B1
(45) Date of Patent: *Sep. 10, 2002

(54) RECOMBINANT ANIMAL VIRAL NUCLEIC ACIDS

(75) Inventors: Jon Donson, Davis, CA (US); William O. Dawson, Winter Haven, FL (US); George L. Grantham, Riverside, CA (US); Thomas H. Turpen, Vacaville, CA (US); Ann M. Turpen, Vacaville, CA (US); Stephen J. Garger, Vacaville, CA (US); Laurence K. Grill, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/726,651

(22) Filed: Nov. 28, 2000

Related U.S. Application Data

(63) Continuation of application No. 08/484,341, filed on Jun. 7, 1995, now Pat. No. 6,054,566, which is a continuation of application No. 08/483,502, filed on Jun. 7, 1995, now Pat. No. 6,284,492, which is a continuation-in-part of application No. 08/184,237, filed on Jan. 19, 1994, which is a continuation-in-part of application No. 07/923,692, filed on Jul. 31, 1992, now Pat. No. 5,316,931, which is a continuation-in-part of application No. 07/600,244, filed on Oct. 22, 1990, now abandoned, and a continuation-in-part of application No. 07/614,617, filed on Jan. 16, 1991, now abandoned, and a continuation-in-part of application No. 07/737,899, filed on Jul. 26, 1991, now abandoned, and a continuation-in-part of application No. 07/739,143, filed on Aug. 1, 1991, now abandoned, said application No. 07/600,244, is a continuation of application No. 07/310,881, filed on Feb. 17, 1989, now abandoned, which is a continuation-in-part of application No. 07/160,766, filed on Feb. 26, 1988, now abandoned, and a continuation-in-part of application No. 07/160,771, filed on Feb. 26, 1988, now abandoned, said application No. 07/641,617, is a continuation of application No. 07/347,637, filed on May 5, 1989, now abandoned, said application No. 07/737,899, is a continuation of application No. 07/363,138, filed on Jun. 8, 1989, now abandoned, which is a continuation-in-part of application No. 07/219,279, filed on Jul. 15, 1988, now abandoned.

(51) Int. Cl.[7] ............... C12N 15/11; C12N 15/09; C12P 21/00

(52) U.S. Cl. ............ 435/70.1; 435/69.1; 435/455; 435/456; 435/325; 435/235.1; 435/320.1; 536/23.1; 536/24.1

(58) Field of Search ............... 435/70.1, 69.1, 435/455, 456, 325, 235.1, 320.1, 172.3, 440; 536/23.1, 24.1; 514/44; 800/2; 935/22, 32, 41

(56) References Cited

U.S. PATENT DOCUMENTS 6,284,492 B1 * 9/2001 Donson et al. ............ 435/70.1

* cited by examiner

*Primary Examiner*—Michael C. Wilson
(74) *Attorney, Agent, or Firm*—Albert P. Halluin; Thomas Gallegos; Viola T. Kung

(57) ABSTRACT

The present invention relates to a recombinant viral nucleic acid selected from a (+) sense, single stranded RNA virus possessing a native subgenomic promoter encoding for a first viral subgenomic promoter, a nucleic acid sequence that codes for a viral coat protein whose transcription is regulated by the first viral subgenomic promoter, a second viral subgenomic promoter and a second nucleic acid sequence whose transcription is regulated by the second viral subgenomic promoter. The first and second viral subgenomic promoters of the recombinant viral nucleic acid do not have homologous sequences relative to each other. The recombinant viral nucleic acid provides the particular advantage that it systemically transcribes the second nucleic acid in the host. Host organisms encompassed by the present invention include procaryotes and eucaryotes, particularly animals and plants. The present invention also relates to viruses containing the viral vectors which are infective, production cells which are capable of producing the viruses or parts thereof, a host infected by the viruses of the invention, the gene products produced by expression of the viral nucleic acids and a process for the production of a desired product by growing the infected hosts.

3 Claims, 8 Drawing Sheets a  b  c       d

SIZE MARKERS

YEAST ENGINEERED
TO PRODUCE TRICOSANTHIN

PURIFIED EXTRACT OF PLANTS THAT HAVE
BEEN INDUCED TO PRODUCE TRICHOSANTHIN
USING THE GENEWARE SYSTEM

← UNPROCESSED TRICHOSANTHIN
← PROCESSED TRICHOSANTHIN

α-trichosanthin

ClaI XhoI
XhoI
XbaI
30K
Ocp
183/54K
TMV RNA (+7492)
KpnI
BamHI pBGC152
(11.2 kb)

126K
pBR322

TMV RNA (+1)

| 126K | 68 nt | SP6 promoter |

RECOMBINANT ANIMAL VIRAL NUCLEIC ACIDS

CROSS-REFERENCE TO RELATED APPLICATIONS

The present application is a continuation of U.S. application Ser. No. 08/483,502, filed Jun. 7, 1995 now U.S. Pat. No. 6,284,492; which is a continuation-in-part of U.S. application Ser. No. 08/184,237, filed Jan. 19, 1994; which is a continuation of application Ser. No. 08/484,341, filed Jun. 7, 1995, now U.S. Pat. No. 6,054,566, which is a continuation-in part of application Ser. No. 07/923,692, filed Jul. 31, 1992. U.S. Pat. No. 5,316,931 Ser. No 07/923,692 is a continuation-in part of applications Ser. No. 07/600,244, filed Oct. 22, 1990, now abandoned, Ser. No. 07/641,617, filed Jan. 16, 1991, now abandoned, Ser. No. 07/737,899 filed Jul. 26, 1991, now abandoned, and Ser. No. 07/739,143, filed Aug. 1, 1991, now abandoned. Ser. No. 07/600,244 is a continuation of application Ser. No. 07/310,881, filed Feb. 17, 1989, now abandoned, which is a continuation-in-part of applications Ser. Nos. 07/160,766 and 07/160,771, both filed on Feb. 26, 1988 and now abandoned. Ser. No. 07/641,617 is a continuation of application Ser. No. 07/347,637, filed May 5, 1989, now abandoned. Ser. No. 07/737,899 is a continuation of application of Ser. No. 07/363,138 filed Jun. 8, 1989, now abandoned, which is a continuation-in-part of application Ser. No. 07/219,279, filed Jul. 15, 1988, now abandoned. The disclosures of each of the foregoing applications is incorporated herein by reference.

BACKGROUND OF THE INVENTION

The present invention relates to viral vectors which are (a) self-replicating; (b) capable of systemic infection in a host; (c) contain, or are capable of containing, nucleic acid sequences foreign to the native virus, which are transcribed or expressed in the host; and (d) stable, especially for the transcription and expression of foreign nucleic acid sequences.

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Unlike cells, viruses do not grow in size and then divide, because they contain within their coats few (or none) of the biosynthetic enzymes and other machinery required for their replication. Rather, viruses multiply in cells by the synthesis of their separate components, followed by assembly. Thus, the viral nucleic acid, after shedding its coat, comes into contact with the appropriate cell machinery where it specifies the synthesis of proteins required for viral reproduction. The viral nucleic acid is then itself replicated through the use of both viral and cellular enzymes. The components of the viral coat are formed and the nucleic acid and coat components are finally assembled. With some viruses, replication is initiated by enzymes present in virions.

Viruses are subdivided into three main classes; animal viruses, plant viruses and bacterial viruses. Within each class, each virus is able to infect only certain species of cells. With animal and bacterial viruses, the host range is determined by the specificity of attachment to the cells which depends on properties of both the virion's coat and specific receptors on the cell surface. These limitations disappear when transfection occurs, i e., when infection is carried out by the naked viral nucleic acid, whose entry does not depend on virus-specific receptors.

A given virus may contain either DNA or RNA, which may be either single- or double-stranded. The portion of nucleic acid in a virion varies from about 1% to about 50%. The amount of genetic information per virion varies from about 3 kb to 300 kb per strand. The diversity of virus-specific proteins varies accordingly. Examples of double-stranded DNA containing viruses include, but are not limited to, Hepatitis 8 virus, papovaviruses such as polyoma and papilloma, adenovirus, poxviruses such as vaccinia, cauli-moviruses such as Cauliflower mosaic virus (CaMV), Pseudomonas phage PMS2, Herpesvirus, *Bacillus subtilin* phage SP8, and the T bacteriophages. Representative viruses which are single-stranded DNA are the parvoviruses and the bacteriophages φX174, f1 and M13. Reoviruses, cytoplasmic polyhedrosis virus of silkworm, rice dwarf virus and wound tumor virus are examples of double-stranded RNA viruses. Single-stranded RNA viruses include tobacco mosaic virus (TMV), turnip yellow mosaic virus (TYMV) picornaviruses, myxoviruses, paramyxoviruses and rhabdoviruses. The RNA in single-stranded RNA viruses may be either a plus or a minus strand. For general information concerning viruses see Grierson, D. et al., *Plant Molecular Biology*, Blackie, London, pp. 126–146 (1984); Gluzman, Y. et al., *Communications in Molecular Biology: Viral Vectors*, Cold Spring Harbor Laboratory, New York, pp. 172–189 (1988).

One means for classifying viruses is based on its genomic organization. Although many viruses have RNA genomes, organization of genetic information differs between groups. For example, the genome of most monopartite plant RNA viruses is a single-stranded molecule of (+)-sense. There are at least 11 major groups of viruses belonging to this genome. An example of this type of virus is TMV. At least six major groups of plant RNA viruses have a bipartite genome. In these, the genome usually consists of two distinct (+)-sense single-stranded RNA molecules encapsidated in separate particles. Both RNAs are required for infectivity. Cowpea mosaic virus (CPMW) is one example of a bipartite plant virus. A third major group, containing at least six major types of plant viruses, is tripartite, with three (+)-sense single-stranded RNA molecules. Each strand is separately encapsidated, and all three are required for infectivity. An example of a tripartite plant virus is alfalfa mosaic virus (AMV). Many plant viruses also have smaller subgenomic mRNAs that are synthesized to amplify a specific gene product. One group of plant viruses having a single-stranded DNA genome are the geminiviruses, such as Cassava latent virus (CLV) and maize streak virus (MSV). Several plant viruses have been cloned to study their nucleic acid, in anticipation of their use as plant transformation vectors. Examples of viruses cloned include BMV, Ahlquist, P. and M. Janda, *Mol. Cell Biol.* 4:2876 (1984); TMV, Dawson W. O. et al. *Proc. Nat. Acad. Sci. USA* 83:1832 (1986); CaMV, Lebeurier, G. et al. *Gene* 12:139 (1980); and BGMV, Morinaga, T. et al. U.S. Pat. No. 4,855,237.

Techniques have been developed which are utilized to transform many species of organisms. Hosts which are capable of being transformed by these techniques include bacteria, yeast, fungus, animal cells and plant cells or tissue. Transformation is accomplished by using a vector which is self-replicating and which is compatible with the desired host. The vectors are generally based on either a plasmid or a virus. Foreign DNA is inserted into the vector, which is then used to transform the appropriate host. The transformed host is then identified by selection or screening. For further information concerning the transformation of these hosts, see Maniatis, T. et al., *Molecular Cloning* (1st Ed.) and Sambrook, J. et al. (2nd Ed.), Cold Spring Harbor Laboratory, Cold Spring Harbor (1982, 1989); *Molecular Cloning*, D. M. Clover, Ed., IRL Press, Oxford (1985); Grierson, D. et al. *Plant Molecular Biology*, Blackie, London, pp. 126–146 (1984), and *Methods in Enzymology*, Vols. 68, 100, 101, 118 and 152–155 (1979, 1983, 1986 and 1987).

Viruses that have been shown to be useful for the transformation of plant hosts include CaV, TMV and BV. Transformation of plants using plant viruses is described in Morinaga, T. et al. U.S. Pat. No. 4,855,237 (BGV), EP-A 67,553 (TMV), Japanese Published Application No. 63-14693 (TMV), EPA 194,809 (BV), EPA 278,667 (BV), Brisson, N. et al., *Methods in Enzymology* 118:659 (1986) (CaV), and Guzman, Y. et al. *Communications in Molecular Biology: Viral Vectors*, Cold Spring Harbor Laboratory, New York, pp. 172–189 (1988). Pseudovirus particles for use in expressing foreign DNA in many hosts, including plants, is described in WO 87/06261.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as by Dawson, W. O. et al., *Virology* 172:286–292 (1989); Takamatsu, N. et al., *EMBO J* 6:307–311 (1987); French, R. et al., *Science* 231:1294–1297 (1986); and Takamatsu, N. et al., *FEBS Letters* 269:73–76 (1990). However, none of these viral vectors have been capable of systemic spread in the plant and expression of the non-viral foreign genes in the majority of the plant cells in the whole plant. Another disadvantage of many of the prior art viral vectors is that they are not stable for the maintenance of non-viral foreign genes. See, for example, Dawson, W. O. et al., *Virology* 172:285–292 (1989). Thus, despite all of this activity to develop viral vectors and viruses, a need still exists for a stable recombinant virus capable of systemic infection in the host and stable expression of the foreign DNA.

SUMMARY OF THE INVENTION

The present invention relates to a recombinant viral nucleic acid selected from a (+) sense, single stranded RNA virus possessing a native subgenomic promoter encoding for a first viral subgenomic promoter, a nucleic acid sequence that codes for a viral coat protein whose transcription is regulated by the first viral subgenomic promoter, a second viral subgenomic promoter and a second nucleic acid sequence whose transcription is regulated by the second viral subgenomic promoter. The first and second viral subgenomic promoters of the recombinant viral nucleic acid do not have homologous sequences relative to each other. The recombinant viral nucleic acid provides the particular advantage that it systemically transcribes the second nucleic acid in the host. Host organisms encompassed by the present invention include procaryotes and eucaryotes, particularly animals and plants.

The present invention also relates to viruses containing the viral vectors which are infective, production cells which are capable of producing the viruses or parts thereof, a host infected by the viruses of the invention, the gene products produced by expression of the viral nucleic acids and a process for the production of a desired product by growing the infected hosts.

BRIEF DESCRIPTION OF THE FIGURES

FIG. 2 is an autoradiograph of a Western analysis of the production of α-trichosanthin in *N. benthamiana* infected in accordance with the present invention. Lane a is molecular size markers, lanes b and c are extracts from yeast engineered to produce α-trichosanthin and lane d is a extract from *N. benthamiana*.

FIGS. 3A and 3B illustrate the α-trichosanthin expression vector, pBGC152. This plasmid contains the TMV-U1 126-, 183-, and 30-kDa open reading frames (ORFs), the ORSV coat protein gene (Ocp), the SP6 promoter, the α-trichosanthin gene, and part of the pBR322 plasmid (SEQ ID NOs: 15 and 16). The TAA stop codon in the 30K ORF is underlined and a bar (|) divides the putative signal peptide from the mature peptide. The TMV-U1 subgenomic promoter located within the minus strand of the 30K ORF controls the expression of α-trichosanthin. The putative transcription start point (tsp) of the subgenomic RNA is indicated with a period(.).

DETAILED DESCRIPTION OF THE INVENTION

Figure 1:
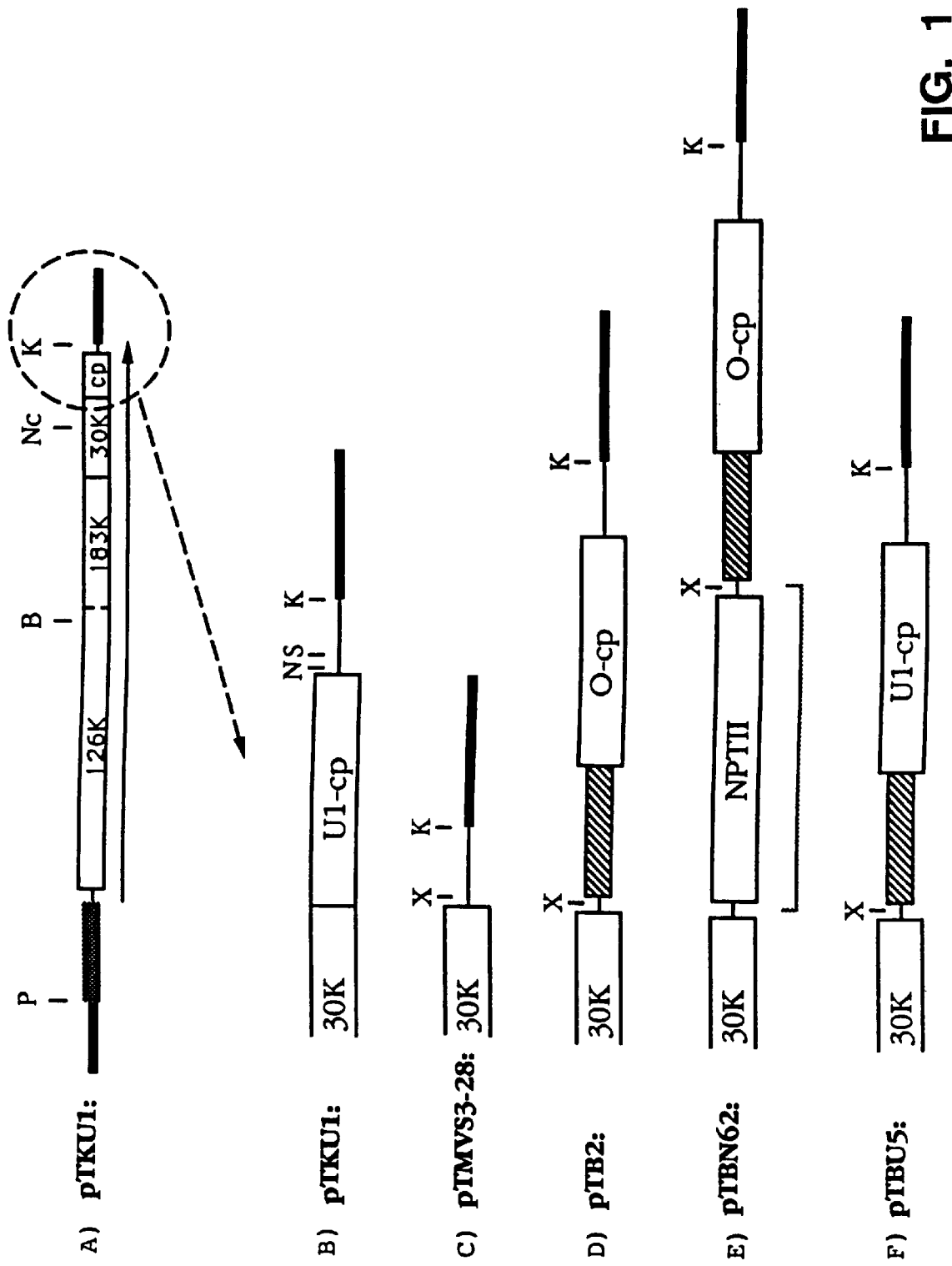
FIG. 1 illustrates several vectors prepared in accordance with the present invention and restriction sites. U1 is the native viral nucleic acid, O is a non-native viral nucleic acid, and the hatched area is a non-native viral subgenomic promoter. The restriction sites are: X-XhoI, N-NsiI, K-KpnI, S-SplI, B-BamHI, No-NcoI, P-PstI. The hatched box (e.g., in TB2) represents the promoter of TMV-O, i.e., 203 bp upstream of the coat protein initiation codon, and the stipled box represents a phage promoter. The open boxes represent open reading frames, and the solid boxes represent cloning vector sequences. The vectors are as follows: A) and B) pTKU1, C) pTMVS3-28, D) pTB2, E) pTBN62 and F) pTBU5.

The present invention relates to recombinant viral nucleic acids possessing enhanced stability within a host, thereby enabling the sustained systemic transcription of a nucleotide sequence within the host. Enhanced stability within the host has been accomplished by the use of a dual subgenomic promoter system which is believed to reduce the frequency of recombination leading to the regeneration of the wild type virus.

Specifically, the present invention relates to a recombinant viral nucleic acid selected from a (+) sense, single stranded RNA virus possessing a native subgenomic promoter encoding for a first viral subgenomic promoter, a nucleic acid sequence that codes for a viral coat protein whose transcription is regulated by the first viral subgenomic promoter, a second viral subgenomic promoter and a second nucleic acid sequence whose transcription is regulated by the second viral subgenomic promoter. The first and second viral subgenomic promoters of the recombinant viral nucleic acid do not have homologous sequences relative to each other. The recombinant viral nucleic acid provides the particular advantage that it systemically transcribes the second nucleic acid in the host. Host organisms encompassed by the present invention are eukaryotics, particularly animals and plants.

The requirement that the recombinant viral nucleic acid comprise a second nucleic acid that is not naturally associated with the plus sense single stranded RNA virus from which the nucleic acid is derived distinguishes the recombinant viral nucleic acid from nature. A description of subgenomic promoters is presented in R. E. F. Matthews, *Plant Virology,* 3rd Edition, Academic Press, Inc., San Diego p. 180 (1991).

The recombinant viral nucleic acids of the present invention systemically express the second nucleic acid sequence within the infected host. Systemic expression is enabled by the difference in the nucleic acid sequences between the first and second subgenomic promoters which serves to inhibit recombination of the subgenomic promoters with each other and other parts of the viral genome to yield the wild type virus. As a result, the recombinant viral nucleic acids of the present invention are sufficiently stable within the host to enable the sustained systemic transcription of the second nucleic acid sequence. Prior art vectors used the same subgenomic promoter (Ahlquist, et al., *J. Mol. Biol.* 153:23 (1981)) and were not able to achieve systemic transcription of a foreign nucleic acid sequence. By contrast, Applicants have accomplished the highest accumulation of a foreign protein ever reported in any genetically engineered using a vector designed according to the present invention. See Kumagai, et al., *Proc. Natl. Acad. Sci.* 90:427–430 (1993).

The essential requirement of the present invention is that the recombinant viral nucleic acid contain subgenomic promoters that do not contain homologous sequences relative to each other. Otherwise, there is no requirement that the coat protein sequence, the foreign nucleic acid sequence and the subgenomic promoters be native or non-native to the recombinant viral nucleic acid. Rather, the coat protein sequence employed in the recombinant nucleic acid sequence may be either native or non-native to the viral nucleic acid. Similarly, the subgenomic promoters for the coat protein sequence and for the foreign nucleic acid sequence may be either native or non-native to the viral nucleic acid.

For example, in one embodiment of the present invention, a viral nucleic acid is provided in which the coat protein coding sequence and subgenomic promoter for the viral nucleic acid have been deleted and replaced with a non-native viral coat protein coding sequence and a subgenomic promoter that is not native to the viral nucleic acid. It is preferred that the subgenomic promoter for the non-native coat protein coding sequence be capable of expressing in the host, packaging of the recombinant viral nucleic acid, and ensuring a systemic infection of the host by the recombinant viral nucleic acid.

According to the present invention, it is also possible for the recombinant viral nucleic acid to encode for more than one foreign nucleic acid sequence. If more than one nucleic acid sequence is included, each subgenomic promoter used to promote each foreign nucleic acid sequence must not have homologous sequences relative to each other.

In a second embodiment, a recombinant viral nucleic acid is provided as in the first embodiment except that the native coat protein coding sequence is placed adjacent one of the non-native coat protein subgenomic promoters instead of a non-native coat protein coding sequence.

In a third embodiment, a recombinant viral nucleic acid is provided in which the native coat protein gene is adjacent to its subgenomic promoter and one or more non-native subgenomic promoters have been inserted into the viral nucleic acid. The inserted non-native subgenomic promoters are capable of transcribing or expressing adjacent genes in a host and are incapable of recombination with each other and with native subgenomic promoters. Foreign nucleic acid sequences may be inserted adjacent the subgenomic viral promoters such that the foreign sequences are transcribed or expressed in the host under control of the subgenomic promoters to produce the desired product.

In a fourth embodiment, a recombinant viral nucleic acid is provided as in the third embodiment except that the native coat protein coding sequence is replaced by a non-native coat protein coding sequence.

The viral vectors are encapsidated by the coat proteins encoded by the recombinant viral nucleic acid to produce a recombinant virus. The recombinant viral nucleic acid or recombinant virus is used to infect appropriate hosts. The recombinant viral nucleic acid is capable of replication in the host, systemic spread in the host, and transcription or expression of foreign gene(s) in the host to produce the desired product. Such products include therapeutic and other useful polypeptides or proteins such as, but not limited to, enzymes, complex biomolecules, ribozymes, or polypeptide or protein products resulting from anti-sense RNA expression.

The present invention also relates to viruses containing the viral vectors which are infective, production cells which are capable of producing the viruses or parts thereof, a host infected by the viruses of the invention, the gene products produced by expression of the viral nucleic acids and a process for the production of a desired product by growing the infected hosts.

In order to provide a clear and consistent understanding of the specification and the claims, including the scope given herein to such terms, the following definitions are provided:

Adjacent: A position in a nucleotide sequence immediately 5' or 3' to a defined sequence.

Anti-Sense Mechanism: A type of gene regulation based on controlling the rate of translation of mRNA to protein due to the presence in a cell of an RNA molecule complementary to at least a portion of the mRNA being translated.

Cell Culture: A proliferating mass of cells which may be in either an undifferentiated or differentiated state.

Chimeric Sequence or Gene: A nucleotide sequence derived from at least two heterologous parts. The sequence may comprise DNA or RNA.

Coding Sequence: A deoxyribonucleotide sequence which, when transcribed and translated, results in the formation of a cellular polypeptide or a ribonucleotide sequence which, when translated, results in the formation of a cellular polypeptide.

Compatible: The capability of operating with other components of a system. A vector or viral nucleic acid which is compatible with a host is one which is capable of replicating in that host. A coat protein which is compatible with a viral nucleotide sequence is one capable of encapsidating that viral sequence.

Gene: A discrete nucleic acid sequence responsible for a discrete cellular product.

Host: A cell, tissue or organism capable of replicating a vector or viral nucleic acid and which is capable of being infected by a virus containing the viral vector or viral nucleic acid. This term is intended to include procaryotic and eukaryotic cells, organs, tissues or organisms, where appropriate.

Infection: The ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

Non-Native: Any sequence that does not naturally occur in the virus or organism in which the sequence is said to be non-native.

Phenotypic Trait: An observable property resulting from the expression of a gene.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in planta or in culture. This term is intended to include a whole plant, plant cell, plant organ, protoplast, cell culture, or any group of plant cells organized into a structural and functional unit.

Production Cell: A cell, tissue or organism capable of replicating a vector or a viral vector, but which is not necessarily a host to the virus. This term is intended to include prokaryotic and eukaryotic cells, organs, tissues or organisms, such as bacteria, yeast, fungus and tissue.

Promoter: The 5'-flanking, non-coding sequence adjacent a coding sequence which is involved in the initiation of transcription of the coding sequence.

Protoplast: An isolated cell without cell walls, having the potency for regeneration into cell culture or a whole host.

Recombinant Viral Nucleic Acid: Viral nucleic acid which has been modified to contain nucleic acid sequences that are not native to the virus.

Recombinant Virus: A virus containing the recombinant viral nucleic acid.

Subgenomic Promoter: A promoter of a subgenomic mRNA of a viral nucleic acid. Subgenomic promoters are defined in R. E. F. Matthews, *Plant Virology*, 3rd Edition, Academic Press, Inc., San Diego p. 180 (1991).

Substantial Sequence Homology: Denotes nucleotide sequences that are substantially functionally equivalent to one another. Nucleotide differences between such sequences having substantial sequence homology will be de minimus in affecting function of the gene products or an RNA coded for by such sequence.

Transcription: Production of an RNA molecule by RNA polymerase as a complementary copy of a DNA sequence.

Vector: A self-replicating DNA molecule which transfers a DNA segment between cells.

Virus: An infectious agent composed of a nucleic acid encapsidated in a protein. A virus may be a mono-, di-, tri- or multi-partite virus, as described above.

The present invention provides for the infection of a host by a recombinant virus containing recombinant viral nucleic acid or by the recombinant viral nucleic acid which contains one or more non-native nucleic acid sequences which are transcribed or expressed in the infected tissues of the host. The product of the coding sequences may be recovered from the host or cause a phenotypic trait, such as male sterility, in the host.

The present invention has a number of advantages, one of which is that the transformation and regeneration of target organisms is unnecessary. Another advantage is that it is unnecessary to develop vectors which integrate a desired coding sequence in the genome of the target organism. Existing organisms can be altered with a new coding sequence without the need of going through a germ cell. The present invention also gives the option of applying the coding sequence to the desired organism, tissue, organ or cell. Recombinant viral nucleic acids are also stable for the foreign coding sequences, and the recombinant virus or recombinant viral nucleic acids are capable of systemic infection in the host.

Chimeric genes and vectors and recombinant viral nucleic acids according to this invention are constructed using techniques well known in the art. Suitable techniques have been described in Maniatis, T. et al., *Molecular Cloning*, (1st Ed.) and Sambrook, J. et al., (2nd Ed.), Cold Spring Harbor Laboratory, Cold Spring Harbor (1982, 1989); *Methods in Enzymol.*, Vols. 68, 100, 101, 118 and 152–155 (1979, 1983, 1986 and 1987); and *Molecular Cloning*, D. M. Clover, Ed., IRL Press, Oxford (1985). Medium compositions have been described in Miller, J. H., *Experiments in Molecular Genetics*, Cold Spring Harbor Laboratory, New York (1972), as well as the references previously identified. DNA manipulations and enzyme treatments are carried out in accordance with manufacturers' recommended procedures.

An important feature of the present invention is the preparation of recombinant viral nucleotide sequences (RVNA) which are capable of replication in a compatible host but which themselves are incapable of infecting the host. The nucleotide sequence has substantial sequence homology to a viral nucleotide sequence. The viral nucleotide sequence may be a prokaryotic or eukaryotic viral nucleotide sequence. Suitable viral nucleotide sequences include those of viruses which infect bacteria, yeast, fungus, animals and plants. A partial listing of suitable viruses has been described above. The nucleotide sequence may be an RNA, DNA, cDNA or chemically synthesized RNA or DNA.

The first step in achieving any of the features of the invention is to modify the nucleotide sequences of the viral nucleotide sequence by known conventional techniques such that one or more different subgenomic promoters are inserted into the viral nucleic acid without destroying the biological function of the viral nucleic acid. Subgenomic promoters are different when they do not have homologous sequences relative to each other such that the resulting recombinant viral nucleic acids are stable in vivo. It is believed that the differences in the subgenomic promoter sequences create enhanced stability by reducing the frequency of recombination. The subgenomic promoters are capable of transcribing or expressing adjacent nucleic acid sequences in a host infected by the recombinant viral nucleic acid or recombinant virus.

The native coat protein coding sequence may be retained or replaced with a non-native coat protein coding sequence. The coat protein coding sequence may be placed under the control of a native or non-native subgenomic promoter. The coat protein is involved in the systemic infection of the host.

Some of the viruses which may be used in the present invention include but are not limited to alphaviruses such as Eastern Equine Encephalomyelitis virus (EEEV), Western Equine Encephalomyelitis virus (WEEV), Venezuelan Encephalomyelitis virus (VEV), Sindbis virus, Semliki Forest virus (SFV) and Ross River virus (RRV), the rhinoviruses such as human rhinovirus 2 (HRV2) and human rhinovirus type 89 (HRV89), the polioviruses such as poliovirus 2 (Pv2) and poliovirus 3 (PV3), simian virus 40 (SV40), viruses from the tobacco mosaic virus group such as Tobacco Mosaic virus (TMV), Cowpea Mosaic virus (CMV) Alfalfa Mosaic virus (AmV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), adenovirus type 2 and geminiviruses such as tomato golden mosaic virus (TGMV), cassava latent virus and maize streak virus. Each of these groups of suitable viruses is characterized below.

Alphaviruses

The alphaviruses are a genus of viruses of the family Togaviridae. Almost all of the members of this genus are transmitted by mosquitoes, and may cause diseases in man or animals. Some of the alphaviruses are grouped into three serologically defined complexes. The complex-specific antigen is associated with the E1 protein of the virus, and the species-specific antigen is associated with the E2 protein of the virus.

The Semliki Forest virus complex includes Bebaru virus, Chikungunya Fever virus, Getah virus, Mayaro Fever virus, O'nyongnyong Fever virus, Ross River virus, Sagiyama virus, Semliki Forest virus and Una virus. The Venezuelan Equine Encephalomyelitis virus complex includes Cabassou virus, Everglades virus, Mucambo virus, Pixuna virus and Venezuelan Equine Encephalomyelitis virus. The Western Equine Encephalomyelitis virus complex includes Aura virus, Fort Morgan virus, Highlands J virus, Kyzylagach virus, Sindbis virus, Western Equine Encephalomyelitis virus and Whataroa virus.

The alphaviruses contain an icoschedral nucleocapsid consisting of 180 copies of a single species of capsid protein complexed with a plus-stranded 425 to 498 mRNA of up to about 11,703 nucleotides. The alphaviruses mature when preassembled nucleocapsid is surrounded by a lipid envelope containing two virus encoded integral membrane glycoproteins, called E1 and E2. The envelope is acquired when the capsid, assembled in the cytoplasm, buds through the plasma membrane. The envelope consists of a lipid bilayer derived from the host cell.

The 425 to 498 mRNA encodes a glycoprotein which is contranslationally cleaved into nonstructural proteins and structural proteins. The 3' one-third of the RNA genome consists of a 265 mRNA which encodes for the capsid protein and the E3, E2, K6 and E1 glycoproteins. The capsid protein is cotranslationally cleaved from the E3 protein. It is hypothesized that the amino acid triad of His, Asp and Ser at the COOH terminus of the capsid protein comprises a serine protease responsible for cleavage. Hahn, C. S. et al., *Proc. Natl. Acad. Sci. U.S.A.* 82:4648 (1985). Cotranslational cleavage also occurs between E2 and K6 proteins. Thus two proteins PE2 which consists of E3 and E2 prior to cleavage and an E1 protein comprising K6 and E1 are formed. These proteins are cotranslationally inserted into the endoplasmic reticulum of the host cell, glycosylated and transported via the Golgi apparatus to the plasma membrane where they can be used for budding. At the point of virion maturation the E3 and E2 proteins are separated. The E1 and E2 proteins are incorporated into the lipid envelope.

It has been suggested that the basic amino-terminal half of the capsid protein stabilizes the interaction of capsid with genomic RNA, Garoff, H., et al., *Nature* 288:236 (1980); or interacts with genomic RNA to initiate encapsidation, Strauss E. G. et al., in the *Togaviruses and Flaviviruses,* Ed. S. Schlesinger & M. Schlesinger, Plenum Press, New York, p. 35–90, (1980). These suggestions imply that the origin of assembly is located either on the unencapsidated genomic RNA or at the amino-terminus of the capsid protein.

It has been suggested that E3 and K6 function as signal sequences for the insertion of PE2 and E1, respectively, into the endoplasmic reticulum. Garoff, H., et al., *Nature* 288:236 (1980); Delgarno, L. et al., *Virology* 120, 170 (1983).

Work with temperature sensitive mutants of alphaviruses has shown that failure of cleavage of the structural proteins results in failure to form mature virions. Lindquist, B. H. et al., *Virology* 151:10 (1986) characterized a temperature sensitive mutant of Sindbis virus, $t_s$20. Temperature sensitivity results from an A–U change at nucleotide 9502. The $t_s$ lesion present cleavage of PE2 to E2 and E3 and the final maturation of progeny virions at the nonpermissive temperature. Hahn, C. S., et al., *Proc. Natl. Acad. Sci. USA,* 82:4648 (1985) reported three temperature sensitive mutations in the capsid protein which prevents cleavage of the precursor polyprotein at the nonpermissive temperature. The failure of cleavage resulted in no capsid formation and very little envelope protein.

Defective interfering RNA's (DI particles) of Sindbis virus are helper-dependent deletion mutants which interfere specifically with the replication of the homologous standard virus. Perrault, J., *Microbiol. Immunol.* 93:151 (1981). DI particles have been found to be functional vectors for introducing at least one foreign gene into cells. Levis, R., *Proc. Natl. Acad. Sci. U.S.A.* 84:4811 (1987).

It has been found that it is possible to replace at least 1689 internal nucleotides of a DI genome with a foreign sequence and obtain RNA that will replicate and be encapsidated. Deletions of the DI genome do not destroy biological activity. The disadvantages of the system are that DI particles undergo apparently random rearrangements of the internal RNA sequence and size alterations. Monroe, S. S. et al., *J. Virology* 49:865 (1984). Expression of a gene inserted into the internal sequence is not as high as expected. Levis, R. et al., supra, found that replication of the inserted gene was excellent but translation was low. This could be the result of competition with whole virus particles for translation sites and/or also from disruption of the gene due to rearrangement through several passages.

Two species of mRNA are present in alphavirus-infected cells: A 42S mRNA region, which is packaged into nature virions and functions as the message for the nonstructural proteins, and a 26S mRNA, which encodes the structural polypeptides. The 26S mRNA is homologous to the 3' third of the 42S mRNA. It is translated into a 130K polyprotein that is cotranslationally cleaved and processed into the capsid protein and two glycosylated membrane proteins, E1 and E2.

The 26S mRNA of Eastern Equine Encephalomyelitis (EEE) strain 82V-2137 was cloned and analyzed by Chang et al. *J. Gen. Virol.* 68:2129 (1987). The 26S mRNA region encodes the capsid proteins, E3, E2, 6K and E1. The amino terminal end of the capsid protein is thought to either stabilize the interaction of capsid with mRNA or to interact with genomic RNA to initiate encapsidation.

Uncleaved E3 and E2 proteins called PE2 is inserted into the host endoplasmic reticulum during protein synthesis. The PE2 is thought to have a region common to at least five alphaviruses which interacts with the viral nucleocapsid during morphogenesis.

The 6K protein is thought to function as a signal sequence involved in translocation of the E1 protein through the membrane. The E1 protein is thought to mediate virus fusion and anchoring of the E1 protein to the virus envelope.

Rhinoviruses

The rhinoviruses are a genus of viruses of the family Picornaviridae. The rhinoviruses are acid-labile, and are therefore rapidly inactivated at pHs less than about 6. The rhinoviruses commonly infect the upper respiratory tract of mammals.

Human rhinoviruses are the major causal agents of the common cold, and many serotypes are known. Rhinoviruses may be propagated in various human cell cultures, and have an optimum growth temperature of about 33° C. Most strains of rhinoviruses are stable at or below room temperature and can withstand freezing. Rhinoviruses can be inactivated by citric acid, tincture of iodine or phenol/alcohol mixtures.

The complete nucleotide sequence of human rhinovirus 2 (HRV2) has been sequenced. The genome consists of 7102 nucleotides with a long open reading frame of 6450 nucleotides which is initiated 611 nucleotides from the 5' end and stops 42 nucleotides from the poly(A) tract. Three capsid proteins and their cleavage cites have been identified.

Rhinovirus RNA is single-stranded and positive sense. The RNA is not capped, but is joined at the 5' end to a small virus encoded protein, virion-protein genome-linked (VPg). Translation is presumed to result in a single polyprotein which is broken by proteolytic cleavage to yield individual virus proteins.

An icosahedral viral capsid contains 60 copies each of 4 virus proteins VP1, VP2, VP3 and VP4 and surrounds the RNA genome. Medappa, K. C. et al. *Virology* 44:259 (1971).

Analysis of the 610 nucleotides preceding the long open reading frame shows several short open reading frames. However, no function can be assigned to the translated proteins since only two sequences show homology throughout HRV2, HRV14 and the 3 serotypes of poliovirus. These two sequences may be critical in the life cycle of the virus. They are a stretch of 16 bases beginning at 436 in HRV2 and a stretch of 23 bases beginning at 531 in HRV2. Cutting or removing these sequences from the remainder of the sequence for non-structural proteins could have an unpredictable effect upon efforts to assemble a mature virion.

The capsid proteins of HRV2: VP4, VP2, VP3 and VP1 begin at nucleotide 611, 818, 1601 and 2311, respectively. The cleavage point between VP1 and P2A is thought to be around nucleotide 3255. Skern, T. et al., *Nucleic Acids Research* 13:2111 (1985).

Human rhinovirus type 89 (HRV89) is very similar to HRV2. It contains a genome of 7152 nucleotides with a single large open reading frame of 2164 codons. Translation begins at nucleotide 619 and ends 42 nucleotides before the poly(A) tract. The capsid structural proteins, VP4, VP2, VP3 and VP1 are the first to be translated. Translation of VP4 begins at 619. Cleavage cites occur at:

VP4/VP2 825 determined

VP2/VP3 1627 determined

VP3/VP1 2340 presumptive

VP1/P2-A 3235 presumptive

Duechler, M. et al., *Proc. Natl. Acad. Sci. USA* 84:2605 (1987).

Polioviruses

Polioviruses are the causal agents of poliomyelitis in man, and are one of three groups of Enteroviruses. Enteroviruses are a genus of the family Picornaviridae (also the family of rhinoviruses). Most enteroviruses replicate primarily in the mammalian gastrointestinal tract, although other tissues may subsequently become infected. Many enteroviruses can be propagated in primary cultures of human or monkey kidney cells and in some cell lines (e.g. HeLa, Vero, WI-38). Inactivation of the enteroviruses may be accomplished with heat (about 50° C.), formaldehyde (3%), hydrochloric acid (0.1N) or chlorine (ca. 0.3–0.5 ppm free residual $Cl_2$).

The complete nucleotide sequence of poliovirus PV2 (Sab) and PV3 (Sab) have been determined. They are 7439 and 7434 nucleotide in length, respectively. There is a single long open reading frame which begins more than 700 nucleotides from the 5' end. Poliovirus translation produces a single polyprotein which is cleaved by proteolytic processing. Kitamura, N. et al., *Nature,* 291:547 (1981).

It is speculated that these homologous sequences in the untranslated regions play an essential role in viral replication such as:

1. viral-specific RNA synthesis;
2. viral-specific protein synthesis; and
3. packaging Toyoda, H. et al., *J. Mol. Biol.,* 174:561 (1984).

The structures of the serotypes of poliovirus have a high degree of sequence homology. Their coding sequences the same proteins in the same order. Therefore, genes for structural proteins are similarly located. In PV1, PV2 and PV3, the polyprotein begins translation near the 750 nucleotide. The four structural proteins VP4, VP2, VP3 and VP1 begin at about 745, 960, 1790 and 2495, respectively, with VPI ending at about 3410. They are separated in vivo by proteolytic cleavage, rather than by stop/start codons.

Simian Virus 40

Simian virus 40 (SV40) is a virus of the genus Polyomavirus, and was originally isolated from the kidney cells of the rhesus monkey. The virus is commonly found, in its latent form, in such cells. Simian virus 40 is usually non-pathogenic in its natural host.

Simian virus 40 virions are made by the assembly of three structural proteins, VP1, VP2 and VP3. Girard, M. et al., *Biochem. Biophys. Res. Commun.* 40:97 (1970); Prives, C. L. et al., *Proc. Natl. Acad. Sci. USA* 71:302 (1974); and Rozenblatt, S. et al., *Proc. Natl. Acad. Sci. USA* 73:2747 (1976). The three corresponding viral genes are organized in a partially overlapping manner. They constitute the late genes portion of the genome. Tooze, 3., *Molecular Biology of Tumor Viruses,* 2nd Ed. Part 2, p. 799–831 (1980). Cold Spring Harbor Laboratory, Cold Spring Harbor, N.Y. Capsid proteins VP2 and VP3 are encoded by nucleotides 545 to 1601 and 899 to 1601, respectively, and both are read in the same frame. VP3 is therefore a subset of VP2. Capsid protein VP1 is encoded by nucleotides 1488–2574. The end of the VP2–VP3 open reading frame therefore overlaps the VP1 by 113 nucleotides but is read in an alternative frame. Tooze, 3., *Molecular Biology of Tumor Viruses,* 2nd Ed. Part 2, p. 799–831 (1980). Cold Spring Harbor Laboratory, Cold Spring Harbor, N.Y.; Sychowski, C. et al., *J. Virology* 61:3862 (1987).

Adenoviruses

Adenovirus type 2 is a member of the adenovirus family or adenovirus. This family of viruses are non-enveloped, icosahedral, linear, double-stranded DNA-containing viruses which infect mammals or birds.

The adenovirus virion consists of an icosahedral capsid enclosing a core in which the DNA genome is closely associated with a basic (arginine-rich) viral polypeptide VII. The capsid is composed of 252 capsomeres: 240 hexons (capsomers each surrounded by 6 other capsomers) and 12 pentons (one at each vertex, each surrounded by 5 'peripentonal' hexons) Each penton consists of a penton base (composed of viral polypeptide III) associated with one (in mammalian adenoviruses) or two (in most avian adenoviruses) glycoprotein fibres (viral polypeptide IV) The fibres can act as haemagglutinins and are the sites of attachment of the virion to a host cell-surface receptor. The hexons each consist of three molecules of viral polypeptide II; they make up the bulk of the icosahedron. Various other minor viral polypeptides occur in the virion.

The adenovirus dsDNA genome is covalently linked at the 5' end of each strand to a hydrophobic 'terminal protein', TP (molecular weight about 55,000); the DNA has an inverted terminal repeat of different length in different adenoviruses. In most adenoviruses examined, the 5'-terminal residue is dCMP.

During its replication cycle, the virion attaches via its fibres to a specific cell-surface receptor, and enters the cell by endocytosis or by direct penetration of the plasma membrane. Most of the capsid proteins are removed in the cytoplasm. The virion core enters the nucleus, where the uncoating is completed to release viral DNA almost free of virion polypeptides. Virus gene expression then begins. The viral dsDNA contains genetic information on both strands. Early genes (regions E1a, E1b, E2a, E3, E4) are expressed before the onset of viral DNA replication. Late genes (regions L1, L2, L3, L4 and L5) are expressed only after the initiation of DNA synthesis. Intermediate genes (regions E2b and IVa$_2$) are expressed in the presence or absence of DNA synthesis. Region E1a encodes proteins involved in the regulation of expression of—other early genes, and is also involved in transformation. The RNA transcripts are capped (with m7G$^5$ppp$^5$N) and polyadenylated in the nucleus before being transferred to the cytoplasm for translation.

Viral DNA replication requires the terminal protein, TP, as well as virus-encoded DNA polymerase and other viral and host proteins. TP is synthesized as an 80K precursor, pTP, which binds covalently to nascent replicating DNA strands. pTP is cleaved to the mature 55K TP late in virion assembly; possibly at this stage, pTP reacts with a dCTP molecule and becomes covalently bound to a dCMP residue, the 3' OH of which is believed to act as a primer for the initiation of DNA synthesis. Late gene expression, resulting in the synthesis of viral structural proteins, is accompanied by the cessation of cellular protein synthesis, and virus assembly may result in the production of up to $10^5$ virions per cell.

Tobacco Mosaic Virus Group

Tobacco Mosaic virus (TMV) is a member of the Tobamoviruses. The TMV virion is a tubular filament, and comprises coat protein sub-units arranged in a single right-handed helix with the single-stranded RNA intercalated between the turns of the helix. TMV infects tobacco as well as other plants. TMV is transmitted mechanically and may remain infective for a year or more in soil or dried leaf tissue.

The TMV virions may be inactivated by subjection to an environment with a pH of less than 3 or greater than 8, or by formaldehyde or iodine. Preparations of TMV may be obtained from plant tissues by $(NH_4)_2SO_4$ precipitation, followed by differential centrifugation.

The TMV single-stranded RNA genome is about 6400 nucleotides long, and is capped at the 5' end but not polyadenylated. The genomic RNA can serve, as mRNA for a protein of a molecular weight of about 130,000 (130K) and another produced by read-through of molecular weight about 180,000 (180K). However, it cannot function as a messenger for the synthesis of coat protein. Other genes are expressed during infection by the formation of monocistronic, 3'-coterminal sub-genomic mRNAs, including one (LMC) encoding the 17.5K coat protein and another (I$_2$) encoding a 30K protein. The 30K protein has been detected in infected protoplasts, Virology 132:71 (1984), and it is involved in the cell-to-cell transport of the virus in an infected plant, Deom, C. M. et al., Science 237:389 (1987). The functions of the two large proteins are unknown.

Several double-stranded RNA molecules, including double-stranded RNAs corresponding to the genomic, I$_2$ and LMC RNAs, have been detected in plant tissues infected with TMV. These RNA molecules are presumably intermediates in genome replication and/or mRNA synthesis processes which appear to occur by different mechanisms.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3' end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'-direction from the nucleation site).

Another member of the Tobamoviruses, the Cucumber green mottle mosaic virus watermelon strain (CGMMV-W) is related to the cucumber virus. Noru, Y. et al., *Virology* 45:577 (1971). The coat protein of CGMMV-W interacts with RNA of both TMV and CGMMV to assemble viral particles in vitro. Kurisu et al., *Virology* 70:214 (1976).

Several strains of the tobamovirus group are divided into two subgroups, on the basis of the location of the assembly of origin. F'ukuda, M. et al., Proc. Nat. Acad. Sci. USA 78:4231 (1981). Subgroup I, which includes the vulgare, OM, and tomato strain, has an origin of assembly about 800–1000 nucleotides from the 3' end of the RNA genome, and outside the coat protein cistron. Lebeurier, G. et al., Proc. Nat. Acad. Sci. USA 74:1913 (1977); and Fukuda, M. et al., Virology 101:493 (1980). Subgroup II, which includes CGMMV-W and cowpea strain (Cc) has an origin of assembly about 300–500 nucleotides from the 3' end of the RNA genome and within the coat-protein cistron. Fukuda, M. et al., Virology reactions, more efficient metabolism, increased fat and lipid metabolism for the production of leaner meats, replacement of deficient enzymes and better utilization of feed. Like plant cells, other examples of useful phenotypic traits for animal cells include the production of important proteins or other products for commercial use, such as lipase, melanin, pigments, antibiotics, tissue plasminogen activator (TPA), human growth hormone and the like, or a secondary metabolite dose production is desired in a bioreactor.

Brome Mosaic Virus Group

Brome mosaic virus (BV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BV, other bromoviruses include broad bean mottle virus and cowpea chlorotic mottle virus.

Typically, a bromovirus virion is icosahedral, with a diameter of about 26 mm, containing a single species of coat protein. The bromovirus genome has three molecules of linear, positive-sense, single-stranded RNA, and the coat protein mRNA is also encapsidated. The RNAs each have a capped 5' end, and a tRNA-like structure (which accepts tyrosine) at the 3' end. Virus assembly occurs in the cytoplasm. The complete nucleotide sequence of BMV has been identified and characterized as described by Alquist et al., *J. Mol. Biol.* 153:23 (1981).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by Polvmvxa araminis (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedra), composed of a single type of protein (with a molecular weight of about $2.7–3.4\times10^4$). Each geminivirus virion contains one molecule of circular, positive-sense, single-stranded DNA. In some geminiviruses (i.e., Cassava latent virus and bean golden mosaic cirus) the genome appears to be bipartite, containing two single-stranded DNA molecules.

The nucleic acid of any suitable plant virus can be utilized to prepare the recombinant plant viral nucleic acid of the present invention. The nucleotide sequence of the plant virus is modified, using conventional techniques, by the insertion of one or more subgenomic promoters into the plant viral nucleic acid. The subgenomic promoters are capable of functioning in the specific host plant. For example, if the host is tobacco, TMV will be utilized. The inserted subgenomic promoters must be compatible with the TMV nucleic acid and capable of directing transcription or expression of adjacent nucleic acid sequences in tobacco.

The native coat protein gene could also be retained and a non-native nucleic acid sequence inserted within it to create a fusion protein as discussed below. In this example, a non-native coat protein gene is also utilized.

The native or non-native coat protein gene is utilized in the recombinant plant viral nucleic acid. Whichever gene is utilized may be positioned adjacent its natural subgenomic promoter or adjacent one of the other available subgenomic promoters. The non-native coat protein, as is the case for the native coat protein, is capable of encapsidating the recombinant plant viral nucleic acid and providing for systemic spread of the recombinant plant viral nucleic acid in the host plant. The coat protein is selected to provide a systemic infection in the plant host of interest. For example, the TMV-O coat protein provides systemic infection in *N. benthamiana,* whereas TMV-U1 coat protein provides systemic infection in *N. tabacum.*

The recombinant plant viral nucleic acid is prepared by cloning viral nucleic acid in an appropriate production cell. If the viral nucleic acid is DNA, it can be cloned directly into a suitable vector using conventional techniques. One technique is to attach an origin of replication to the viral DNA which is compatible with the production cell. If the viral nucleic acid is RNA, a full-length DNA copy of the viral genome is first prepared by well-known procedures. For example, the viral RNA is transcribed into DNA using reverse transcriptase to produce subgenomic DNA pieces, and a double-stranded DNA made using DNA polymerases. The DNA is then cloned into appropriate vectors and cloned into a production cell. The DNA pieces are mapped and combined in proper sequence to produce a full-length DNA copy of the viral RNA genome, if necessary. DNA sequences for the subgenomic promoters, with or without a coat protein gene, are then inserted into the nucleic acid at non-essential sites, according to the particular embodiment of the invention utilized. Non-essential sites are those that do not affect the biological properties of the plant viral nucleic acid. Since the RNA genome is the infective agent, the cDNA is positioned adjacent a suitable promoter so that the RNA is produced in the production cell. The RNA is capped using conventional techniques, if the capped RNA is the infective agent.

In the case of alphaviruses, the E1 and E2 glycoproteins may play a role in transmissibility of the virus (Garaff, H. et al., *Nature* 228, 236 (1980)). These glycoproteins are incorporated in a liquid envelope which surrounds the coat protein. The nucleotide sequence which codes for the E1 and E2 glycoproteins is adjacent to the coding sequence for the coat protein in alphavirus RNA. Therefore the E1 and E2 glycoprotein coding sequences can be removed with the coat protein coding sequence by known conventional techniques.

A second feature of the present invention is a recombinant viral nucleic acid capable of transcribing in the host one or more nucleic acid sequences non-native to the viral nucleic acid. The non-native nucleic acid sequence may be placed adjacent to a native or non-native viral subgenomic promoter including the native coat protein gene promoter. The non-native nucleic acid is inserted by conventional techniques, or the non-native nucleic acid sequence can be inserted into or adjacent to the native coat protein coding sequence such that a fusion protein is produced. The non-native nucleic acid sequence which is transcribed may be transcribed as an RNA which is capable of regulating the expression of a phenotypic trait by an anti-sense mechanism. Alternatively, the non-native nucleic acid sequence in the recombinant viral nucleic acid may be transcribed and translated in the host, to produce a phenotypic trait. The non-native nucleic acid sequence(s) may also code for the expression of more than one phenotypic trait. The recombinant viral nucleic acid containing the non-native nucleic acid sequence is constructed using conventional techniques such that non-native nucleic acid sequence(s) are in proper orientation to whichever viral subgenomic promoter is utilized.

Useful phenotypic traits in plant cells include, but are not limited to, improved tolerance to herbicides, improved tolerance to extremes of heat or cold, drought, salinity or osmotic stress; improved resistance to pests (insects, nematodes or arachnids) or diseases (fungal, bacterial or viral) production of enzymes or secondary metabolites; male or female sterility; dwarfness; early maturity; improved yield, vigor, heterosis, nutritional qualities, flavor or processing properties, and the like. Other examples include the production of important proteins or other products for commercial use, such as lipase, melanin, pigments, antibodies, hormones, pharmaceuticals, antibiotics and the like. Another useful phenotypic trait is the production of degradative or inhibitory enzymes, such as are utilized to prevent or inhibit root development in malting barley. The phenotypic trait may also be a secondary metabolite whose production is desired in a bioreactor.

In the case of animal cells, useful phenotypic traits include, but are not limited to, the ability to grow in culture, the elimination of the characteristic of attaching to a substrate when grown in culture, enhanced immune response, minimization of inappropriate immune responses such as autoimmune reactions, more efficient metabolism, increased fat and lipid metabolism for the production of leaner meats, replacement of deficient enzymes and better utilization of feed. Like plant cells, other examples of useful phenotypic traits for animal cells include the production of important proteins or other products for commercial use, such as lipase, melanin, pigments, antibiotics, tissue plasminogen activator (TPA), human growth hormone and the like, or a secondary metabolite dose production is desired in a bioreactor.

An example of a chimeric nucleotide sequence is one which contains a first nucleotide sequence having substantial sequence homology to TMV and a second nucleotide sequence which is a coding sequence for tyrosinase. In a second example, the virus is oat mosaic virus (OMV) or rice necrosis virus (RNV). OMV and RNV are capable of infecting most monocot species including, but not limited to, barley and corn. In a third example, the second nucleotide sequence is the coding sequence for cyclodextrin glucanotransferase. Potato virus Y (PVY) or potato virus X (PVX) is used in a fourth example. In a fifth example, a chimeric nucleotide sequence contains a first nucleotide sequence having substantial sequence homology to gemini tomato golden mosaic virus (TGMV), and a second nucleotide sequence which codes for human tissue plasminogen activator (t-PA). t-PA is isolated from plasmid pt-PAtrp12; ATCC No. 40404 (U.S. Pat. No. 4,766,075). TGMV is capable of infecting a wide variety of both dicotyledonous and monocotyledonous plants including tobacco, tomato, bean, soya bean, sugar beet, cassava, cotton, maize, oats and wheat. Other important examples are illustrated herein.

A second nucleotide sequence can be inserted into the first nucleotide sequence prepared above such that it is adjacent a viral promoter. Since the location of the promoter of the viral coat protein gene is known in this sequence as a result of the deletion of the gene, the second nucleotide sequence can be placed adjacent this promoter. Alternatively, an appropriate viral promoter can first be attached to the second nucleotide sequence and this construct can then be inserted either into the first nucleotide sequence or adjacent thereto. In addition, the second nucleotide sequence can be inserted into and adjacent an altered coat protein coding sequence.

A double-stranded DNA of the chimeric nucleotide sequence or of a complementary copy of the chimeric nucleotide sequence is cloned into a production cell. If the viral nucleic acid is an RNA molecule, the chimeric nucleotide sequence is first attached to a promoter which is compatible with the production cell. The chimeric nucleotide sequence can then be cloned into any suitable vector which is compatible with the production cell. In his manner, only RNA copies of the chimeric nucleotide sequence are produced in the production cell. For example, if the production cell is *E., coli,* the lac promoter can be utilized. If the production cell is a plant cell, the CaMV promoter can be used. The production cell will be a eukaryotic cell such as yeast, plant or animal, if viral RNA must be capped for biological activity. The chimeric nucleotide sequence can then be-cloned into any suitable vector which is compatible with the production cell.

Alternatively, the chimeric nucleotide sequence is inserted in a vector adjacent a promoter which is compatible with the production cell. If the viral nucleic acid is a DNA molecule, it can be cloned directly into a production cell by attaching it to an origin of replication which is compatible with the production cell. In this manner, DNA copies of the chimeric nucleotide sequence are produced in the production cell.

In the case of alphaviruses, where the E1 and E2 glycoproteins and the coat protein are removed, a larger foreign protein coding sequence may be inserted to form the chimeric nucleotide sequence. The E1 and E2 glycoproteins do not have their own promoters, so the coat protein promoter would be used for a foreign coding sequence inserted in place of the adjacent coding sequences for the coat protein, E1 glycoprotein and E2 glycoprotein.

Alternatively, more than one foreign coding sequence may be inserted in place of the adjacent coding sequences for the coat protein, E1 glycoprotein and E1 glycoprotein. However, in this case, each foreign coding sequence would require its own appropriate viral promoter. However, the coat protein promoter could be used for one foreign coding sequence if that promoter had been preserved in the nucleotide sequence.

A double-stranded DNA of the recombinant plant viral nucleic acid or a complementary copy of the recombinant plant viral nucleic acid is cloned into a production cell. If the viral nucleic acid is an RNA molecule, the nucleic acid (cDNA) is first attached to a promoter which is compatible with the production cell. The RVNA can then be cloned into any suitable vector which is compatible with the production cell. In this manner, only RNA copies of the chimeric nucleotide sequence are produced in the production cell. For example, if the production cell is E. coli, the lac promoter can be utilized. If the production cell is a plant cell, the CaMV promoter can be used. The production cell can also be a eukaryotic cell such as yeast, plant or animal. Alternatively, the RVNA is inserted in a vector adjacent a promoter which is compatible with the production cell. If the viral nucleic acid is a DNA molecule, it can be cloned directly into a production cell by attaching it to an origin of replication which is compatible with the production cell. In this manner, DNA copies of the chimeric nucleotide sequence are produced in the production cell.

A promoter is a DNA sequence that directs RNA polymerase to bind to DNA and to initiate RNA synthesis. There are strong promoters and weak promoters. Among the strong promoters are lacuv5, trp, tac, trp-lacuv5, γp1, ompF, and bla. A useful promoter for expressing foreign genes in *E. coli* is one which is both strong and regulated. The γp1 promoter of bacteriophage γ is a strong, well-regulated promoter. Hedgpeth, J. M. et al., *Mol. Gen. Genet.* 163:197 (1978); Bernard, H. M. et al., *Gene* 5:59 (1979); Remaut, E. P. et al., *Gene* 15:81 (1981).

A gene encoding a temperature-sensitive γ repressor such as γcIts 857 may be included in the cloning vector. Bernard et al., *Gene* 5:59 (1979). At low temperature (31° C.), the $p_1$ promoter is maintained in a repressed state by the cI-gene product. Raising the temperature destroys the activity of the repressor. The $p_1$ promoter then directs the synthesis of large quantities of mRNA. In this way, *E. coli* production cells may grow to the desired concentration before producing the products encoded within the vectors. Similarly, a temperature-sensitive promoter may be activated at the desired time by adjusting the temperature of the culture.

It may be advantageous to assemble a plasmid that can conditionally attain very high copy numbers. For example, the pAS2 plasmid containing a lac or tac promoter will achieve very high copy numbers at 42° C. The lac repressor, present in the pAS2 plasmid, is then inactivated by isopropyl-β-D-thiogalactoside to allow synthesis of mRNA.

A further alternative when creating the RVNA is to prepare more than one nucleic acid (i.e., to prepare the nucleic acids necessary for a multipartite viral vector construct). In this case, each nucleic acid would require its own origin of assembly. Each nucleic acid could be prepared to contain a subgenomic promoter and a non-native nucleic acid.

If a multipartite virus were found to have the coding sequence for its coat protein on one strand of nucleic acid, and the coding sequence for a transmissibility factor on a different strand, then two chimeric nucleotide strands would be created in accordance with the invention. One foreign coding sequence would be inserted in place of the coat protein gene (or inserted next to the altered coat protein gene) on one strand of nucleic acid, and another foreign coding sequence would be inserted in place of the transmissibility factor gene (or inserted next to the altered transmissibility factor gene) on the other strand of nucleic acid.

Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription or expression of the non-native nucleic acid separate from the replication and translation of some of the coding sequences of the native nucleic acid. Each nucleic acid would have to have its own origin of assembly.

A third feature of the present invention is a virus or viral particle. The virus comprises a RVNA as described above which has been encapsidated. The resulting product is then capable of infecting an appropriate plant host. The RVNA sequence is transcribed and/or translated within the plant host to produce the desired product.

In one embodiment of the present invention, the recombinant plant viral nucleic acid is encapsidated by a heterologous capsid. Most commonly, this embodiment will make use of a rod-shaped capsid because of its ability to encapsidate a longer RVNA than the more geometrically constrained icosahedral capsid or spherical capsid. The use of a rod-shaped capsid permits incorporation of a larger non-native nucleic acid to form the RVNA. Such a rod-shaped capsid is most advantageous when more than one non-native nucleic acid is present in the RVNA.

Another feature of the invention is a vector containing the RVNA as described above. The RVNA is adjacent a nucleotide sequence selected from the group consisting of a production cell promoter or an origin of replication compatible with the production cell. The vector is utilized to transform a production cell which will then produce the RVNA in quantity. The production cell may be any cell which is compatible with the vector, and may be prokaryotic or eukaryotic. However, if the viral RNA (RVNA) must be capped in order to be active, the production cell must be capable of capping the viral RNA, such as a eukaryotic production cell.

A further feature of the present invention is a host which has been infected by the recombinant plant virus or viral nucleic acid. After introduction into a host, the host contains the RVNA which is capable of self-replication, encapsidation and systemic spread. The host can be infected with the recombinant virus by conventional techniques. Suitable techniques include, but are not limited to, leaf abrasion, abrasion in solution, high velocity water spray and other injury of a host as well as imbibing host seeds with water containing the recombinant virus. More specifically, suitable techniques include:

(a) Hand Inoculations. Hand inoculations of the encapsidated vector are performed using a neutral pH, low molarity phosphate buffer, with the addition of celite or carborundum (usually about 1%) One to four drops of the preparation is put onto the upper surface of a leaf and gently rubbed.

(b) Mechanized Inoculations of Plant Beds. Plant bed inoculations are performed by spraying ($CO_2$-propelled) the vector solution into a tractor-driven mower while cutting the leaves. Alternatively, the plant bed is mowed and the vector solution sprayed immediately onto the cut leaves.

(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

An alternative method for introducing a RVNA into a plant host is a technique known as agroinfection or Agrobacterium-mediated transformation (sometimes called Agro-infection) as described by Grimsley, N. et al., *Nature* 325:177 (1987). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a RVNA between the T-DNA border sequences results in transfer of the RVNA to the plant cells, where the RVNA is replicated, and then spreads systemically through the plant. Agro-infection has been accomplished with potato spindle tuber viroid (PSTV) (Gardner, R. C. et al., *Plant Mol. Biol.* 6:221 (1986)); CaV (Grimsley, N. et al., *Proc. Nat. Acad. Sci. USA* 83:3282 (1986)); MSV (Grimsley, N. et al., *Nature* 325:177 (1987) and Lazarowitz, S. C., *Nucl. Acids Res.* 16:229 (1988)), digitaria streak virus (Donson, J. et al., *Virology* 162:248 (1988)), wheat dwarf virus (Hayes, R. J. et al., *J. Gen. Virol.* 69:891 (1988)) and tomato golden mosaic virus (TGMV) (Elmer, J. S. et al., *Plant Mol. Biol.* 10:225 (1988) and Gardiner, W. E. et al., *EMBO J* 7:899 (1988)). Therefore, agro-infection of a susceptible plant could be accomplished with a virion containing a RVNA based on the nucleotide sequence of any of the above viruses.

A still further feature of the invention is a process for the production of a specified polypeptide or protein product such as, but not limited to, enzymes, complex biomolecules, a ribozyme, or polypeptide or protein products resulting from anti-sense RNA. Such products include, but not limited to: IL-1, IL-2, IL-3, . . . IL-12, etc.; EPO; CSF including G-CSF, GM-CSF, M-CSF, etc; Factor VIII; Factor IX; tPA; hGH; receptors and receptor antagonists; antibodies; neuro-polypeptides; melanin; insulin; vaccines and the like. The non-native nucleic acid of the RVNA comprises the transcribable sequence which leads to the production of the desired product. This process involves the infection of the appropriate host with a recombinant virus or recombinant viral nucleic acid such as those described above, the growth of the infected host to produce the desired product, and the isolation of the desired product, if necessary. The growth of the infected host is in accordance with conventional techniques, as is the isolation of the resultant product.

For example, a coding sequence for a protein such as neomycin phosphotransferase (NPTII) α-trichosanthin, rice α-amylase, human α-hemoglobin or human β-hemoglobin, is inserted adjacent the promoter of the TMV coat protein coding sequence, which has been deleted. In another example, a tyrosinase coding sequence such as isolated from Streptomyces antibioticus is inserted adjacent the same promoter of TMV, oat mosaic virus (OMV) or potyvirus rice necrosis virus (RNV). Recombinant virus can be prepared as described above, using the resulting recombinant viral nucleic acid. Tobacco or germinating barley is infected with the recombinant virus or recombinant plant viral nucleic acid. The viral nucleic acid self-replicates in the plant tissue to produce the enzymes amylase or tyrosinase. The activity of this tyrosinase leads to the production of melanin. See, for example, Huber, M. et al., Biochemistry 24:6038 (1985).

In a further example, a cyclodextrin glucanotransferase coding sequence, such as isolated from Bacillus sp. No. 17-1 (see U.S. Pat. No. 4,135,977) is inserted adjacent the promoter of the viral coat protein of a nucleotide sequence derived from OMV, or PVX in which the coat protein coding sequence has been removed, and which then contains a non-native promoter and coat protein gene. Corn or potato is infected with the appropriate recombinant virus or recombinant plant viral nucleic acid to produce the enzyme cyclodextrin glucotransferase. The activity of this enzyme leads to the production of cyclodextrin, which is useful as a flavorant or for drug delivery.

In some plants, the production of anti-sense RNA as a product can be useful to prevent the expression of certain phenotypic traits. Particularly, some plants produce substances which are abused as drugs (e. g., cocaine is derived from the coca plant, and tetrahydrocannabinol (THC) is the active substance of abuse derived from cannabis or marijuana plants). An anti-sense RNA complementary to the plant RNA necessary for the production of an abusable substance would prevent the production of the substance. This could prove to be an effective tool in reducing the supply of illegal drugs.

A still further feature of the invention is a process for the production of an enzyme suitable for the stereospecific catalysis of an organic compound. The non-native nucleic acid comprises the transcribable sequence which leads to the production of the desired product. This process involves the infection of the appropriate host with a recombinant virus or recombinant viral nucleic acid such as those described above, the growth of the infected host to produce the desired product and the isolation of the desired product. The growth of the infected host is in accordance with conventional techniques, as is the isolation of the resultant product. The stereospecific enzyme is then utilized to catalyze the desired reaction. One use of stereospecific enzymes is in the separation of racemate mixtures.

In one example, a suitable esterase or lipase coding sequence such as isolated from an appropriate microorganism is inserted adjacent the promoter of the viral coat protein of a nucleotide sequence derived from TMV, oat mosaic virus (OMV) or rice necrosis virus (RNV) in which the coat protein coding sequence has been removed and which then contains a non-native promoter and coat protein gene. Tobacco or germinating barley is infected with the recombinant virus or recombinant plant viral nucleic acid to produce the esterase or lipase enzyme. This enzyme is isolated and used in the stereospecific preparation of a compound such as naproxen, as described in EP-A 0233656 or EP-A 0227078.

An esterase coding sequence is isolated from the appropriate microorganism, such as *Bacillus subtilis, Bacillus licheniformis* (a sample of this species is deposited with the American Type Culture Collection, Rockville, Md. (ATCC) under Accession No. 11945), *Pseudomonas fluorescens, Pseudomonas putida* (a sample of this species is deposited with the Institute for Fermentation (IFO), Osaka, Japan, under Accession No. 12996), *Pseudomonas riboflavina* (a sample of this species is deposited with IFO under Accession No. 13584), *Pseudomonas ovalis* (a sample of this species is deposited with the Institute of Applied Microbiology (SAM), University of Tokyo, Japan, under Accession No. 1049), *Pseudomonas aeruainosa* (IFO 13130), *Mucor angulimacrosporus* (SAM 6149), *Arthrobacter paraffineus* (ATCC 21218), Strain is III-25 (CBS 666.86), Strain LK 3–4 (CBS 667.86), Strain Sp 4 (CBS 668.86), Strain Thai III 18-1 (CBS 669.86), and Strain Thai VI 12 (CBS 670.86). Advantageously, cultures of species *Bacillus subtilis* include cultures of species Bacillus species Thai 1–8 (CBS 679.85), species Bacillus species In IV-8 (CBS 680.85), species Bacillus species Nap 10-M (CBS 805.85), species Bacillus species Sp 111-4 (CBS 806.85), *Bacillus subtilis* 1–85 (Yuki, S. et al., *Japan J. Gen.* 42:251 (1967)), *Bacillus subtilis* 1–85/pNAPT-7 (CBS 673.86), *Bacillus subtilis* 1A-40/pNAPT-8 (CBS 674.86), and *Bacillus subtilis* 1A-40/pNAPT-7 (CBS 675.86). Advantageously, cultures of *Pseudomonas fluorescens* include a culture of species Pseudomonas species Kpr 1–6 (CBS 807.85), and *Pseudomonas fluorescens* species (IFO 3081).

A lipase coding sequence is isolated from the appropriate microorganism such as the genera *Candida, Rhizopus,*

*Mucor, Aspergilus, Penicillium, Pseudomonas, Chromobacterium,* and *Geotrichium.* Particularly preferred is the lipase of *Candida cylindracea* (Qu-Ming et al., Tetrahedron Letts. 27, 7 (1986)).

A fusion protein can be formed by incorporation of the non-native nucleic acid into a structural gene of the viral nucleic acid, e.g., the coat protein gene. The regulation sites on the viral structural gene remain functional. Thus, protein synthesis can occur in the usual way, from the starting codon for methionine to the stop codon on the foreign gene, to produce the fusion protein. The fusion protein contains at the amino terminal end a part or all of the viral structural protein, and contains at the carboxy terminal end the desired material, e.g., a stereospecific enzyme. For its subsequent use, the stereospecific enzyme must first be processed by a specific cleavage from this fusion protein and then further purified. A reaction with cyanogen bromide leads to a cleavage of the peptide sequence at the carboxy end of methionine residues (5.0. Needleman, "Protein Sequence Determination", Springer Publishers, 1970, N.Y.). Accordingly, it is necessary for this purpose that the second sequence contain an additional codon for methionine, whereby a methionine residue is disposed between the N-terminal native protein sequence and the C-terminal foreign protein of the fusion protein. However, this method fails if other methionine residues are present in the desired protein. Additionally, the cleavage with cyanogen bromide has the disadvantage of evoking secondary reactions at various other amino acids.

Alternatively, an oligonucleotide segment, referred to as a "linker," may be placed between the second sequence and the viral sequence. The linker codes for an amino acid sequence of the extended specific cleavage site of a proteolytic enzyme as well as a specific cleavage site (see, for example, U.S. Pat. Nos. 4,769,326 and 4,543,329). The use of linkers in the fusion protein at the amino terminal end of the non-native protein avoids the secondary reactions inherent in cyanogen bromide cleavage by a selective enzymatic hydrolysis. An example of such a linker is a tetrapeptide of the general formula Pro-Xaa-Gly-Pro(SEQ ID NO: 1) (amino-terminal end of non-native protein), wherein Xaa is any desired amino acid. The overall cleavage is effected by first selectively cleaving the xaa-Gly bond with a collagenase (E.C. 3.4.24.3., Clostridiopeptidase A) then removing the glycine residue with an aminoacyl-proline aminopeptidase (aminopeptidase-P, E.C. 3.4.11.9.) and removing the proline residue with a proline amino peptidase (E.C. 3.4.11.5). In the alternative, the aminopeptidase enzyme can be replaced by postproline dipeptidylaminopeptidase. Other linkers and appropriate enzymes are set forth in U.S. Pat. No. 4,769,326.

A still further feature of the invention is a process for the induction of male sterility in plants. Male sterility can be induced by several mechanisms, including, but not limited to, an anti-sense RNA mechanism, a ribozyme mechanism, or a protein mechanism which may induce male sterility or self-incompatibility or interfere with normal gametophytic development. The second nucleotide sequence of the chimeric nucleotide sequence comprises the transcribable sequence which leads to the induction of male sterility. This process involves the infection of the appropriate plant with a virus, such as those described above, and the growth of the infected plant to produce the desired male sterility. The growth of the infected plant is in accordance with conventional techniques.

Male sterility can be induced in plants by many mechanisms including, but not limited to (a) absence of pollen formation, (b) formation of infertile and/or non-functional pollen, (c) self-incompatibility, (d) inhibition of self-compatibility, (e) perturbation of mitochondrial function(s), (f) alteration of the production of a hormone or other biomolecule to interfere with normal gametophytic development, or (g) inhibition of a developmental gene necessary for normal male gametophytic tissue. These mechanisms may be accomplished by using anti-sense RNA, ribozymes, genes or protein products. The recombinant plant viral nucleic acids of the present invention contain one or more nucleotide sequences which function to induce male sterility in plants. To accomplish this function, the recombinant plant viral nucleic acids may contain a nucleotide sequence, a single gene or a series of genes.

Male sterility traits could be formed by isolating a nuclear-encoded male sterility gene. Many of these genes are known to be single genes. For example, Tanksley et al., *Hort Science* 23, 387 (1988), placed ms-10 in CIS with a rare allele of the tightly linked enzyme-coding gene Prx-2. The Prx-2 allele is codominant, allowing selection for heterozygous plants carrying the recessive ms-10 allele in backcross populations and eliminating the need for progeny testing during transfer of the gene into parents for hybrid production. A male-sterile anthocyaninless plant (ms-10 aa/ms-10aa) was crossed to a heterozygous, fertile plant in which a rare peroxidase allele was in cis with the recessive male-sterile allele (ms-10 Prx-2'/+Prx-2+). Male sterile plants were selected from the progeny (ms-10 Prx2'/ms-10aa). Once the male-sterile gene has been transferred into a prospective parental line, sterile plants can be selected at the seedling stage either from backcross or $F_2$ seed lots.

In pearl millet, recessive male sterile genes were found in vg 272 and IP 482. Male sterility in pearl millet line Vg 272 and in IP 482 is essentially controlled by a single recessive gene. Male sterility in Vg 272 is due to a recessive gene, ms, which has no effect on meiosis in pollen mother cells, but acts after separation of microspores from tetrads but before onset of the first mitotic division.

Dewey et al., *Cell* 4:439–449 (1986) isolated and characterized a 3547 bp fragment from male sterile (cms-T) maize mitochondria, designated TURF 243. TURF 243 contains two long open reading frames that could encode polypeptides of 12,961 Mr and 24,675 Mr. TURF 243 transcripts appeared to be uniquely altered in cms-T plants restored to fertility by the nuclear restorer genes Rf1 and Rf2. A fragment of maize mtDNA from T cytoplasm was characterized by nucleotide sequence analysis. To obtain isolation of nucleic acids, mitochondrial RNA (mtRNA), and mtDNA were prepared from six- to seven-day-old dark grown seedlings of *Zea Mays* L. by conventional techniques.

Another means by which male sterile traits could be formed is by the isolation of a male sterility gene from a virus. There are several viruses or virus-like particles that induce male sterility in plants. Recent work suggests that viroid-like agents in male sterile beets may occur. Pearson, O. N., *Hort. Science* 16:482 (1981). Cytoplasmic male sterility may be conditioned by a discrete particle such as a plasmid or an inclusion. Viruses are not seed transmitted with the regularity of cytosterile systems. Viroids can be transmitted through pollen. Transfer of a factor of some kind across a graft union has been demonstrated in petunia, beet, sunflower, and alfalfa. There is no direct effect on the fertility of the scion, but selfs or crosses by a maintainer on the grafted scion produced male sterile plants in the next generation. Cms beets grown at 36° C. for 6 weeks, then at 25° C., produced fertile plants from new shoots possibly due to elimination of "cytoplasmic spherical bodies", but progenies from the plants reverted to sterility after three generations at normal growing conditions. Cytoplasmic male sterility in the broad bean plant (*Vicia fabal*) was found to be caused by the presence of virus or virus-like particles. Possibly a case similar to a cms-system occurs in garlic. Pollen degeneration typical of sporophytic cms plants was found, but electron microscope studies showed richettsia-like inclusions in the anthers, which could be eliminated with antibiotics, causing the pollen to become fertile. Konvicha et al., *Z. Pfanzenzychtung* 80:265 (1978).

Male sterile traits could be formed by a third method of introducing an altered protein, using a transit peptide sequence so that it will be transported into the mitochondria, and perturbing the mitochondrial functions. This protein could work to overwhelm normal mitochondrial function or reduce a metabolite required in a vital pathway. It is widely believed that slight perturbations in the mitochondria will lead to male sterility. Remy et al., *Theor. Appl. Genet.* 64:249 (1983) conducted a two dimensional analysis of chloroplast proteins from normal and cytoplasmic male-sterile *B. napus* lines. Chloroplast and mitochondrial DNAs of N and cms lines of *B. napus* were characterized and compared using restriction enzyme analysis. Identical restriction patterns were found for chloroplastic DNAs from the cms *B. napus* lines and the cms lines of the Japanese radish used to transfer the cms trait into *B. napus*. In Remy's study, chloroplast proteins from stroma and thylakoids of N and cms lines of *B. napus* were characterized and compared using a 2-D polyacrylamide gel separation. It was shown that (1) stromal compartments of the two lines were very similar, and (2) the lines could be distinguished by the spots corresponding to the β subunits of coupling factor CP, from the ATPase complex.

A fourth method for inducing male sterility in plants is by inducing or inhibiting a hormone that will alter normal gametophytic development—for example, inhibiting the production of gibberellic acid prior to or at the flowering stage to disturb pollen formation, or modifying production of ethylene prior to or at the flowering stage to alter flower formation and/or sex expression.

A fifth method for inducing male sterility in plants is by inhibiting a developmental gene required for the normal male gametophytic tissue, for example, using anti-sense RNA that is complementary to the developmental signal RNA or mRNA. Padmaja et al., *Cytologia* 53:585 (1988) discusses cytogenetical investigations on a spontaneous male-sterile mutant isolated from the Petunia inbred lines. Male sterility was found to be associated with atypical behavior of tapetum, characterized by prolonged nuclear divisions and untimely degeneration as a result of conversion from glandular to periplasmodial type.

A sixth method for inducing male sterility in plants is by isolating a self-incompatibility gene and using the gene in the vector of the present invention. Self-incompatibility (S) gene systems that encourage out-breeding are present in more than 50% of the angiosperm plant families. Ebert, et al., *Cell* 56:255 (1989). Multiple S gene systems are known in some species. In several systems, abundant style glycoproteins (S glycoproteins) have been identified. These glycoproteins are polymorphic and can be correlated with identified S alleles. S genes, corresponding to the style glycoproteins of *N. alaba* and *B. oleraceae* have been cloned and sequenced. Amino acid substitutions and deletions/insertions, although present throughout the sequences, tend to be clustered in regions of hypervariability that are likely to encode allelic specificity.

A seventh method for inducing male sterility in plants is by blocking self incompatibility, by the engineering of a protein that will bind and inactivate the compatibility site or by turning off self-compatibility, by the engineering of an antisense RNA that will bind with the mRNA to a self-compatibility protein.

Specific effects resulting in male sterility can range from the early stages of sporogenous cell formation right through to a condition in which anthers containing viable pollen do not dehisce. Some or all of the developmental stages within this range may be affected. Some of the more obvious specific effects include, the following examples:

1) Meiosis is disrupted, leading to degeneration of the pollen mother cells or early microspores in which case pollen aborts and anther development is arrested at an early stage.

2) Exine formation is disrupted and microspores are thin-walled, perhaps distorted in shape, and nonviable. Anthers are generally more developed than the exines, but still not normal.

3) Microspore vacuole abnormalities, decreased starch deposition and tapetum persistence are evident. Pollen is nonviable and anthers are still not normal.

4) Pollen is present and viable, and anthers appear normal but either do not dehisce or show much delayed dehiscence.

5) Self incompatibility mechanisms disrupt or prevent enzymatic digestion of the style by the pollen grain.

Male sterility in plants may be induced by the mechanisms listed above at any stage prior to pollen shed. The male sterility mechanism selected may be applied to plants in the field (or in the greenhouse) at any time after seedling emergence and before pollen shed. The exact time of application will depend on the male sterility mechanism used and the optimum effectiveness in producing male sterile plants.

EXAMPLES

In the following examples, enzyme reactions were conducted in accordance with manufacturers recommended procedures, unless otherwise indicated. Standard techniques, such as those described in Maniatis, T. et al., *Molecular Cloning* (1st Ed.) and Sambrook, J. et al. (2nd Ed.), Cold Spring Harbor Laboratory, Cold Spring Harbor (1982, 1989), *Meth.in Enzymol.*, Vols. 68, 100, 101, 188 and 152–155 (1979, 1983, 1986 and 1987) and DNA Cloning, D. M. Clover, Ed., IRL Press, Oxford (1985), were utilized for vector constructions and transformation unless otherwise specified.

Comparative Examples

The following comparative examples demonstrate either the instability of prior art recombinant viral nucleic acid during systemic infection of host plants or the inability to systemically infect plants and to efficiently produce the product of the inserted nonnative gene.

Comparative Example 1

Recombinant plant viral nucleic acid was prepared by inserting the chloramphenical acetyltransferase (CAT) gene which had been fused behind a TMV subgenomic RNA promoter between the 30K and coat protein genes of TMV. pTMV-CAT-CP was prepared as described by Dawson, W. O. et al., *Virology* 172:285–292 (1989). Briefly, pTMV-CAT-CP was constructed by cutting pTMV204, a full-genomic cDNA clone of TMV strain U1, Dawson, W. O. et al., *Proc. Nat. Acad. Sci. USA* 83:1832 (1986), with NcoI (nt. 5460), blunting with Klenow fragment of DNA polymerase I, adding PstI linkers (CCTGCACG from Boehringer- Mannheim Biochemicals), excising with PstI and NsiI (nt. 6207), and ligating this 747-bp fragment into the NsiI site (nt. 6207) of pTMV-S3-CAT-28, a modified TMV with the CAT ORF substituted for the coat protein ORF. Dawson, W. O. et al., *Phytopathology* 78:783 (1988). TMV nucleotide numbering is that of Goelet, P. et al., *Proc. Nat. Acad. Sci. USA* 79:5818 (1982). Correct ligation and orientation of each construct were checked by restriction mapping and sequencing.

Inoculations. In vitro transcription of plasmid DNA constructs and inoculation procedures were as described previously. Ahlquist, P. and M. Janda, *Mol. Cell Biol.* 4:2876 (1984). Virus was propagated systemically in Xanthi tobacco (*Nicotiana tabacum* L.) and *Nicotiana svlvestris:* Xanthi-nc tobacco was used as a local lesion host. Plants were grown in a greenhouse prior to inoculations and then subsequently maintained in plant growth chambers at 25° with a 16-hour photoperiod of approximately 2000 1x.

CAT Assays. Amounts of CAT activity were assayed essentially by the procedures described, Shaw, W. V., *Meth. Enzymology* 53:737 (1975), 200 mg of leaf tissue were macerated in assay buffer followed by addition of 0.5 mM acetyl CoA and 0.1 $\mu$Ci [$^{14}$C]-chloramphenicol, incubation for 45 minutes at 37°, extraction and resolution by thin-layer chromatography, and finally autoradiography.

RNA Analysis. Four days after inoculation, total RNA from infected leaves was extracted as described (47a). For blot hybridization analysis, RNA was electrophoresed in 1.2% agarose gels, transferred to nitrocellulose, and hybridized with nick-translated cDNA of TMV (nts. 5080–6395) in pUC119 or pCM1 (Pharmacia) which contains the CAT ORF. Total RNA from infected leaves also was analyzed by RNase protection assays for wild-type sequences essentially as described in Ausubel, F. M. et al., *Current Protocols in Mol. Biol.*, Wiley, N.Y. (1987). The 3' half (BamHI:nt. 3332-PstI:nt. 6401) of pTMV204 was cloned into pT7/T3-19 (from BRL). After EcoRI digestion (nt. 4254), $^{32}$P-labeled transcripts complementary to the 3' viral sequencs were produced with T7 RNA polymerase. An excess amount of the probe was hybridized to RNA samples, treated with 40 $\mu$g/ml RNase A (Sigma) and 300 U RNase T1 (BRL) extracted, denatured with DMSO and glyoxal, and electrophoresed in 1.2% agarose gels which were subsequently dried and exposed to Kodak X-ray film.

Construction of cDNA Clones of ProgenY Virus. RNA was extracted from purified virions and cDNA was prepared as previously described, Dawson, W. O. et al., *Proc. Nat. Acad. Sci. USA* 83:1832 (1986). Double-stranded cDNA was digested with BamHI (nt. 3332) and SacI (nt. 6142) and cloned into BamHI- and SacI-digested pUC19. Nucleotide sequencing of DNA was by the dideoxynucleotide chain terminating procedure. Zagursky, R. et al., *Gene Anal. Tech.* 2:89 (1985).

Results. In vitro transcripts of pTMC-CAT-CP, which had the CAT cartridge inserted upstream of the coat protein gene, resulted in CAT-CP, a hybrid virus 7452 nucleotides in length and a gene order of 126K, 183K, 30K, CAT and coat protein. In vitro transcripts were used to inoculate leaves of *N. tabacum* L. varieties Xanthi and Xanthi-nc and *N. svlvestris*. Results were compared to those from plants infected with wild-type virus, TMV 204, or the 15 free-RNA virus, S3-CAT-28, that expresses CAT as a replacement for coat protein, Dawson, W. O. et al., Phytonatholoqy 78:783 (1988), CAT-CP replicated effectively and moved from cell to cell in inoculated leaves similarly to TMV 204. Necrotic lesions developed on Xanthi-nc tobacco at approximately the same time and were of the same size as those caused by TMV 204 and S3-CAT-2B. CAT-CP induced no symptoms in inoculated leaves of the systemic hosts, Xanthi tobacco and *N. sylvestris,* but produced mosaic symptoms in developing leaves similar to those produced by TMV 204. The concentration of virions in cells infected with CAT-CP, estimated by yields obtained after virion purification and by transmission electron microscopy of thin sections of inoculated leaves, appeared to be approximately equal to that from a TMV 204 infection.

CAT-CP is 7452 nucleotides long, compared to 6395 nucleotides for TMV 204, whit would result in CAT-CP virions 350 nm in length, compared to the 300 nm virions of wild-type TMV. Virus was purified from inoculated leaves of CAT-CP-infected plants and analyzed by transmission electron microscopy. Most of the virions from the CAT-CP infections were 350 nm in length. One problem in assessing the length of virions of TMV UI viewed by electron microscopy is that preparations normally contain fragmented and end-to-end aggregated virions in addition to individual genomic-length virions. To determine the proportion of 350- to 300-nm virions, distinct, individual virions of each size were counted. The ratio of 350/300 nm virions in leaves inoculated with CAT-CP was 191:21, compared to 12:253 from the wild-type infection. The 350-nm virions in wild-type TMV infection probably resulted from the end-to-end aggregation of fragmented virions, since TMV UI has a propensity to aggregate end-to-end and all length virions can be found. These data suggest that the extra gene of CAT-CP was maintained and encapsidated in these inoculated leaves.

CAT activity was detected in leaves inoculated with CAT-CP using in vitro RNA transcripts or the subsequent first or second passage local lesions. From more than one hundred samples assayed, a range of variation was found among different positive samples. Similar levels of CAT were found in CATCP-infected leaves as those infected with the coat protein-less mutant, S3-CAT-2 B. Only background amounts were detected in TMV 204-infected or healthy leaves.

The host range of CAT-CP was compared to that of wild-type TMV by inoculating a series of hosts known to support replication of TMV and by screening for CAT activity. CAT activity was detected in inoculated leaves of *Zinnia eleaans* Jacq., *Lunaria annua* L., *Beta vulaaris* L., *Calendula officinalis* L., and *Spinacia oleracea* L., which represent three plant families in addition to the Solanaceae. This indicated that this alteration of the TMV genome did not appear to alter the host range.

In order to determine whether CAT-CP produced an additional subgenomic RNA as a result of the inserted sequences, total RNA from infected leaves was extracted and compared to that of wild-type TMV by blot hybridization analysis, using a TMV or a CAT DNA probe. Xanthi tobacco leaves infected with CAT-CP previously passaged twice in xanthi-nc tobacco were chosen because they contained a population of CAT-CP and progeny virus with deletions to be compared to wild-type TMV. Two distinct genomic RNAs were detected. The largest hybridized to both TMV and CAT probes, whereas the smaller genomic RNA hybridized only to the TMV probe and comigrated with wild-type Tv genomic RNA. Three distinct, small RNAs were found in RNA from CAT-CP-infected leaves, compared to two from TMV 204-infected leaves. The smaller RNAs that comigrated with the subgenomic messages for the coat and 30K proteins of wild-type TMV hybridized only to the Tv-specific probe. A larger subgenomic RNA from CAT-CP-infected leaves hybridized to both the CAT and TMV probes. Assuming that as for the subgenomic mRNAs of wild-type TMV, this larger subgenomic RNA is 3' coterminal with the genomic RNA, Goelet, P. and Karn, J., *J. Mol. Biol.* 154:541 (1982), these results are consistent with the extra CAT-CP mRNA predicted for expression of CAT. The putative CAT-CP subgenomic RNA for 30K protein, containing the 30K, CAT, and coat protein ORFs was not observed, possibly because bands in the region between 2.4 and 4.4 kb were obscured by viral RNAs adhering during electrophoresis to host rRNAs and were difficult to resolve (Goelet, P. and Karn, J., *J. Mol. Biol.* 154:541 (1982); Dougherty, W. G., *Virology* 131:473 (1983)).

The amounts of CAT activity in upper, systemically infected leaves were variable and much lower than in inoculated leaves, and in many cases none was detected. Hybridizations with Tv and CAT probes demonstrated that the proportion of virus-retaining CAT sequences was quickly reduced to undetectable levels. The transition from CAT-CP to a population of virus with the inserted CAT ORF deleted occurred during systemic invasion of the plant and sometimes in inoculated leaves. In contrast, CAT sequences and CAT activity often were detected in leaves inoculated with virus that had been passaged through single lesions three or four times.

CAT-CP virions were examined from systemically infected Xanthi tobacco leaves approximately 30days after inoculation. Quantification of virions from the uppermost leaves of the plants infected with CATCP produced a ratio of 350-/300-nm virions of 78:716. This was compared to a ratio of 191:21 in inoculated leaves, indicating that the major component of the population shifted to 300-nm virions during systemic infection. The deleted progeny virus recovered after continued replication of CAT-CP was identical in host range and symptomatology to wild-type TMV.

cDNA of the region that encompassed the CAT insertion (nts. 3332–6142) was cloned from the progeny CAT-CP virion RNA from systemically infected Xanthi leaves to sample the virus population. Characterization of nine cDNA clones by size and restriction mapping indicated that eight were identical with wild-type TMV.

One cDNA clone appeared to be the size predicted for the CAT-CP construct, but the restriction map varied from that predicted for CAT-CP. Five clones that were evaluated by size and restriction analysis as wild-type were sequenced through the region of the CAT insertion and also through a portion of the coat protein gene, and found to be identical to the parental wild-type virus. This suggested the inserted sequences could be excised, giving rise to wild-type TMV.

To corroborate this possible excision, samples of the total leaf RNA used in the blot hybridization analysis were analyzed by RNase protection assays using T7-produced minus-strand RNA complementary to in inoculated leaves. In contrast, CAT sequences and CAT activity often were detected in leaves inoculated with virus that had been passaged through single lesions three or four times.

CAT-CP virions were examined from systemically infected Xanthi tobacco leaves approximately 30 days after inoculation. Quantification of virions from the uppermost leaves of the plants infected with CATCP produced a ratio of 350-/300-nm virions of 78:716. This was compared to a ratio of 191:21 in inoculated leaves, indicating that the major component of the population shifted to 300-nm virions during systemic infection. The deleted progeny virus recovered after continued replication of CAT-CP was identical in host range and symptomatology to wild-type TMV.

cDNA of the region that encompassed the CAT insertion (nts. 3332–6142) was cloned from the progeny CAT-CP virion RNA from systemically infected Xanthi leaves to sample the virus population. Characterization of nine cDNA clones by size and restriction mapping indicated that eight were identical with wild-type TMV.

One cDNA clone appeared to be the size predicted for the CAT-CP construct, but the restriction map varied from that predicted for CAT-CP. Five clones that were evaluated by size and restriction analysis as wild-type were sequenced through the region of the CAT insertion and also through a portion of the coat protein gene, and found to be identical to the parental wild-type virus. This suggested the inserted sequences could be excised, giving rise to wild-type TMV.

To corroborate this possible excision, samples of the total leaf RNA used in the blot hybridization analysis were analyzed by RNase protection assays using T7-produced minus-strand RNA complementary to nucleotides 4254–6395 of wild-type TMV. The presence of wild-type sequences in this region would result in a protected RNA of 2140 nucleotides. A band this size from the CAT-CP RNAs comigrated with a similar band produced suing wild-type RNA to protect the probe. These data confirmed that the inserted sequences of CAT-CP could be precisely deleted. Taking into consideration the presence of repeated sequences in CAT-CP RNA that allow the bulge loop in the hybrid between CAT-CP and the wild-type TMV probe RNA to occur over a range of positions within the repeats, the RNase protection of wild-type probe by CAT-CP RNA should produce sets of bands that would fall within two nucleotide size ranges, 683–935 and 1202–1458. The other two major bands seen are of these sizes, corroborating the presence of CAT-CP RNA in these samples.

The loss of the inserted sequences of CAT-CP appeared to be due to two sequential processes. First was the loss of inserted sequences in individual molecules, as shown by the sequence analysis of cDNA clones of progeny virus. Since the deletion occurred between repeated sequences, it is possible that this occurred by homologous recombination as described for other plus-sense RNA viruses (Kirkegaard, K. and Baltimore, D., *Cell* 47:433 (1986); Bujarski, J. and Kaesberg, P., *Nature* 321:528 (1986); King, A. M. Q., in *RNA Genetics*, E. Domingo et al., Eds., Vol. II, 149–165, CRC Press, Inc., Boca Raton, Fla. (1988)) The second process resulted in a selected shift in the virus population. The RNase protection assays, in which the virus population was sampled, demonstrated that both CAT-CP and wild-type virus could be components of the population in inoculated leaves. The lack of CAT-CP in systemically infected leaves was probably due to a shift in the virus population, possibly because the original hybrid could not effectively compete with the deleted progeny wild-type virus in terms of replication and systemic movement.

Comparative Example 2

A recombinant plant viral nucleic acid was prepared by inserting the CAT gene which had been fused behind a TMV subgenomic RNA promoter between the coat protein gene and the nontranslated 3' region of TMV. pTMV-CP-CAT was prepared as described by Dawson et al. (II) Briefly, pTMV-CP-CAT was constructed by cutting pTMV-S3-CAT-28 with HindIII (nt. 5081), blunting with Klenow fragment of DNA polymerase I, adding PstI and NsiI (nt. 6207), and ligating this 1434-bp fragment in the NsiI site (nt. 6207) of pTMV204. Correct ligation and orientation of each construct were checked by restriction mapping and sequencing.

Plant inoculations, CAT assays, RNA analysis and construction of cDNA clones of progeny were performed as described in Comparative Example I. pTMV-CP-CAT, the larger hybrid virus construct, contained a 628-nucleotide repeat of that portion of the 30K gene containing the coat protein subgenomic promoter and the origin of assembly. This construct should produce a virus, CP-CAT, 7822 nt long with a gene order of 126K, 183K, 30K, coat protein, and CAT. CP-CAT replicated poorly. It produced necrotic lesions in Xanthi-nc that were small, approximately one-half the diameter of wild-type virus lesions, and their appearance was delayed by two days. Transmissibility of CP-CAT from these lesions was at a level approximately one-hundredth that of CAT-CP or wild-type TMV. No systemic symptoms appeared in Xanthi or N. sylvestri plants and the virus infection was transferrable only from inoculated leaves. Low but reproducible levels of CAT activity were found in CP-CAT-infected leaves. Since the replication of this chimeric virus was so impaired, characterization did not proceed any further.

In contrast to CAT-CP, when CP-CAT was allowed to replicate for extended periods in the systemic hosts, no wild-type-like virus symptoms ever were observed in upper leaves of plants and virus was never recovered from them, suggesting that this hybrid virus did not delete the inserted sequences in a manner to create a wild-type-like virus.

Comparative Example 3

A full-length DNA copy of the TMV genome is prepared and inserted into the PSTI site of pBR322 as described by Dawson, W. O. et al. (t). The viral coat protein gene is located at position 5711 of the TMV genome adjacent the 30k protein gene. The vector containing the DNA copy of the TMV genome is digested with the appropriate restriction enzymes and exonucleases to delete the coat protein coding sequence. For example, the coat protein coding sequence removed by partial digestion with ClaI and NsiI, followed by religation to reattach teh 3'-tail of the virus. Alternatively, the vector is cut at the 3' end of the viral nucleic acid. The viral DNA is removed by digestion with Bal31 or exonuclease III up through the start codon of the coat protein coding sequence. A synthetic DNA sequence containing the sequence of the viral 3'-tail is then ligated to the remaining 5'-end. The deletion of the coding sequence for the viral coat protein is confirmed by isolating TMV RNA and using it to infect tobacco plants. The isolated TMV RNA is found to be non-infective under natural conditions.

The 314-bp Sau3A fragment ($NH_2$ terminus of the Tn5 NPTII gene) from pNEO was filled in with Klenow polymerase and ligated to SalI (pd[GGTCGACC]) linkers. It was then digested with SalI and PstI and inserted into PstI/SalI-digested pUC128, Keen, N. T. et al., Gene 70:191 (1988), to give pNU10. The pNEO plasmid was digested with AsuII, filled in with Klenow polymerase and ligated to XhoI linkers (pd[CCTCGAGG]) to give pNX1. The pNX1 was digested with XhoI, filled in with Klenow polymerase, digested with PstI and ligated into PstI/SmaI-digested pNU10 to give pNU116.

The Xho/SalI fragment from pNU116 (NPTII sequences) is ligated adjacent the coat protein promoter. The resultant RVNA containing the NPTII gene insert was applied to twelve *Nicotiana tabacum* (cv. Xanthinc), a cultivar that has been backcrossed to contain the N gene for TMV resistance and to twelve *N. tabacum* (cv, Xanthi), a cultivar that does not contain the N gene. In both tobacco cultivars, no systemic spread was observed in any inoculated plant. The *N. tabacum* (cv. Xanthinc) showed the characteristic flecking spots on the inoculate leaf indicating resistance to the virus. The *N. tabacum* (cv. Xanthi) exhibited no flecking or systemic symptoms.

Comparative Example 4

A recombinant plant viral nucleic acid containing the NPTII coding sequence was prepared as described in Comparative Examples 1 and 3. The NPTII and coat protein coding sequences were each adjacent an "O" coat protein promoter. The presence of the coat protein gene should render the vector capable of being systemically spread.

The resultant RFVNA containing the NPTII-inserted gene was inoculated on twelve *N. tabacum* (cv. Xanthinc) and twelve *N. tabacum* (cv. Xanthinc) showed the flecking in each of the twelve plants, as with Comparative Example 1. The *N. tabacum* (cv. Xanthinc) plants showed systemic spread of the vector in all twelve plants.

Leaf discs from *N. tabacum* (cv. Xanthi) leaves were cultured on media containing kanamycin. None of the tissue survived in culture, indicating a loss or disfunction of the NFTII gene. Subsequent electron photomicroscopy of the present vector containing the NPTII gene recovered from the leaves of treated *N. tabacum* (cv. Xanthinc) plants showed that the present vector had lost a section of the vector corresponding to the NPTII gene, indicating a breakage and recombination of the vector.

Examples of the Preferred Embodiments

The following examples further illustrate the present invention. These examples are intended merely to be illustrative of the present invention and are not to be construed as being limited.

Example 1

Construction of Bacterial Plasmids. Numbers in parentheses refer to the TMV-U1 sequence. Goelet, P. et al., *Proc. Nat. Acad. Sci. USA* 79:5818 (1982). DNA manipulations were performed essentially as described in Ausubel, F. M. et al., *Current Protocols in Mol. Biol.*, Wiley, N.Y. (1987). All plasmids were propagated in *E. coli* strain JM109 except for pTBN62 (DH5α; Gibco BRL; and H8101).

pTKU1 (Fia. 1). The 7.3 kb pTMV204, Dawson, W. O. et al., *Proc. Nat. Acad. Sci. USA* 83:1832 (1986), PstI fragment (TMV-U1 genome and λ phage promoter from pPM1, Ahlquist, P. and M. Janda, *Mol. Cell Biol.* 4:2876 (1984), was subcloned into pUC19 to give pTP5. pTMV204 ApaI fragment (5455–6389) was ligated to oligonucleotides pd[CAGGTACCC] and d[GGGTACCTGGGCC], (SEQ ID No: 2), digested with KpnI (underlined within nucleotide sequence) and NcoI (5459) and ligated into NcoI/KpnI digested pTP5 to produce pTPK10. pTKU1 was constructed by subcloning the 7.3 kb PstI/KpnI fragment from pTPK10 into PstI/KpnI-digested pUC118. pTKU1 contained a DNA copy of the entire TMV-VI genome downstream of the λ phage promoter from pPMl. KpnI digestion and in vitro transcription of pTKUI gave infectious TMV RNA. pTKUI was constructed because PstI sites in the odotoglossum ring spot virus (ORSV, sometimes referred to as TMV-O) coat protein, DHFR and NFTII ORFs prohibited the use of this restriction enzyme (employed to linearize pTMV204; 4) to digest plasmid DNA of the hybrid constructs and produce infectious in vitro transcripts.

pTB2 (FIG. 1). pTMVS3-28, Dawson, W. O. et al., *Phytopathology* 78:783 (1988), was a derivative of pTMV204 in which the coat protein initiation codon was mutated to ACG and a XhoI site replaced the entire coat protein coding sequence. The 1.9 kb NcoI/SalI fragment (5459-SaI1 site in p8R322) from pTMVS3-28 was ligated into NcoI/SalI-digested pNEO, Beck, E. et al., Gene 19:327 (1982), to give pNS283. pBabsI was a 2.4 kb EcoRI cDNA clone from ORSV virion RNA with nucleotide, ORF and amino acid sequence similarities to TMV-UI (nts 4254–6370). A 680 bp pBabs1 HincII/EarI (Klenow polymerase infilled) fragment (containing the ORSV coat protein ORF and 203 bases upstream of its AUG) as ligated into the NstI site (6202; blunt-ended with T4 DNA polymerase) of pNS283 to produce pB31. The NcoI/SalI fragment from p831 was then ligated into the NcoI/SalI-digested pTMV204 (replacing the corresponding wild-type fragment 5459-Sal1site in pBR322) to give pTB281. pTB2 was constructed by ligating the BamHI/SplI fragment from pTB281 into BamHI/SplI-digested pTKU1 (replacing the corresponding wild-type fragment 3332–6245).

pNC4X, Brisson. N. et al., Nature 3 10:511 (1984). pNC4X consisted of the R67 DHFR gene cloned into pUC8X. The plasmid contained a XhoI site eight bases upstream of the initiation codon for the DHFR gene. In addition, the stop codon and five bases of carboxy-terminal DHFR sequence were deleted and replaced by a SalI site.

pNU116. A 315 bp pNE0 Sau3S (Klenow polymerase infilled) fragment ($NH_2$, terminus of Tn5 NPTII gene) was ligated to Sal1 (pd [GGTCGACC] linkers, SalI/FstI digested, and inserted into FstI/Sal-digested pUC128, Keen, N. T. et al., Gene 70:191 (1988), to give pNU10. pNE0 was digested with AsuII, infilled with Klenow polymerase and ligated to XhoI linkers (pd[CCTCGAGG]) to generate pNX1. pNUII6 was constructed by digesting pNX1 with Xho1, infilling with Klenow polymerase, digesting with PstI and ligating the resulting 632 bp fragment (COOH terminus of the Tn5 NPTII gene) into PstI/SmaI-digested pNU10. This manipulation of the NPTII gene removed an additional ATG codon 16 bases upstream of the initiation codon, the presence of which decreased NPTII activity in transformed plant cells. Rogers, S. G. et al., Plant Mol. Biol. Rep, 3:111 (1985).

pTBD4 and pTBN62 (Fia. 1). XhoI/SalI fragments from pNC4X (DHFR sequence) and pNU116 (NPTII sequence) respectively were ligated into the Xho1 site of PTB2 in the same sense as the TMV coding sequences.

In Vitro Transcription and Inoculation of Plants. Plants grown as in Dawson, W. O. et al., Phytonathology 78:783 (1988), were inoculated with in vitro transcripts TB2 (nt. 6602), pTBD4 (nt. 6840) and TBN62 (nt. 7434) from Kpn1 digested pTBD2, pTBD4 and pTBN62, respectively. The in vitro transcription method was as previously described.

Analysis of Progeny Virion RNA. Virus purification was essentially as described by Gooding Jr., G. V. and Herbert T. T., Phytopathology 57:1285 (1967), with one precipitation with polyethylene glycol (8% PEG, 0.1M NaCl; 0° C. 1 hr) and one ultracentrifugation (151,000–235,000×g; 90 min). Virion RNA was extracted by digesting 1 mg virus with 0.2 $\mu$g Froteinase K in 10 mM Tris HCl, pH 7.5, 1 mM EDTA, 0.1%. SDS at 37° C. for 1 hr, followed by phenol/chloroform extractions. RNA samples were DMSO-denatured, glyoxalated, electrophoresed in 1% agarose gels and transferred to nitrocellulose (pore size 0.45 $\mu$m; Schleicher and Schull; Ausubel, F. M. et al., Current Protocols in Mol. Biol., Wiley, N.Y. (1987). The transfers were probed with [$\alpha^{-35}$S]-dATP (New England Nuclear) labelled, Goelet, P. and Karn, J., J. Mol. Biol. 154:541 (1982), restriction fragments. RNase protection assays were as described in Ausubel, F. M. et al., Current Protocols in Mol. Biol., Wiley, N.Y. (1987). TBD4-38 and pTBN62-38 contained BamHI/KpnI fragments (nts. 3332–6396) from pTBD4 and pTBN62, respectively, cloned into BamHI/KpnI-digested pBluescript SKI⁻ (Stratagene).

Immunological Detection of NPTII. Sample preparation and Western analysis were as described previously. Dawson, W. O. et al., Phytopathology 78:783 (1988). Leaf samples were ground in liquid $N_2$ and extraction buffer (10% glycerol, 62.5 mM Tris HCl pH 7, 5% mercaptoethanol, 5 mM phenylmethylsulfonyl fluoride). Equivalent protein concentrations were determined and absolute concentrations estimated by Bradford assey (Strategene; Bradford, M. M., Anal. Biochem. 72:248 (1976)), with bovine serum albumin as standard. Western transfers were probed with antiserum to NPTII (1:500; 5 Prime, 3 Prime, Inc.) and then with alkaline phosphatase-conjugated goad anti-rabbit IgG (1:1000).

NFII Activity Assavs. NPTII activity was detected by its phosphorylation of neomycin sulphate. Enzyme assays were as described in McDonnell, R. E. et al., Plant Mol. Biol. Rep. 5:380 (1987) except the extraction buffer was as described above and dilution series of purified NPTII (5 Prime, 3 Prime, Inc.) in healthy tissue were included.

Leaf Disc Assays to Screen for Resistance to Kanamycin Sulphate. NPTII confers resistance to the aminoglycoside kanamycin. Beck, E. et al., Gene 19:327 (1982). Young systemic leaves 12 days post-inoculation were surface-sterilized and washed in approximately 0.01% Tween 20 (5 min), 0.25% sodium hypochlorite (2 min), 70% ethanol (30 sec), distilled water (4×10 sec). Leaf discs were cut from a leaf in pairs; one was placed on Murashige and Skoog (MS) medium alone and the other on kanamycin sulphate-supplemented MS medium. Plates were incubated at 32° C. with a photoperiod of 16 hours. Leaf discs were transferred to freshly prepared medium every seven days.

Mechanical inoculation of N. benthamiana plants with in vitro transcripts derived from DNA constructs pTB2, pTBD4 and pTBN62, respectively, resulted in symptomatic infection with virus of typical TMV shape and yield (1.5–5.8 mg virus/g tissue). Symptoms were less severe compared to TMV-UI-infected plants and consisted of plant stunting with mild chlorosis and distortion of systemic leaves. The sizes of virion RNA from systemically infected tissue of plants inoculated with TB2, TBD4 and TBN62, respectively, were consistent with predicted lengths of RNA transcribed in vitro from the respective plasmids. These RNA species contained TMV sequences plus their respective bacterial gene inserts. Probes complementary to the manipulated portion of the respective genomes were protected in RNase protection assays by progeny TBD4 and TBN62 viral RNAs. This indicated that the precise and rapid deletion of inserted sequences which had been a problem with previous constructs, Dawson, W. O. et al., Virology 172:285–292 (1989), did not occur with TBD4 or TBN62. It was hypothesized that with the prevously reported constructs, foreign inserts were deleted due to recombination between repeated subgenomic promoter sequences, Dawson, W. O. et al., Virology 172:285–292 (1989). With TBD4 and TBN62, such repeated sequences were reduced by employing heterologous subgenomic mRNA promoters. Additional bands that were seen and were smaller than the probe and smaller than the full-length viral RNA might represent alterations within a portion of the TBN62 population, although in this case the relative proportion of full-length and additional smaller bands was unchanged following a subsequent passage.

The sequence stability of TBD4 and TBN62 virion RNA was examined in serial passages through N. benthamiana.

Plants were inoculated with two and four independent in vitro transcript ion reactions from pTBD4 and pTBN62, respectively, and systemically infected leaf tissue was serially passaged every 11–12 days. After 48 days of systemic infection, full-length virion RNA of TBD4 including the DHFR sequences was still detected by Northern transfer hybridization, and still protected probes complementary to the manipulated portion of the genome in RNase protection assays. Five clonal populations of virion RNA were derived from TBD4-infected plants propagated for 170 days (one series involving 10 passages) by isolation of local lesions on N. tabacum Xanthi-nc. The concensus DHFR sequence for three of the populations corresponded with the published DHFR sequence except for a translationally silent third base change (U→C) at nucleotide 72 of the coding sequence. The nucleotide change at position 72 of the DHFR coding sequence was not evident in progeny RNA from TBD4 infected plants propagated for 48 days. Virion RNA from plants serially infected with TBN62 was less stable with different portions of the NPTII sequence being deleted in each of the independent series of passages. The time of loss of these sequences varied between after the first passage (12–24 days) and the third passage (36→47 days). The reason for the occurrence of deletions in the NPTII sequence of TBN62 is not known. However, on the basis of the stability of the DHFR sequences in TBD4, such instability of inserted foreign sequences would not seem to be an intrinsic feature of the expression vector TB2. In contrast, such deletions might be dictated by the nucleotide composition of the inserted foreign sequences themselves. Similar instabilities among DNA plant virus vectors have been seen.

A commercial source of antiserum and sensitive enzymatic assays for the extensively used selectable marker NPTII, McDonnell, R. E. et al., *Plant Mol. Biol. Rep.* 5:380 (1987), allowed further analysis of tissue infected with TBN62. Western blot analysis, enzyme activity, and leaf disc assays demonstrated the presence of functional NPTII enzyme and its phenotypic expression in plant tissue systemically infected with TBN62 but not in TB2-infected or healthy plants. NPTII protein and enzyme activity was even detected in some TBN62-infected plants propagated for 36 days.

It was evident that the levels of extractable NPTII protein were considerably lower than coat protein, the most highly expressed TMV protein. This might be a reflection of the relative stabilities or partitioning of the respective proteins in plant cells, or might be due to one or more aspects of the vector or foreign gene sequences affecting the synthesis of subgenomic mRNA or post-transcriptional expression of the reporter gene. The relatively high yield of virus from plants infected with the vector constructs would seem to preclude a dramatic reduction in the efficiency of virus replication. However, one possibility for low expression might be the position of the reporter gene relative to the 3' terminus of the genome. The amount of the 30 kDa protein produced by different mutants of TMV has been shown to be inversely proportional to the distance the 30 kDa protein ORF was from the 3' terminus of the genome. This relationship was consistent with the observations of French, R. and Ahlquist, P., J. Virol. a: 2411 (1988), i. e., that the level of subgenomic RNA from brome mosaic virus RNA 3 was progressively greater the closer the promoter was inserted to the 3' terminus.

Example 2

Although the RVNA of Example 1 is capable of systemic spread in *N. benthaniana,* it is incapable of systemic spread in *N. tabacum*. This example describes the synthesis of RVNA which is capable of systemic spread in *N. tabacum*.

The O-coat protein coding sequence contained in pTB2 was cut from pTB2 by digestion with AhaIII. The UI-coat protein coding sequence was removed from pTMV204 by digestion with &&III and inserted into AhaIII-digested pTB2 to produce vector pTBU5 (FIG. I).

The XhoI/SalI fragments from pNC4X (DHFR sequence) and pNU116 (NPTII sequence), respectively, are ligated into the XhoI site of pTBU5 in the same sense as the TMV coding sequences. *N. tabacum* plants are inoculated and analyzed as described in Example 1. Functional enzymes are seen in the systemically infected plants but not in the control plants.

Example 3

This example describes the synthesis of RVNA in which the native coat protein gene is under control of its native subgenomic promoter and a non-native subgenomic promoter has been inserted to drive the expression of non-native nucleic acid.

The TMV-O promoter and the TMV-UI coat protein sequence are removed from pTB2 by digesting with XhoI and KpnI. The XhoI end is converted to a PstI site by blunt-ending and adding a PstI linker. This PstI/KpnI fragment is subcloned into a Bluescript vector. Two subclones of this Bluescript vector are created by site-directed mutagenesis as follows:

Bluescript Sub I is prepared by using PCR techniques to create a site-specific fragment that will force a mutation at the ATG (coat protein) start site and create a XhoI site near the ATH site. Bluescript Sub 2 is prepared by using PCR techniques to create a site-specific fragment that will force a mutation at the TAA (coat protein) stop site and create a XhoI site near the TAA site. A PstI/XhoI cut of the Bluescript Sub I and a XhoI/KpnI cut of the Bluescript Sub 2 will give two fragments that can be ligated, giving a PstI/KpnI fragment that has a XhoI cloning insert site that is downstream from the TMV-O promoter. This PstI/KpnI fragment is inserted into the pTKUI vector that has had a NsiI/KpnI fragment removed. (PstI end can be ligated to NsiI). The resulting clone will be pTKU1-a with a TMV-O promoter on the 3' side and a XhoI insert site, into which can be inserted a gene-of-choice, that will be driven by the TMV-O promoter.

The XhoI/SalI fragments from pNC4X (DHFR sequence) and pNU116 (NPTII sequence), respectively, are ligated into the −1 site of pTKU1-a in the same sense as the TMV coding sequences. *N. tabacum* plants are inoculated and analyzed as described in Example 1. Functional enzymes are seen in the systemically infected plants but not in the control plants.

Example 4

Additional DNA coding sequences were prepared for insertion into RVPNAs having either the O-coat protein (Example 1) or the U1-coat protein gene (Example 2). In each instance, the coding sequence was synthesized to contain the XhoI site of pTB2 (Example 1) or pTBU5 (Example 2), in the same sense as the coding sequence.

Standard procedures were used to transform the plasmids into *E. coli* and to isolate the DNA from an overnight culture. Following extraction of the plasmid DNA, an RNA copy of the TB2 or pTBU5 vector (with or without the gene of choice) was made using a DNA-directed RNA polymerase. The RNA was capped during the reaction by adding m7GpppG$_4$, during the transcription reaction, as previously published. This RNA was then used to inoculate a tobacco plant. Standard virus isolation techniques can be used to purify large concentrations of the transient vector for inoculations of multiple numbers of plants.

A coding sequence for Chinese cucumber α-trichosanthin containing XhoI linkers is shown in SEQ ID NO: 3, with the corresponding protein as SEQ ID NO: 4.

A coding sequence for rice α-amylase containing XhoI linkers is shown in SEQ ID NO: 5, with the corresponding protein as SEQ ID NO: 6. This sequence was prepared as follows:

The yeast expression vector pEno/I03 64 was digested with HindIII and treated with mung bean exonuclease to remove the single-stranded DNA overhang. The 0.16 kb HindIII (blunt end) fragment containing the entire rice α-amylase cDNA 05103 65 1990; GenBank accession number M24286) was digested with ScaI and Tinkered with a XhoI oligonucleotide (5' CCTCGAGG 3'). The modified α-amylase cDNA fragment was isolated using low-melt agarose gel electrophoresis, subcloned into an alkaline phosphatase treated XhoI site in pBluescript KS+ (Stratagene, La Jolla, Calif.), and maintained in *E. coli* K-12 strain C-600.

A rice α-amylase coding sequence containing a short 3'-untranslated region was prepared as follows:

The *E. coli* vector pVC18/13, Kurnagi, M. H. et al., *Gene* 94:209 (1990), was digested with KpnI, XhoI and treated with ExoIII and mung bean exonuclease. The modified plasmid was treated with DNA poll, DNA ligase, and transformed into C-600. An isolate, clone pUC18/3 #8, had a 3' deletion that was very close to the stop codon of 05103. This plasmid was digested with EcoRI, treated with mung bean exonuclease, and Tinkered with a XhoI oligonucleotide (5'CCTCGAGG 3'). A 1.4 Kb HindIII-XhoI fragment from the resulting plasmid (pUC18/3 #8X) was isolated using low melt agarose gel electrophoresis, subcloned into pBluescript KS– (Stratagene, La Jolla, Calif.) and maintained in *E. coli* K-12 strains C-600 and JM109. The deletion was sequenced by dideoxy termination using single-stranded templates. The deletion was determined to reside 14 bp past the rice a-amylase stop codon. Plasmid pUC18/3 #8X was digested with HindIII, treated with mung bean exonuclease, and Tinkered with a XhoI oligonucleotide (5'CCTCGAGG 3') A 1.4 Kb XhoI fragment was isolated by trough elution, subcloned into an alkaline phosphatase-treated XhoI site in pBluescript KS+, and maintained in JM109.

A sequencing containing the coding sequence for human α-hemoglobin or β-hemoglobin and transit peptide of petunia EFSP synthase is shown in SEQ ID NO: 7 or SEQ ID NO: 8, and corresponding protein sequences as SEQ ID NO: 9 and SEQ ID NO: 10, respectively.

Purified protein extracts from *N. benthamiana* treated with a recombinant plant viral nucleic acid containing the gene for α-trichosanthin, prepared in accordance with Example 1, were separated using polyacrylamide gel electrophoresis and probed with antibodies specific for α-trichosanthin using standard procedures for Western analysis. FIG. 2 is an autoradiograph of the gels which demonstrates production of processed α-trichosanthin protein in plants treated with a recombinant plant viral nucleic acid containing the gene for α-trichosanthin.

Example 5

Field Tests

The field site design contained two experiments (1 and 2). Experiment 1 was a typical row crop configuration that contained untreated border rows, *Molecular Cloning*, D. M. Clover, Ed., IRL Press, Oxford (1985), of tobacco on all outside perimeter rows as well as internal rows. In addition, every fourth row was a spacer row (S) that was left unplanted in order to allow large farm equipment to access the field (e.g., for spraying pesticides) without coming into direct contact with any of the treated rows (T) Each inoculation was administered by direct hand application of the vector to a single leaf of an individual plant. No spray inoculum was used.

Experiment 2 was a typical plantbed configuration. A high density of plants per square foot was grown at a uniform height by frequent clipping of the plantbed using a modified mower attached to a tractor power takeoff. This experiment contained a complete perimeter border of plantbeds that was not inoculated with the vectors. Inoculation of the treated plantbeds was made using a downward-directed spray through the modified mower blade assembly and administered so as to prevent overspray to adjacent plantbeds.

Experiment 1 was a split-plot design using row culture with seven genotypes as main plots in randomized blocks and four replications. Each plot was 13 feet long and consisted of three rows, with only the middle three or four plants of each center row used for testing. Rows were four feet on center and plants spaced 20 to 22 inches in the row.

Experiment 2 was a randomized complete block design using plantbed culture with four genotypes and three replications. Each plot consisted of a 4-foot by 12-foot plantbed.

Genotypes. Experiment 1: (*Nicotiana tabacum*) K-326, Sp G-28, TI-560, Md-609, Galpao, Wisc-503B and *Nicotiana benthamiana*.

Experiment 2: (*Nicotiana tabacum*) K-326, TI-560, Md-609, Galpao.

Chemical Fertilization. Experiment 1: 800 lbs 6-12-18 after transplanting; 100 lbs 33-0-0 after first harvest; 200 lbs 15-0-14 after second harvest.

Experiment 2: 2400 labs 12-6-6 at time of plantbed formation; 300 labs 33-0-0 after first harvest; 670 lbs 15-0-14 after second harvest.

Clipping. Experiment 2 was clipped twice a week for two weeks, to impart uniformity to the plants.

Weed, Insect and Disease Control. Experiment 1: Prior to forming rows, Paarlan 6B (1 qt/A), Temik 15G (20 lb/A) and Ridomil (2 qts/A) were broadcast-applied and incorporated by disking. During row formation, Telone C-17 (10.5 gal/A) was applied. After transplanting, Dipel (½ lb/A) was applied to control budworms and hornworms. Orthene (⅔ lb/A) was applied to control aphids and hornworms as necessary.

Experiment 2: Ridomil 2G (1 qt/A; 1 oz/150 sq yds) was applied at seeding and at weekly intervals beginning 60–70 days after seeding (as needed). Carbamate 76WP (3 lb/100 gal water) was also used as foliar spray as needed in the initial plantbed stage, to control Anthracnose and Damping-off diseases. At normal transplanting size, Dipel (½ lb/A) was applied. Orthene (⅔ lb/A) was applied to control aphids and hornworms as necessary.

Transplanting. Experiment 1 was transplanted using seedlings pulled from the plantbeds of Experiment 2.

Inoculation. Experiment 1: A single leaf on each non-control plant was hand-inoculated with a selected recombinant plant viral nucleic acid containing NPT II, α-trichosanthin or rice α-amylase. Each individual plant was inoculated with a single vector.

Experiment 2: The plants were inoculated with the vectors described in Experiment 1, using a spray applied through the deck of the clipping mower while the plants are being clipped a final time. Each non-control plot received only a single vector construct. Control plants received no inoculation with any vector.

Data Collection. Experiment 1: Sampling of both inoculated and control plant leaves was conducted on a schedule (approximately weekly) during first growth until plants were approximately 30 inches tall. Plants were then cut (harvest 1) with a rotary brush blade to leave six inches of stalk exposed above the ground. The plants were then allowed to continue growth (second growth) to a height of approximately 30 inches. Leaf samples were taken just before harvest 2. This procedure for cutting, growth and sampling was repeated for third growth and for fourth growth, if detectable amounts of the genes of interest inserted into the vectors were found.

Experiment 2: Sampling of 10 plants from each plot was conducted on a schedule (approximately weekly) from inoculation to harvest 1 and from harvest 1 until harvest 2. Following harvest 2, sampling was conducted only at harvest 3.

Sample Size and Analytical Methods. A 1.6 cm disk was excised from a single leaf near the apex of the plant. Each leaf disk was placed either in a 25 ml glass vial with screw cap and containing absolute ethanol or in a sealable plastic bag.

Leaf discs were either preserved in absolute ethanol or lyophilized. Depending on the specific gene product to be detected, leaf samples were prepared according to standard technigues for Northern or Western blot analyses or specific enzyme activity.

During first growth, visual monitoring of the plants treated with the RVNA were conducted to observe any external phenotypic expression of the vector system. In some cases, the phenotypic expression was typical of Tobacco Mosaic. Virus infections (lighter and darker "mosaic" patterns in the leaf). In other cases, the only symptoms seen were on the inoculated leaf, which included white or brown speckels of approximately 2 mm in diameter and/or suppression of the central vein elongation of the leaf.

Example 6

A full-length DNA copy of the OMV genome is prepared as described by Dawson, W. O. et al., *Proc. Nat. Acad. Sci. USA* 83:1832 (1986). The vector containing the DNA copy of the OMV genome is digested with the appropriate restriction enzymes or suitable exonucleases to delete the coat protein coding sequence. The deletion of the coding sequence for the viral coat protein is confirmed by isolating OMV and using it to infect germinating barley plants. The isolated OMV RNA is incapable of spreading beyond the lesion under natural conditions. A vector containing the OMV sequences is prepared as described in Examples 1–3.

Example 7

A full-length DNA copy of the genome is prepared as described by Dawson, W. O. et al., Proc. Nat. Acad. Sci. USA 83:1832 (1986). The vector containing the DNA copy of the RNV genome is digested with the appropriate restriction enzymes or suitable exonucleases so as to delete the coat protein coding sequence. The deletion of the coding sequence for the viral coat protein is confirmed by isolating RNV RNA and using it to infect germinating barley plants. The isolated is incapable of spreading beyond the lesion under natural conditions. A vector containing the OMV sequences is prepared as described in Examples 1–3.

Examples 8

A full-length DNA copy of the potyvirus (herein after "PVY") or PVX genome is prepared as described by Dawson, W. O. et al., Proc. Nat. Acad. Sci, USA 83:1832 (1986). The vector containing the DNA copy of the PVY or PVX genome is digested with the appropriate restriction enzymes or suitable exonucleases to delete the coat protein coding sequence. The deletion of the coding sequence for the viral coat protein is confirmed by isolating PVY or PVX [ENA] RNA and using it to infect potato plants. The isolated PVY or PVX RNA is incapable of spreading beyond the lesion under natural conditions. A vector containing the OMV sequences is prepared as described in Examples 1–3.

Example 9

A full-length DNA copy of the maize streak virus (MSV) genome is prepared as described by Dawson, W. O. et al., *Proc. Nat. Acad. Sci. USA* 83:1832 (1986). The vector containing the DNA copy of the Msv genome is digested with appropriate restriction enzymes or suitable exonucleases to delete the coat protein coding sequence. Deletion of the coding sequence for the viral coat protein is confirmed by isolating MSV and using it to infect potato plants. The isolated MSV is incapable of spreading beyond the lesion under natural conditions. A vector containing the OMV sequences is prepared as described in Examples 1–3.

Example 10

A full-length DNA copy of the TGMV genome is prepared as described by Dawson, W.O. et al., *Proc. Nat. Acad. Sci. USA* 83:1832 (1986). The vector containing the DNA copy of the TGMV genome is digested with the appropriate restriction enzymes or suitable exonucleases to delete the coat protein coding sequence. The deletion of the coding sequence for the viral coat protein is confirmed by isolating TGMV RNA and using it to infect potato plants. The isolated TGMV RNA is incapable of spreading beyond the lesion under natural conditions. A vector containing the TGMA sequences is prepared as described in Examples 1–3.

Example 11

The coding sequence for beta-cyclodextrin glucotransferase (CGT) is isolated from alkalophilic Bacillus sp. strain No.38-2 in the following manner:

The chromosomal DNA of strain No. 38-2, Hanamoto, T. et al., *Agric. Biol. Chem.* 51:2019- 87(1987), is partially cleaved with Sau3AI, and the fragments ligated in BamHI-digested pBR322. A transformant carrying plasmid pCS115, which contains a 3.2 kb DNA fragment from the genome of the producing strain, has the CGT activity. The CGT produced by this transformant gives one line of precipitation which fuses completely with that for the No. 38-2 CGT by an Ouchterlony double-diffusion test. The nucleotide sequence of the fragment is found by the dideoxy chain termination reaction using pUC19, and the exonuclease deletion method. Henikoff, S., *Gene* 28:351 (1984). The nucleotide sequence of the fragment shows a single open reading frame corresponding to the CGT gene. A protein with a molecular mass of 66 kDal could be translated from this open reading frame of 1758 bp. For the detailed nucleotide sequence, see Hanamoto, T. et al., *Agric. Biol. Chem.* 51:2019 (1987).

The sequence of the N-terminal amino acids of the extracellular form of CGT is found with a peptide sequencer. $NH_2$-Ala-Pro-Asp-Thr-Ser-Val-Ser-A5n-Lys-Gln-Asn-Phe-Ser-Thr-Asp-Val-Ile (SEQ ID NO: 6) is identical to that deduced from the DNA sequence (residues 1 to 17). This result suggests that 27 amino acid residues (residues -27 to -1) represent a signal peptide which is removed during secretion of CGT. The molecular weight of the matured CGT calculated from the DNA sequence is 63,318.

A probe is prepared based on a portion of the amino acid sequence of CGT and used to isolate the coding sequence for this enzyme. Alternatively, the CGT coding sequence is isolated following reverse transcription. The fragment containing the coding sequence is isolated and cloned adjacent the subgenomic promoter of the native viral coat protein gene in the vectors prepared in Examples 6–10.

Example 12

The RVNA of Example 11 is used to infect corn plants (viruses based on OMV, RNV, or TGMV) or potato plants (viruses based on PVY or PVX). The infected plants are grown under normal growth conditions. The plants produce cyclodextrin glucotransferase which catalyzes the conversion of starch to cyclodextrin in the plant tissue. The cyclodextrin is isolated by conventional techniques.

Example 13

A. The coding sequence for an esterase is isolated from *Bacillus subtilis* Thai 1–8 (CBS 679.85) as follows. The positive selection vector pUN121, Nilsson et al., *Nucl. Acids Res.* 11:8019 (1983), is used. This vector carries an ampicillin resistance gene, a tetracycline resistance gene and a $C_1$-repressor gene. Transcription of the tetracycline gene is prevented by the gene product of the $C_1$-repressor gene. Insertion of foreign DNA into the BclI site of the $C_1$-repressor gene results in activation of the tetracycline gene. This allows positive selection of recombinants on ampicillin/tetracycline agar plates.

Partially Sau3a-digested *Bacillus subtillis* Thai 1–8 DNA is mixed with BclI-digested pUN121 DNA. After recirculation by the use of polynucleotide ligase, the DNA mixture is introduced into *E. coli* DH1 (ATCC No. 33849) using the $CaCl_2$ transformation procedure. One thousand *E. coli* colonies are obtained which are resistant to ampicillin and tetracycline. All transformants are stored and replica-plated according to Gergan et al., Nucl. Acids Res. 7: 2115 (1979). Replicated colonies are screened using a soft agar overlay technique, based on a previously described procedure to detect esterase activity. Higerd et al., J. Bacterial, 1184 (1973). Essentially, a mixture of 0.5% low melting agarose, 0.5M potassium phosphate(pH 7.5), 0.5 mg/l B-naphthyl acetate and 0.5 mg/ml fast-blue is spread over the transformants. Within a few minutes, colonies with esterase or lipase activity develop purple color. Such colonies are grown overnight in 2XYT (16 g/l Bactotryptone, 10 g/l yeast extract, 5 g/l NaCl)medium and subsequently assayed for their ability to convert S-naproxen ester to S-naproxen (the method of Example 1 of EP-A 0233656). One *E. coli* transformant is able to convert S-naproxen ester. The plasmid isolated from this transformant, which is called pNAPT-2 (CBS 67186). Its size is 9.4 kb.

HindIII restriction enzyme fragments of pNAPT-2 are ligated into pNeo/ori. This is performed as described below. pPNeo/ori is constructed by ligating the 2.7 kb EcoRI/SmaI restriction fragment of pUC19 to the 2.5 kb EcoRI/SMA I restriction fragment of pUB110. The resulting shuttle plasmid, pPNeo/ori (5.2 kb) has the capacity to replicate both in *E. coli* and in Bacillus species due to the presence of the pUC19 origin, and the pUB110 origin. In addition, pPNeo/ori carries a gene encoding ampicillin resistance and a gene encoding neomycin resistance.

For subcloning, UdIII-digested pNAPT-2 is mixed with HindIII-digested pPNeo/ori and ligated. The mixture is transformed to *E, coli* JM101 as described in Maniatis et al., *Molecular Cloning* (1st Ed.)). *E. coli* JM101 hsds is obtained from the Phabagen collection (Accession No. PC 2493, Utrecht, The Netherlands). Colonies capable of hydrolyzing β-naphthyl acetate are selected as described in Example 56 of EPA 0 233 656. From two positive colonies, pNAPT-7 and pNAPT-8 plasmid DNA is isolated and characterized in detail by determining several restriction enzyme recognition positions.

B. The coding sequence for an *E. coli* esterase is prepared as follows:

Plasmids pIP1100 (isolated from *E. coli* BM 2195) and pBR322 are mixed, digested with AvaI, ligated and transformed into *E. coli*, and clones are selected on erythromycin (200 /g/ml). Transformants resistant to ampicillin and erythromycin but also to spectinomycin are analyzed by agarose gel electrophoresis of crude lysates. The transformant harboring the smallest hybrid plasmid is selected, its plasmid DNA is digested with −1, and the 3.5 kb 20 pIP1100 insert is purified and partially digested with m3A. The restriction fragments obtained are cloned into the BamHI site of pBR322 and transformants selected on Em are replica-plated on Sm. The plasmid content of transformants resistant 25 only to Ap and Em is analyzed by agarose gel electrophoresis. DNA from the smallest hybrid, pAT63, is purified and analyzed by agarose gel electrophoresis after digestions with m3A, -RI, WI or HindIII-BamHI endonucleases (not shown). Plasmid pAT63 consists of pBR322 plus a 1.66 kb pIP1100 DNA insert. Purified EcoRI-HindIII (1750-bp) and BamHI-PstI (970-bp) fragments of pAT63 are subcloned into pUC8 and found not to confer resistance to Em.

The HpaII-BamHI fragment of pAT63 is sequenced according by the Sanger technique. The complete sequence is shown in Ounissi, H. et al., *Gene* 35:271 (1985).

C. The coding sequence from acylase is isolated from *Arthrobacter viscosus* 8895GU, ATCC 27277 follows.

A gene library of *A. viscosus* 8895GU is constructed by inserting EcoRI-cleaved *A. viscosus* chromosomal DNA into the EcoRI cleavage site of pACYC184. The vector DNA and *A. viscosus* DNA are both digested with EcoRI. The 5' end of the vector DNA is dephosphorylated with calf intestinal alkaline phosphatase. Dephosphoroylated vector DNA and digested *A. viscosus* DNA are incubated with T4 DNA ligase and transformed into *E. coli* HB101. Transformed colonies of *E. coli* were screened by the *Serratia marcescens* overlay technique. Penicillin G was added to the medium. *S. marcescens* is sensitive to the deacylation product of penicillin G, 6-aminopenicillamic acid (6-APA). Colonies of transformed *E. coli* will produce areas of *S. marcescens* inhibition in overnight cultures. The plasmid carried by transformed *E. coli* is referred to as pHYM-1. The plasmid having opposite DNA orientation is designated pHYM-2. Ohashi, H. et al., *Appl. Environ. Microbiol.* 54:2603 (1988).

D. A coding sequence for human gastric lipase mRNA is prepared by guanidinium isothiocyanate extraction of frozen tissue. Polyadenylated RNA is isolated by oligo(dT)-cellulose chromatography. cDNA is prepared from human stomach mRNA by procedures well known in the art. cDNA is annealed to PstI-cut dG-tailed pBR322. The hybrid plasmid is transformed into *E. coli* DH1. Transformants are screened by colony hybridization on nitrocellulose filters. The probe used is synthesized from the rat lingual lipase gene and labeled by nick translation. Positive colonies are grown up and plasmids are analyzed by restriction endonuclease mapping.

An esterase acylase or lipase gene prepared as described above is removed from the appropriate vector, blunt-ended using mung bean nuclease or DNA polymerase I, and X&I linkers added. This esterase 10 with −1 linkers is cleaved with −1 and inserted into the vectors described in Examples 1–3 or 6–10 Infection of the appropriate host plants by the RVNA prepared in accordance with Example 2 results in the synthesis of esterase, acylase or lipase in the plant tissue. The enzyme is isolated and purified by conventional techniques and used to prepare stereospecific compounds.

Example 14

The coding sequence for CMS-T is isolated from a 20-1 maize mtDNA library as described by Dewey, R. E. et al., Cell fi: 439 (1986). The ORF-13 coding sequence is isolated by restriction endonuclease digestion followed by 5'-exonuclease digestion to the start codon. Alternatively, a restriction site is 25 engineered adjacent the start codon of the ORF-13 coding sequence by site-directed oligonucleotide mutagenesis. Digestion with the appropriate restriction enzyme yields the coding sequence for ORF-13. The fragment containing the ORF-13 coding sequence is isolated and cloned adjacent the promoter of the native viral coat protein gene in the vectors prepared in Examples 6, 7 and 10.

Maize plants are infected by the RVNA prepared in accordance with Example 1. The infected plants are grown under normal growth conditions. The plants produce cms-T which induces male sterility in the infected maize plants.

Example 15

The coding sequence of $S_2$-protein (for self-incompatibility) is isolated from *Nicotiana alata* as described in EP-A 0 222 526. The $S_2$-protein coding sequence is isolated by restriction endonucleuse digestion followed by 5'-exonuclease digestion to the start codon. Alternatively, a restriction site is engineered adjacent the start codon of the $S_2$-protein coding sequence by site-directed oligonucleotide mutagenesis. Digestion with the appropriate restriction enzyme yields the coding sequence for $S_2$-protein. The fragment containing the $S_2$-protein coding sequence is isolated and cloned adjacent the promoter of the viral coat protein gene in the vectors prepared in Examples 1–3.

Tobacco plants are infected by the RVNA prepared in accordance with Example 1, prior to pollen formation. The infected plants are grown under normal growth conditions. The plants produce S-protein which induces male sterility via the self-incompatibility mechanism.

The following example demonstrates that high levels of therapeutic proteins can be expressed using the plant RNA viral vectors of the present invention. Trichosanthin is a eukaryotic ribosome inactivating protein found in the roots of a Chinese medicinal plant. Wang, Y., Qian, R.-Q., Gu., Z.-W., Jin, S.-W., Zhang, L.-Q., Xia, Z.-X., Tian, G.-Y. & Ni, C.-Z. *Pure appl. Chem.* 58:789-798 (1986). In *Trichosanthes kirilowii* Maximowicz, α-trichosanthin is a monomeric protein which catalyzes the cleavage of an N-glycosidic bond in 28S rRNA (Jimenez, A. & Vazquez D. *Annu. Rev. Microbiol.* 39:649–672 (1985); Endo, Y., Mitsui, K., Motizuui, M. & Tsurugi, K *J. Biol. Chem.* 262:5908–5912 (1987)). This reaction inhibits protein synthesis by affecting the ability of the 60S ribosomal subunit to interact with elongation factors. The mature compound has an approximate relative molecular mass of 27 kDa and is initially produced as a preprotein. Maraganore, J. M., Joseph, M. & Bailey, M. C., *J. Biol. Chem.* 262:11628–11633 (1987). During its biosynthesis, a putative 23 amino acid secretory signal peptide is removed and a 19 amino acid peptide is probably excised from the carboxy terminus.

Purified *T. kirilowii* derived α-trichosanthin causes a concentration-dependent inhibition of HIV replication in acutely infected CD4+ lymphoid cells, and in chronically infected macrophages (Collins, E. J., Robertus, J. D., LoPresti, M., Stone, K. L., Williams, K. R., Wu, P., Hwang, & Piatak, M., *J. Biol. Chem.* 265:8665–8669 (1990); McGrath., M. S., Hwang, K. M., Caldwell, S. E., Gaston, I., Luk, K. C., Wu, P., Ng, V. L., Crowe, S., Daniels, J., Marsh, I., Dienhart, T., Lekas, P. V., Vennari, J. C., Yeung, H. J. & Lifson, D. *Proc. Nat. Acad. Sci. U.S.A.* 86:2844–2848 (1989)). This compound is currently being evaluated in clinical studies as a potential therapeutic drug in the treatment for HIV infection. Shaw, P.-C., Yung, M.-H., Zhu, R.-H., Ho, W. K.-K., Ng, T.-B. & Yeung, H.-W. *Gene* 97:267–272 (1991). The exact mechanism of anti-HIV infection by α-trichosanthin is not known. Amino acids involved in catalysis and inhibition of HIV replication may be identified using site directed mutagenesis. Detailed structure/function analysis will require an abundant source of recombinant protein as well as a rapid method for generating and analyzing mutants. Although the expression of α-trichosanthin in *E. coli* has been reported previously (Ahlquist, P., French, R., Janda, M. & Loesch-Fries, S., *Proc. Nat. Acad. Sci. U.S.A.* 81:7066–7070 (1984); Piatak, et al., U.S. Pat. No. 5,128,460 (1992)), the amount synthesized was low (approximately 0.01 total cellular protein), the carboxy terminal extension was not removed, and the biological activity of the compound was not determined.

Tobamoviruses, whose genomes consist of one plus-sense RNA strand of approximately 6.4 kb, have been used to produce heterologous proteins. RNA transcripts from viral cDNA clones serve as infectious templates, encoding proteins involved in RNA replication, movement, and encapsidation. Miller, W. A., Dreher, T. W. & Hall, T. C., *Nature* 313:68–70 (1985). Subgenomic RNA for messenger RNA synthesis is controlled by internal promoters located on the minus-sense RNA strand. Takamatsu, N., Watanabe, Y., Yanagi, H., Meshi, T., Shiba, T. & Okada, Y. *FEBS Lett.* 269, 73–76 (1990). TMV RNA viruses have been used previously to express Leu-enkephlin in tobacco protoplasts, Talcamatsu, N., Ishilcawa, M., Meshi, T. & Okada, Y. *EMBO J.* 6:307–311 (1987), and bacterial chloramphenicol acetyltransferase in inoculated tobacco leaves (Dawson, W. O., Lewandowski, D. J., Hilf, M. E., Bubrick, P., Raffo, A. J., Shaw, J. J., Grantham, G. L. & Desjardins, P. R. *Virology* 172:285–292 (1989);

Donson, J., Kearney, C. M., Hilf, M. E. & Dawson, W. O. *Proc. Nat. Acad. Sci. U.S.A.* 88:7204–7208 (1991)). These previous attempts to express foreign genes have resulted in either unstable constructs or loss of long distance viral movement. Recently, *Nicotiana benthamiana* plants transfected with a hybrid virus consisting of tobacco mosaic virus, strain U1 (TMV-U1 ) and an additional RNA subgenomic promoter from odontoglossum ringspot virus (ORSV) produce a systemic and stable expression of neomycin phosphotransferase. Chow, T. P., Feldman, R. A., Lovett, M. & Piatak, M. *J. Biol. Chem.* 265:8670–8674 (1990).

Construction of pBGC152

The plasmid pSP6-TKU1 contains the entire TMV-U1 genome fused to the SP6 promoter by oligonucleotide directed mutagenesis and inserted into pUC118 as a XhoI/KpnI fragment. The sequence of the mutagenesis primer used to attach the SP6 promoter sequence to the TMV genome is: 5'-GGGCTCGAGATTTAGGTGACACTATAGTATTTTA- CAACAATTACCA3' (SEQ ID NO: 12) wherein the XhoI site is in italics, the SP6 promoter is in boldface and the TMV sequence is underlined. The primer was attached to a TMV subclone called pC48 (Raffo, et al, *Virology* 184: 277–289 (1991)). The promoter was attached by PCR using the above primer and a primer complementary to TMV sequences 5673 to 5692. This amplification produced a fragment of ca. 614 bp, which was then digested with XhoI and EcoRI (TMV 270) to produce a ca. 292 bp fragment which was then subcloned into similarly cut pUC129 resulting in plasmid pSP6-T1.

pSP6-T1 was cut with XhoI and XmaI (a SmaI isoschizomer which cuts at TMV 256) and the resulting ca. 278 bp fragment was ligated into pTKU1 (Donson, et al. *Proc. Natl. Acad. Sci. U.S.A.* 88:7204–7208 (1991)) which had been modified by cutting at the unique PstI site at the 5' end of the genome, blunting with T4 DNA polymerase, followed by the addition of XhoI linkers. This resulted in the infectious clone pSP6-TKU1 and XmaI digested.

Figure 7:
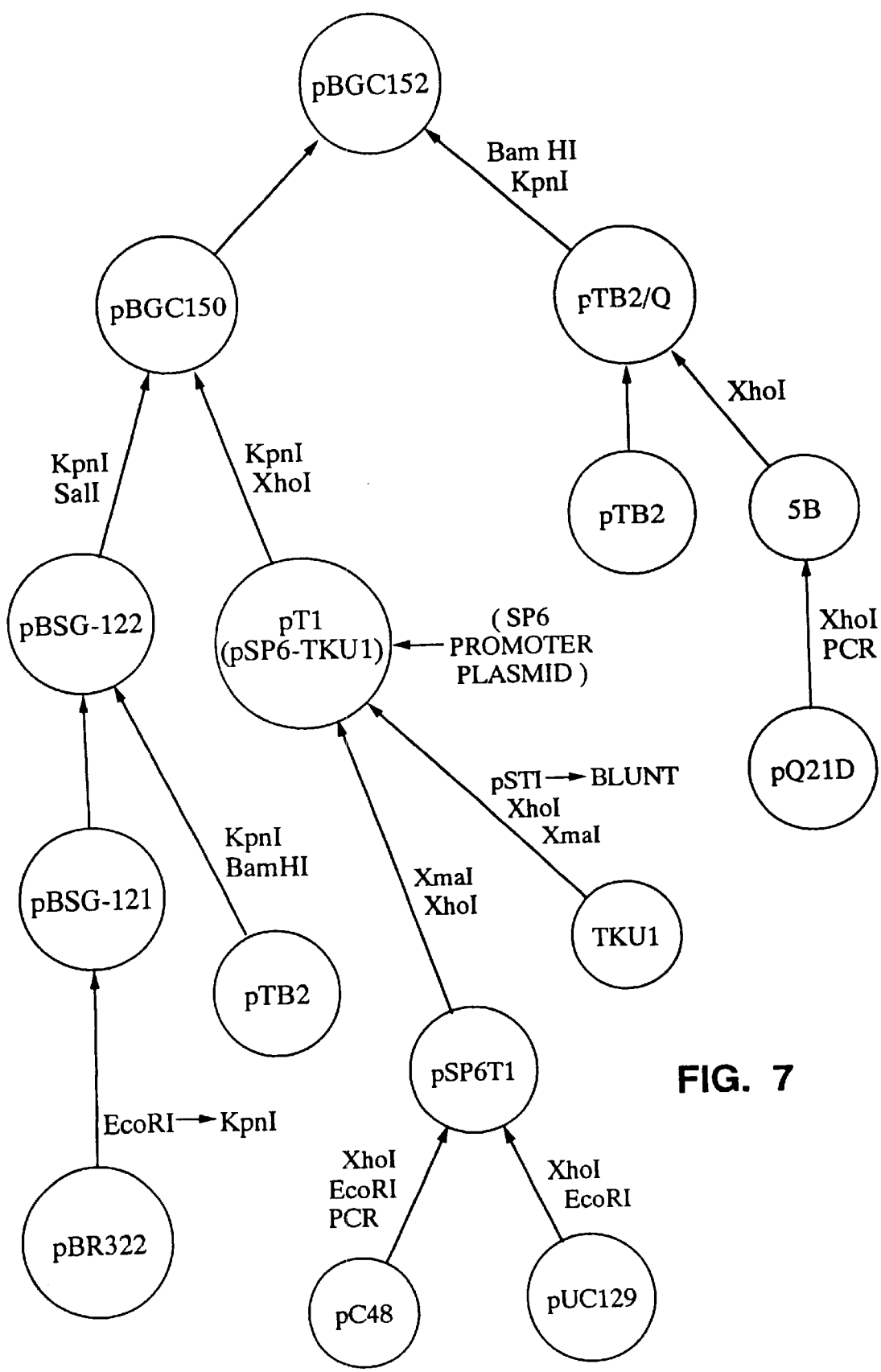
FIG. 7 illustrates the construction of the pBGC152 plasmid.

As shown in FIG. 7, the EcoRI site in pBR322 was mutagenized to a KpnI site using EcoRI, DNA polymerase (Klenow), and KpnI linkers. A KpnI\BamHI fragment of the resulting plasmid, pBSG121, was substituted with a KpnI\BamHI fragment of pTB2 (ATCC No. 75,280 deposited Jul. 24, 1992). A SalI/KpnI fragment of the resulting plasmid, pBSG122, was substituted with a XhoI/KpnI fragment of pSP6-TKUI (also known as T1) which resulted in plasmid pBGC150.

A BamHI/KpnI fragment of pBGC150 was substituted with a BamHI/-KpnI fragment of pTB2/Q resulting in plasmid pBGC152. pTB2/Q was constructed beginning with plasmid pQ21D (ATCC No. 67907) described in Piatak, Jr., et al, U.S. Pat. No. 5,128,460, the contents of which are incorporated herein by reference. The plasmid "clone 5B" containing a PCR amplified 0.88 kb XhoI fragment of the TCS sequence in pQ21D was obtained using oligonucleotide mutagenesis to introduce Xho1 cloning sites at the start and stop codons of pQ21D such that the following sequence was obtained: 5'-CTCGAGG<u>ATG ATC</u> (SEQ ID NO: 13) - -- ---//--- --- ATT TAG TAA CTCGAG-3' (SEQ ID NO: 17) (XhoI site in italics). A 0.88 kb XhoI fragment from "clone B" was subcloned into the XhoI site of plasmid pTB2 in the sense orientation to create plasmid pTB2/Q.

In vitro Transcriptions, Inoculations, and Analysis of Transfected Plants

*N. benthamiana* plants were inoculated with in vitro transcripts of KpnI digested pBGC152 as described previously. Hiatt, A., Cafferkey, R. & Bowdish, K. *Nature* 342:76–78 (1989). Virions were isolated from *N. benthamiana* leaves infected with BGC152 transcripts, stained with 2% aqueous uranyl acetate, and transmission electron micrographs were taken using a Zeiss CEM902 instrument.

Purification, Immunological Detection, and in vitro Assay of α-trichosanthin

Two weeks after inoculation, total soluble protein was isolated from 3.0 grams of upper, non-inoculated *N. benthamiana* leaf tissue. The leaves were frozen in liquid nitrogen and ground in 3 mls of 5% 2-mercaptoethanol, 10 mM EDTA, 50 mM potassium phosphate, pH 6.0. The suspension was centrifuged and the supernatant, containing recombinant α-trichosanthin, was loaded on to a Sephadex G-50 column equilibrated with 2 mM NaCl, 50 mM potassium phosphate, pH 6.0. The sample was then bound to a Sepharose-S Fast Flow ion exchange column. Alpha-trichosanthin was eluted with a linear gradient of 0.002–1 M NaCl in 50 mM potassium phosphate, pH 6.0. Fractions containing α-trichosanthin were concentrated with a Centricon-20 (Amicon) and the buffer was exchanged by diafiltration (Centricon-10, 50 mM potassium phosphate, pH 6.0, 1.7 M ammonium sulfate). The sample was then loaded on a HR5/5 alkyl superose FPLC column (Pharmacia) and eluted with a linear ammonium sulfate gradient (1.7–0 M ammonium sulfate in 50 mM potassium phosphate, pH 6.0). Total soluble plant protein concentrations were determined, Sijmons, P. C., Dekker, B. M. M., Schrammeijer, B., Verwoerd, T. C., van den Elzen, P. J. M.& Hoekema, A. *Bio/Technology* 8:217–221 (1990), using BSA as a standard. The concentration of α-trichosanthin was determined using the molar extinction coefficient of $E_{280}$=1.43. The purified proteins were analyzed on a 0.1% SDS, 12.5% polyacrylamide gel, Hewick, R. M., Hunkapiller, N. W., Hood, L. E. & Dreyer, W. J. *J. Biol. Chem.* 256:7990–7997 (1981), and transfered by electroblotting for 1 hour to a nitrocellulose membrane. von Heijne, G. *Nucleic Acid Res.* 14:4683–4690 (1986). The blotted membrane was incubated for 1 hour with a 2000-fold dilution of goat anti-α-trichosanthin antiserum. The enhanced chemiluminescence horseradish peroxidase-linked, rabbit anti-goat IgG (Cappel) was developed according to the manufacturer's (Amersham) specifications. The autoradiogram was exposed for <1 second. The quantity of total recombinant α-trichosanthin in an extracted leaf sample was determined by comparing the crude extract autoradiogram signal to the signal obtained from known quantities of purified GLQ223. The ribosome inactivating activity was determined by measuring the inhibition of protein synthesis in a rabbit reticulocyte lysate system.

Confirmation of High Level Expression of Bilogically Active α-trichosanthin

Figure 3B:
Figure 4:
FIG. 4 illustrates an electron micrograph of virions from systemically infected leaves of *N. benthamiana* transfected with in vivo pBGC152 transcripts. The length of the black bar located in the bottom left corner of the micrograph represents approximately 140 nm.
Figure 5A:
FIG. 5*a* is a protein analysis of a transfected *N. benthamiana* plant two weeks after inoculation. a, Western blot analysis. Lane 1: 200 ng of GLQ223; 2: 50 ng of GLQ223; 3: 7 µg of total soluble protein from *N. benthamiana* infected with pBGC152 transcripts; 4: peak fraction from alkyl superose FPLC chromatography; 5: 7 µg of total soluble protein from noninfected *N. benthamiana;* 6: 7 µg of total soluble protein from noninfected *N. benthamiana* and 100 ng of GLQ223.
Figure 5B:
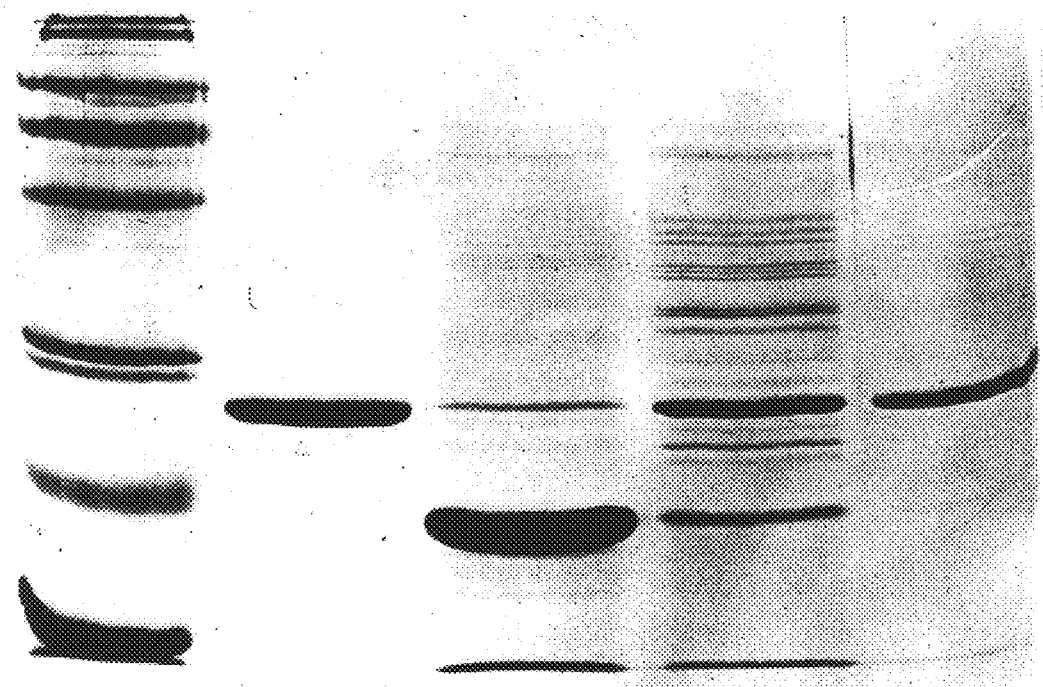
FIG. 5*b* is a purification profile of recombinant α-trichosanthin. The samples from various stages during purification were analyzed by 12.5% SDS-polyacrylamide gel electrophoresis. Lane 1: Amersham prestained high-range molecular weight standards; 2: purified GLQ223; 3: total soluble protein from *N. benthamiana* infected with pBGC152 transcripts; 4: peak fraction from S-sepharose chromatography; 5: peak fraction from alkyl superose FPLC chromatography.

The plant viral vector of the present invention directs the expression of α-trichosanthin in transfected plants. The open reading frame (ORF) for α-trichosanthin, from the genomic clone pQ21D, Saiki, R. K., Scharf, S., Faloona, F., Mullis, K. B., Horn, G. T., Erlich, H. A. & Amheim, N. *Science* 230:1350–1354 (1985), was placed under the control of the tobacco mosaic virus (TMV) coat protein subgenomic promoter. Infectious RNA from pBGC 152 (FIG. 3) was prepared by in vitro transcription using SP6 DNA-dependent RNA polymerase and were used to mechanically inoculate *N. benthamiana*. The hybrid virus spread throughout all the non-inoculated upper leaves as verified by transmission electron microscopy (FIG. 4), local lesion infectivity assay, and polymerase chain reaction (PCR) amplification (20; data not shown). The 27 kDa α-trichosanthin accumulated in upper leaves (14 days post inoculation) to levels of at least 2% of total soluble protein and was analyzed by immunoblotting, using GLQ223, Collins, E. J., Robertus, J. D., LoPresti, M., Stone, K. L., Williams, K. R., Wu, P., Hwang, & Piatak, M., *J. Biol. Chem.* 265:8665–8669 (1990), a purified *T.kirilowii* derived α-trichosanthin, as a standard (FIG. 5A). No detectable cross-reacting protein was observed in the non-infected *N. benthamiana* control plant extracts (FIG. 5A, lane 5). Recombinant α-trichosanthin was easily detected in 7 μg of crude leaf extract using a Coomassie stain (FIG. 5B, lane 3 ).

Prior investigators have reported a maximum accumulation of a foreign protein in any genetically engineered plant of 2% of the total soluble protein. Although the expression of potentially valuable proteins such as antibodies and human serum albumin has been reported previously (Laemmli, U. K. *Nature* 227:680–685 (1970); Bradford, M. M. *Anal. Biochem.* 72:248–254 (1976)) these were produced in Agrobacterium-mediated transgenic plants. A major difference between this plant viral expression system and previous methods is the quantity of protein produced and the amount of time required to obtain genetically engineered plants. Systemic infection and expression of α-trichosanthin occurred in less than two weeks while it takes several months to create a single transgenic plant.

The α-trichosanthin produced and purified from upper leaves in transfected *N. benthamiana* (14 days post inoculation) was structurally identical to native α-trichosanthin. The 27 kDa protein cross-reacted with anti-α-trichosanthin antibody and had an identical FPLC purification profile as the GLQ223 standard. Although the C-terminal sequence of the recombinant protein was not analyzed, both GLQ223 and the purified recombinant α-trichosanthin appeared to have identical electrophoretic mobilities (FIG. 5B). The exact C-terminal amino acid of the recombinant α-trichosanthin remains to be determined. The N-terminal sequence, Asp-Val-Ser-Phe-Arg-Leu-Ser was obtained from the purified protein using an automated protein sequenator. Towbin, H., Staehelin, T., Gordon, J. *Proc. Natl. Acad. Sci. U.S.A.* 76:4350–4354 (1979). This result indicated that the putative signal peptide of the preparation was correctly processed at the site indicated in FIG. 1. The removal of the putative signal peptide at this site was consistent with the statistical expectation by the method of von Heijne. Piatak, et al., U.S. Pat. No. 5,128,460 (1992). It is possible that the α-trichosanthin signal peptide contributed to its high level expression by targeting the protein into the extracellular space. The nucleotide sequences surrounding the α-trichosanthin start codon might also have an effect on the efficiency of translation initiation.

It is interesting to note that nucleotides flanking the translation initiating sites of the highly expressed TMV-U1 (5' TTAAATATGTCT 3') (SEQ ID NO: 18) and ORSV (5' TGAAATATGTCT 3') (SEQ ID NO: 19) coat protein genes are conserved while the corresponding region in pBGC152/α-trichosanthin (5' TCGAGGATGATC 3') (SEQ ID NO: 14) shows very little similarity. It is possible that site directed mutagenesis of nucleotides near the translation initiation site of α-trichosanthin might increase its expression.

Figure 6:
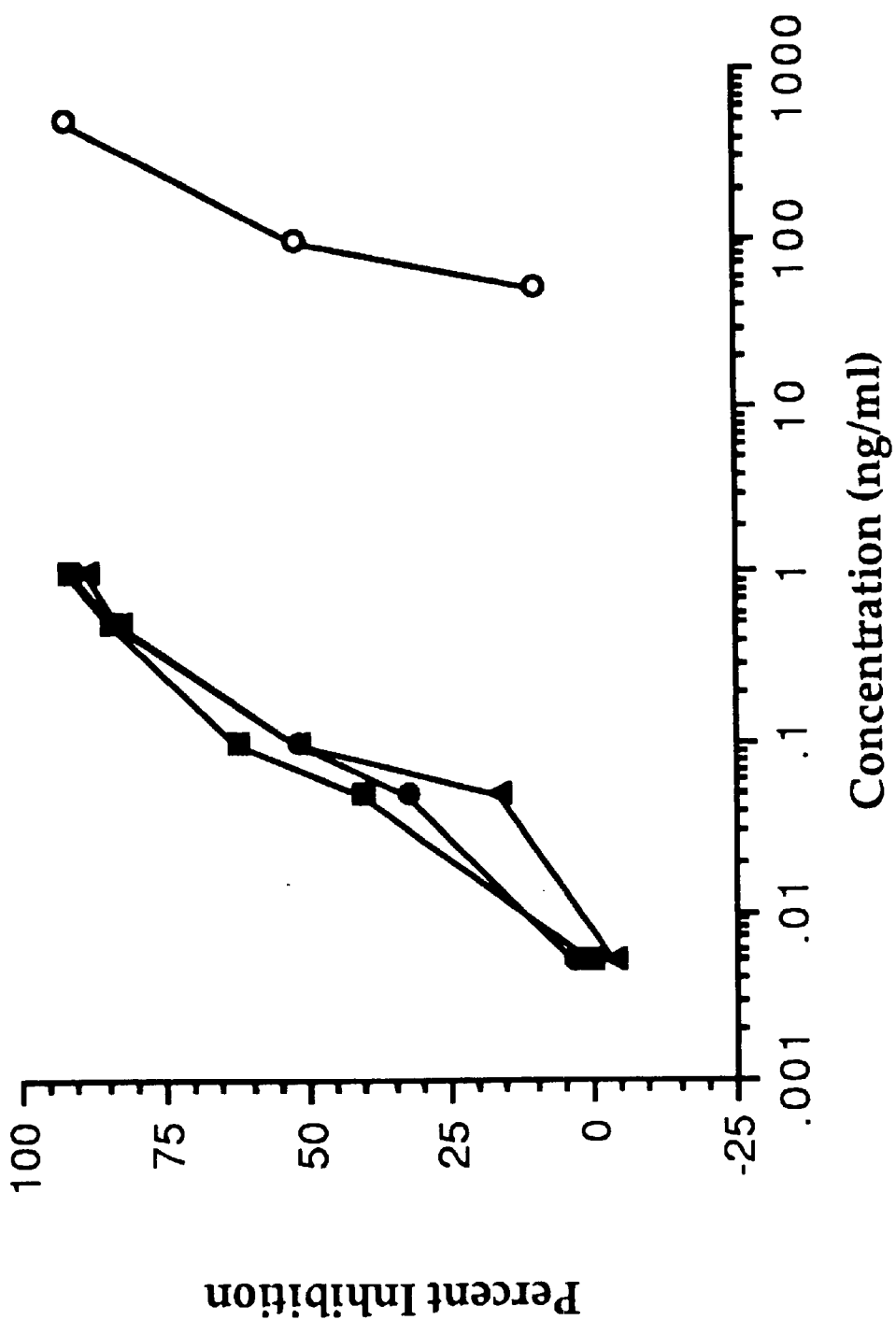
FIG. 6 illustrates the inhibition of protein synthesis in a cell-free rabbit reticulocyte translation assay. Dosage required for 50% inhibition ($ID_{50}$). Purified α-trichosanthin from *N. benthamiana* infected with BGC 152 transcripts (blackened circles and triangles, repetition 1 and 2), GLQ233 (blackened square), and cycloheximide (open circle) were analyzed in varying concentrations for their ability to inhibit protein synthesis in vitro.

The recombinant α-trichosanthin caused a concentration dependent inhibition of protein synthesis in a cell-free rabbit reticulocyte translation assay (FIG. 6). The $ID_{50}$ (dosage required for 50% inhibition) was approximately 0.1 ng/ml, a value comparable to *T.kirilowii* derived α-trichosanthin (GLQ223). Based on the $ID_{50}$ and dose response, the enzyme produced in transfected plants had the same specific activity as the native protein. This result suggests that the fidelity of the viral RNA-dependent RNA polymerase was relatively high since base pair substitutions and deletions in the foreign sequence during viral amplification would lower the specific activity of the recombinant enzyme.

As the disclosed and claimed invention demonstrates, pBGC152 can direct the heterologous expression of biologically active α-trichosanthin in transfected plants. Large scale production of recombinant proteins can be easily obtained using the RNA viral-based system by simply increasing the size and number of inoculated plants. Since tissue containing high concentrations of α-trichosanthin can be harvested two weeks after inoculation this system can be used to rapidly screen the effects of site directed mutations. Identification of important amino acids involved in the inhibition of HIV replication in vivo may help to improve the efficacy of α-trichosanthin as a potential AIDS therapeutic drug.

Example 17

Preparation of a Non-Transmissible TMV Nucleotide Sequence

A full-length DNA copy of the TMV genome is prepared and inserted into the Pst I site of pBR322 as described by Dawson, W. O. et al., *Proc. Nat. Acad. Sci. USA* 83, 1832 (1986). The viral coat protein gene is located at position 5711 of the TMV genome adjacent the 30 k protein gene. The vector containing the DNA copy of the TMV genome is digested with the appropriate restriction enzymes and exonucleases to delete the coat protein coding sequence. For example, the coat protein coding sequence is removed by a partial digestion with ClaI and NsiI, followed by relegation to reattach the 3'-tail of the virus. Alternatively, the vector is cut at the 3' end of the viral nucleic acid. The viral DNA is removed by digestion with Bal31 or exonuclease III up through the start codon of the coat protein coding sequence. A synthetic DNA sequence containing the sequence for the viral coat protein is confirmed by isolating TMV RNA and using it to infect tobacco plants. The isolated TMV RNA is found to be non-infective, i.e. biologically contained, under natural conditions.

Example 18

Preparation of a Non-Transmissible OMV Nucleotide Sequence

A full-length DNA copy of the OMV genome is prepared as described by Dawson, W. O. et al., *Proc. Nat. Acad. Sci. USA* 83, 1832 (1986). The vector containing the DNA copy of the OMV genome is digested with the appropriate restriction enzymes or suitable exonucleases such as described in Example 4 to delete the coat protein coding sequence. The deletion of the coding sequence for the viral coat protein is confirmed by isolating OMV RNA and using it to infect germinating barley plants. The isolated OMV RNA is found to biologically contained under natural conditions.

Example 19

Preparation of a Non-Transmissible RNV Nucleotide Sequence

A full-length DNA copy of the RNV genome is prepared as described by Dawson, W. O. et al., *Proc. Nat. Acad. Sci. USA* 83, 1832 (1986). The vector containing the DNA copy of the RNV genome is digested with the appropriate restriction enzymes or suitable exonucleases such as described in Example 4 to delete the coat protein coding sequence. The deletion of the coding sequence for the viral coat protein is confirmed by isolating RNV RNA and using it to infect germinating barley plants. The isolated RNV RNA is found to be noninfective under natural conditions.

Example 20

Preparation of a Non-Transmissible PVY or PVX Nucleotide Sequence

A full-length DNA copy of the PVY or PVX genome is prepared as described by Dawson, W. O. et al., *Proc. Nat. Acad. Sci. USA* 83, 1832 (1986). The vector containing the DNA copy of the PVY or PVX genome is digested with the appropriate restriction enzymes or suitable exonucleases such as described in Example 17 to delete the coat protein coding sequence. The deletion of the coding sequence for the viral coat protein is confirmed by isolating PVY or PVX RNA and using it to infect potato plants. The isolated PVY or PVX RNA is found to be biologically contained under natural conditions.

Example 21

Preparation of Chimeric Nucleotide Sequence Containing the Tyrosinase Coding Sequence The coding sequence for tyrosinase is isolated from *Streptococcus antibioticus,* by digestion with BclI followed by 5'-exonuclease digestion to the start codon. Alternatively, a restriction site is engineered adjacent the start codon of the tyrosinase coding sequence by site-directed oligonucleotide mutagenesis. Digestion with the appropriate restriction enzyme yields the coding sequence for tyrosinase. The fragment containing the tyrosinase coding sequence is isolated and cloned adjacent the promoter of the viral coat protein gene in the vectors prepared in Examples 17, 18 and 19.

Example 22

Preparation of a Non-Infective Eastern Equine Encephalomyelitis Virus Nucleotide Sequence A full-length cDNA copy of the Eastern Equine Encephalomyelitis Virus (EEEV) genome is prepared and inserted into the PstI site of pUC18 as described by Chang, G-J. J. et al., *J. Gen. Virol.*, 68, 2129 (1987). The sequence for the viral coat protein and its adjacent E1 and E2 glycoprotein transmissibility factors are located on the region corresponding to the 26S RNA region. The vector containing the cDNA copy of the EEEV genome is digested with the appropriate restriction enzymes and exonucleases to delete the coding sequence of the coat protein and the E1 and E2 proteins (structural protein coding sequence).

For example, the structural protein coding sequence is removed by partial digestion with MboI, followed by religation to remove a vital portion of the structural gene. Alternatively, the vector is cut at the 3' end of the viral structural gene. The viral DNA is sequentially removed by digestion with Bal31 or Micrococcal S1 nuclease up through the start codon of the structural protein sequence. The DNA sequence containing the sequence of the viral 3' tail is then ligated to the remaining 5'-end. The deletion of the coding sequence for the structural proteins is confirmed by isolating EEEV RNA and using it to infect an equine cell culture. The isolated EEEV RNA is found to be non-infective under natural conditions.

Alternatively only the coding sequence for the coat protein is deleted and the sequence for the E1 and E2 glycoproteins remain in the vector containing the cDNA copy of the EEEV genome. In this case, the coat protein coding sequence is removed by partial digestion with MboI followed by religation to reattach the 3'-tail of the virus. This will remove a vital portion of the coat protein gene.

A second alternative method for removing only the coat protein sequence is to cut the vector at the 3'-end of the viral coat protein gene. The viral DNA is removed by digestion with Bal31 or Micrococcal S1 nuclease up through the start codon of the coat protein sequence. The synthetic DNA sequence containing the sequence of the 3'-tail is then ligated to the remaining 5'-end.

The deletion of the coding sequence for the coat protein is confirmed by isolating EEEV RNA and using it to infect an equine cell culture. The isolated EEEV RNA is found to be non-infective under natural conditions.

Example 23

Preparation of a Non-Transmissible Sindbis Virus Nucleotide Sequence

A full-length NDA copy of the Sindbis virus genome is prepared and inserted into the SmaI site of a plasmid derived from pBR322 as described by Lindquist, B. H. et al., *Virology*, 151, 10 (1986). The sequence for the viral coat protein and the adjacent E1 and E2 glycoprotein transmissibility factors are located on the region corresponding to the 26S RNA region. The vector containing the cDNA copy of the Sindbis virus genome is digested with the appropriate restriction enzymes and exonucleases to delete the coding sequence for the structural proteins.

For example, the structural protein coding sequence is removed by partial digestion with BinI, followed by religation to remove a vital portion of the structural gene. Alternatively, the vector is cut at the 3' end of the viral nucleic acid. The viral DNA is removed by digestion with Bal31 or Micrococcal S1 nuclease up through the start codon of the structural protein sequence. The synthetic DNA sequence of the viral 3'-tail is then ligated to the remaining 5'-end. The deletion of the coding sequence for the structural proteins is confirmed by isolating Sindbus RNA and using it to infect an avian cell culture. The isolated Sindbis RNA is found to be non-infective under natural conditions.

Alternatively only the coding sequence for the coat protein is deleted and the sequence for the E1 and E2 glycoproteins remain in the vector containing the cDNA copy of the Sindbis genome. In this case, the coat protein coding sequence is removed by partial digestion with AflII followed by religation to reattach the 3'-tail of the virus.

A second alternative method for removing only the coat protein sequence is to cut the vector at the 3'-end of the viral nucleic acid. The viral DNA is removed by digestion with Bal31 or Micrococcal S1 nuclease up through the start codon of the coat protein sequence (the same start codon as for the sequence for all the structural proteins). The synthetic DNA sequence containing the sequence of the 3'-tail is then ligated to the remaining 5'-end.

The deletion of the coding sequence for the coat protein is confirmed by isolating Sindbis RNA and using it to infect an avian cell culture. The isolated Sindbis RNA is found to be non-infective under natural conditions.

Example 24

Preparation of a Non-Transmissible Western Equine Encephalomyelitis Virus Nucleotide Sequence A full-length cDNA copy of the Western Equine Encephalomyelitis Virus (WEEV) genome is prepared as described by Hahn, C. S. et al., *Proc. Natl. Acad. Sci. USA* 85, 5997 (1988). The sequence for the viral coat protein and its adjacent E1 and E2 glycoprotein transmissibility factors are located on the region corresponding to the 26S RNA region. The vector containing the cDNA copy of the wEEV genome is digested with the appropriate restriction enzymes and exonucleases to delete the coding sequence of the coat protein and the E1 and E2 proteins (structural protein coding sequence).

For example, the structural protein coding sequence is removed by partial digestion with NacI, followed by religation to remove a vital portion of the structural protein sequence. Alternatively, the vector is cut at the 3' end of the structural protein DNA sequence. The viral DNA is removed by digestion with Bal31 or Micrococcal S1 nuclease up through the start codon of the structural protein sequence. The DNA sequence of the viral 3'-tail is then ligated to the remaining 5'-end. The deletion of the coding sequence for the structural proteins is confirmed by isolating WEEV RNA and using it to infect a Vero cell culture. The isolated WEEV RNA is found to be non-infective under natural conditions.

Alternatively only the coding sequence for the coat protein is deleted and the sequence for the E1 and E2 glycoproteins remain in the vector containing the cDNA copy of the WEEV genome. In this case, the coat protein coding sequence is removed by partial digestion with HgiAI followed by religation to reattach the 3'-tail of the virus.

A second alternative method for removing only the coat protein sequence is to cut the vector at the 3'-end of the viral coat protein sequence. The viral DNA is removed by digestion with Bal31 or Micrococcal S1 nuclease up through the a vital portion of the coat protein sequence. The DNA sequence containing the sequence of the 3'-tail is then ligated to the remaining 5'-end.

The deletion of the coding sequence for the coat protein is confirmed by isolating WEEV RNA and using it to infect a Vero cell culture. The isolated WEEV RNA is found to be non-infective, i.e. biologically contained, under natural conditions.

Example 25

Preparation of Chimeric Nucleotide Sequence Containing the Tyrosinase Coding Sequence The coding sequence for tyrosinase is isolated as described in Example 21, and cloned adjacent the promoter of the viral coat protein gene in the vectors prepared in Examples 22, 23 and 24.

Example 26

Preparation of Virus Containing Tyrosinase

A promoter is attached to the chimeric nucleotide sequence of Example 25 in accordance with conventional techniques. The resulting vector is used to transform the production cell which is yeast in this instance.

A second vector is prepared by inserting the viral structure protein coding sequence, isolated in Examples 22, 23 and 24, adjacent the ADCI promoter in the vector pAH5 (Ammerer, G., *Meth. Enzymol.*, 101, 192 (1983)). This vector is used to transform the production cells having a vector with the compatible chimeric nucleotide sequence. The production cells are grown and the resultant viruses are isolated. Alternatively, the second vector is used to transform a second strain of yeast which produces the structural proteins. The structural proteins and the viral vector are then combined to form the virus.

Example 27

Preparation of Melanin In Vitro

The viruses isolated in Example 26, made by the combination of chimeric nucleotide sequence and coat protein are used to infect equine cell cultures (viruses based on EEEV an WEEV) or avian cell cultures (viruses based on Sindbis virus). The infected cell cultures are grown under normal cell culture growth conditions. The cells produce tryrosinase which reacts with the components present in the cells to produce intermediates which are then converted to melanin. The melanin is isolated by conventional techniques.

Example 28

Preparation of Melanin In Vitro

The viruses isolated in Example 27, made by the combination of chimeric nucleotide sequence and structural proteins (coat protein, E1 glycoprotein and E2 glycoprotein) are used to infect horses (viruses based on EEEV and WEEV) or chickens (viruses based on Sindbis virus) The infected animals are maintained under normal conditions (i.e. feeding, exercise, sleep etc.) The animals produce tyrosinase which reacts with components present in the animals to produce intermediates which are then converted to melanin. The melanin is isolated by conventional techniques.

Example 29

Preparation of a Chimeric Nucleotide Sequence Containing Human Tissue Plasminogen Activator (t-PA) Coding Sequence The coding sequence for human tissue plasminogen activator is isolated from plasmid pt-PAtrp12, ATCC No. 40404 (U.S. Pat. No. 4,766,075) and cloned adjacent the promoter of the viral coat protein gene in the vectors prepared in Examples 22, 23 or 24.

Example 30

Preparation of Virus Containing a Coding Sequence for Human t-PA

A virus containing the coding sequence for human t-PA is prepared in accordance with the procedures described in Example 26.

Example 31

Preparation of Human t-PA In Vitro

The viruses isolated in Example 30, made by the combination of chimeric nucleotide sequence and coat protein are used to infect equine cell cultures (viruses based on EEEV and WEEV) or avian cell cultures (viruses based on Sindbis virus). The infected cell cultures are grown under normal cell culture growth conditions. The cells produce human t-PA which is isolated by conventional techniques.

The viruses isolated in Example 30, made by the combination of chimeric nucleotide sequence and structural proteins (coat protein, E1 glycoprotein and E2 glycoprotein) are used to infect horses (viruses based on EEEV and WEEV) or chickens (viruses based on Sindbis virus). The infected animals are maintained under normal conditions (i.e. feeding, exercise, sleep etc.) The animals produce human t-PA which is isolated by conventional techniques.

Example 33

Preparation of a Non-Infective Human Phinovirus 2 Nucleotide Sequence

A full length cDNA copy of the human rhinovirus 2 (HPV2) genome is prepared, and inserted into the PstI site of plasmid pUC9 as described by Skern, T. et al., *Nucleic Acids Res.*, 13, 2111 (1985). The nucleotide sequence for the viral coat protein VP1 is located at position 2644 of the genome. The vector containing the DNA copy of the HRV2 genome is digested with the appropriate restriction enzymes and exonucleases to delete the coat protein coding sequence.

For example, the coat protein coding sequence is removed by partial digestion with an appropriate restriction endonuclease, followed by religation to remove a vital portion of the coat protein sequence. Alternatively, the vector is cut at the 3'-end of the viral coat protein gene. The viral DNA is removed by digestion with Bal31 or Micrococcal 51 nuclease up through the start codon (promoter) of the coat protein sequence. The synthetic DNA sequence containing the sequence of the viral 3'-tail is then ligated to the remaining 5'-end. The deletion of the coding sequence for the coat protein is confirmed by isolating HRV2 RNA and using it to infect a human cell culture. The isolated HPV2 RNA is found to the non-infective under natural conditions.

Example 34

Preparation of Chimeric Nucleotide Sequence Containing the Tyrosinase Coding Sequence The coding sequence for tyrosinase is isolated as described in Example 21, and cloned adjacent the promoter of the viral coat protein gene in the vectors prepared in Example 33.

Example 35

Preparation of Virus Containing Tyrosinase

A virus based on HRV2 containing a tyrosinase coding sequence is prepared as described in Example 26 using the starting materials produced in Examples 33 and 34.

Example 36

Preparation of Melanin

The viruses isolated in Example 35 are used to infect human cell cultures. The infected cells produce tyrosinase which reacts with the components present in the human cells to produce intermediates which are then converted to melanin in the cells. The melanin is isolated by conventional techniques.

Example 37

Preparation of a Chimeric Nucleotide Sequence Containing a Human t-PA Coding Sequence The coding sequence for human t-PA is isolated as described in Example 29, and cloned adjacent the promoter of the viral coat protein gene in the vectors prepared in Example 33.

Example 38

Preparation of Virus Containing a Coding Sequence for Human t-PA

A virus containing the coding sequence for human t-PA is prepared in accordance with the procedures of Example 35.

Example 39

Preparation of Human t-PA

The viruses isolated in Example 38 are used to infect human cell cultures. The infected cells are grown under normal growth conditions. The cells produce human t-PA which is isolated by conventional techniques.

Example 40

Preparation of a Non-Infective Poliovirus Type 2 Nucleotide Sequence

A full-length cDNA copy of the poliovirus type 2 (PV2) genome is prepared, and inserted into the HindIII site of plasmid pBR322 as described by Toyoda, H. et al., *J. Mol. Biol.*, 174, 561 (1984). The nucleotide sequence of the viral coat protein VP1 is located at position 2499 of the genome. The vector containing the DNA copy of the PV2 genome is digested with the appropriate restriction enzymes and exonucleases to delete the coat protein coding sequence. It is important that the protease digestion sequences are left intact.

For example, a part of the coat protein-coding sequence is removed by partial digestion with an appropriate restriction endonuclease, followed by religation to reattach the 3'-tail of the virus. The deletion of the coding sequence for the coat protein is confirmed by isolating PV2 ENA and using it to infect spinner-cultured HeLa S3 cells. The isolated PV2 PNA is found to be non-infective, i.e. biologically contained, under natural conditions.

Example 41

Preparation of Chimeric Nucleotide Sequence Containing the Tyrosinase Coding Sequence The coding sequence for tyrosinase is isolated as described in Example 21, and cloned adjacent the promoter of the viral coat protein gene in the vectors prepared in Example 40.

Example 42

Preparation of Virus Containing Tyrosinase

A virus based on PV2 containing a coding sequence for tyrosinase is prepared as described in Example 26 using the starting materials produced in Example 40 and 41.

Example 43

Preparation of Melanin

The viruses isolated in Example 42 are used to infect spinner-cultured HeLa S3 cells. The infected cells produce tyrosinase which reacts with the components present in the cells to produce intermediates which are then converted to melanin in the cells. The melanin is isolated by conventional techniques.

Example 44

Preparation of a Chimeric Nucleotide Sequence Containing a Human t-PA Coding Sequence The coding sequence for human t-PA is isolated as described in Example 29, and cloned adjacent the promoter of the viral coat protein gene in the vectors prepared in Example 40.

Example 45

Preparation of Virus Containing Human t-PA Coding Sequence

A virus containing the coding sequence for human t-PA prepared in accordance with the procedures of Example 42.

Example 46

Preparation of Human t-PA

The viruses of Example 45 are used to infect spinner-cultured HeLa 53 cells. The infected cells are grown under normal growth conditions. The cells produce human t-PA which is isolated by conventional techniques.

Example 47

Preparation of a Non-Infective Simian Virus 40 Nucleotide Sequence

A full-length cDNA copy of the Simian virus 40 (SV40) genome is prepared, and inserted into the AccI site of plasmid pCW18 as described by Wychowski, C. et al., *J. Virol.* 61, 3862 (1987). The nucleotide sequence of the viral coat protein VP1 is located between position 1488 and 2574 of the genome. The vector containing the DNA copy of the SV40 genome is digested with the appropriate restriction enzymes and exonucleases to delete the coat protein coding sequence.

For example, the VP1 coat protein coding sequence is removed by partial digestion with BamHI nuclease, and then treated with EcoRI, filled in with Klenow enzyme and recircularized. The deletion of the coding sequence for the coat protein VP1 is confirmed by isolating SV40 RNA and using it to infect simian cell cultures. The isolated SV40 RNA is found to be non-infective, i.e. biologically contained, under natural conditions.

Example 48

Preparation of Chimeric Nucleotide Sequence Containing the Tyrosinase Coding Sequence The coding sequence for tyrosinase is isolated as described in Example 21, and cloned adjacent the promoter of the viral coat protein gene in the vectors prepared in Example 47.

Example 49

Preparation of Virus Containing Tyrosinase

A virus containing a tyrosinase coding sequence and based on SV40 is prepared as described in Example 26. The chimeric nucleotide sequence of Example 48 and the coat protein coding sequence isolated in Example 47 are utilized.

Example 50

Preparation of Melanin

The viruses isolated in Example 49 are used to infect simian cell cultures. The infected cells produce tyrosinase which reacts with the components present in the cells to produce intermediates which are then converted to melanin in the cells. The melanin is isolated by conventional techniques.

Example 51

Preparation of a Chimeric Nucleotide Sequence Containing a Human t-PA Coding Sequence The coding sequence for cyclodextrin glucotransferase is isolated as described in Example 29, and cloned adjacent the promoter of the viral coat protein gene in the vectors prepared in Example 47.

Example 52

Preparation of Virus Containing Human t-PA Coding Sequence

A virus containing the coding sequence for human t-PA is prepared in accordance with the procedures of Example 49.

Example 53

Preparation of Human t-PA

The viruses of Example 52 are used to infect simian cell cultures. The infected cells are grown under normal growth conditions. The cells produce human t-PA which is isolated by conventional techniques.

The following plasmids have been deposited at the American Type Culture Collection (ATCC), Rockville, Md., USA, under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such plasmids is not to be construed as a license to practice the invention in contravention of the rights granted under the authority of any government in accordance with its patent laws.

The deposited cultures have been assigned the indicated ATCC deposit numbers:

Plasmid ATCC No.
pTB2 75280
pTBU5 75281

Pursuant to 37 C.F.R. §1.808, Applicants agree that all restrictions imposed by the depositor on the availability to the public of the deposited plasmids will be irrevocably removed upon the granting of a patent on the present application.

While the invention has been disclosed in this patent application by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims.

What is claimed is:

1. A recombinant virus selected from the group consisting of Eastern Equine Encephalomyelitis Virus, Western Equine Encephalomyelitis Virus, Rhinovirus, Poliovirus, Simian Virus, and Adenovirus, comprising:
 a first viral subgenomic promoter that is native to said virus;
 a nucleic acid sequence encoding a coat protein that is native to said virus operably linked to the first viral subgenomic promoter;
 a second viral subgenomic promoter that is non-native to said virus;
 a second nucleic acid sequence encoding a protein that is non-native to said virus operably linked to the second viral subgenomic promoter;
 wherein the first and second viral subgenomic promoters possess heterologous nucleic acid sequences relative to each other,
 a third viral subgenomic promoter;
 and a third nucleic acid sequence encoding a protein operably linked to the third viral subgenomic promoter;
 wherein the third subgenomic promoter cannot recombine with the first and second viral subgenomic promoters.

2. A process for transcribing a nucleic acid sequence in an animal cell culture comprising:
 (a) infecting an animal cell culture with a recombinant virus selected from the group consisting of Eastern Equine Encephalomyelitis Virus, Western Equine Encephalomyelitis Virus, Rhinovirus, Poliovirus, Simian Virus, and Adenovirus, said recombinant virus comprising:
  a first viral subgenomic promoter that is native to said virus;
  a nucleic acid sequence encoding a viral coat protein that is native to said virus operably linked to the first viral subgenomic promoter;
  a second viral subgenomic promoter that is non-native to said virus; and
  a second nucleic acid sequence encoding a protein that is non-native to said virus operably linked to the second viral subgenomic promoter;
  wherein the first and second viral subgenomic promoters possess heterologous nucleic acid sequences relative to each other; and
 (b) growing the animal cell culture such that the protein encoded by the second nucleic acid sequence is transcribed;
 wherein the protein encoded by the second nucleic acid is selected from the group consisting of IL-1, IL-2, IL-3, IL-4, IL-5, IL-6, IL-7, IL-8, IL-9, IL-10, IL-11, IL-12, EPO, G-CSF, M-CSF, Factor VIII, Factor IX, tissue plasminogen activator, human growth hormone, receptors, receptor antagonists, antibodies, neuro-polypeptides, melanin, lipase, hormones, pharmaceuticals, antibiotics, vaccines, and insulin.

3. The process according to claim 2, which further comprises isolating the protein encoded by the second nucleic acid.

* * * * *

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: Amino-terminal end of non-native protein
      Xaa = Any desired amino acid
<220> FEATURE:
<221> NAME/KEY: VARIANT
```

-continued

<222> LOCATION: (2)...(2)
<223> OTHER INFORMATION: Xaa= Any desired amino acid

<400> SEQUENCE: 1

Pro Xaa Gly Pro
 1

<210> SEQ ID NO 2
<211> LENGTH: 13
<212> TYPE: DNA
<213> ORGANISM: Artificial Sequence
<220> FEATURE:
<223> OTHER INFORMATION: linear genomic DNA

<400> SEQUENCE: 2
gggtacctgg gcc 13

<210> SEQ ID NO 3
<211> LENGTH: 886
<212> TYPE: DNA
<213> ORGANISM: Chinese Cucumber
<220> FEATURE:
<221> NAME/KEY: CDS
<222> LOCATION: (8)...(877)
<223> OTHER INFORMATION: Clone:alpha-trichosanthin

<400> SEQUENCE: 3

```
ctcgagg atg atc aga ttc tta gtc ctc tct ttg cta att ctc acc ctc       49
        Met Ile Arg Phe Leu Val Leu Ser Leu Leu Ile Leu Thr Leu
         1               5                  10 ttc cta aca act cct gct gtg gag ggc gat gtt agc ttc cgt tta tca       97
Phe Leu Thr Thr Pro Ala Val Glu Gly Asp Val Ser Phe Arg Leu Ser
 15                  20                  25                  30 ggt gca aca agc agt tcc tat gga gtt ttc att tca aat ctg aga aaa      145
Gly Ala Thr Ser Ser Ser Tyr Gly Val Phe Ile Ser Asn Leu Arg Lys
                 35                  40                  45 gct ctt cca aat gaa agg aaa ctg tac gat atc cct ctg tta cgt tcc      193
Ala Leu Pro Asn Glu Arg Lys Leu Tyr Asp Ile Pro Leu Leu Arg Ser
             50                  55                  60 tct ctt cca ggt tct caa cgc tac gca ttg atc cat ctc aca aat tac      241
Ser Leu Pro Gly Ser Gln Arg Tyr Ala Leu Ile His Leu Thr Asn Tyr
         65                  70                  75 gcc gat gaa acc att tca gtg gcc ata gac gta acg aac gtc tat att      289
Ala Asp Glu Thr Ile Ser Val Ala Ile Asp Val Thr Asn Val Tyr Ile
     80                  85                  90 atg gga tat cgc gct ggc gat aca tcc tat ttt ttc aac gag gct tct      337
Met Gly Tyr Arg Ala Gly Asp Thr Ser Tyr Phe Phe Asn Glu Ala Ser
 95                 100                 105                 110 gca aca gaa gct gca aaa tat gta ttc aaa gac gct atg cga aaa gtt      385
Ala Thr Glu Ala Ala Lys Tyr Val Phe Lys Asp Ala Met Arg Lys Val
                115                 120                 125 acg ctt cca tat tct ggc aat tac gaa agg ctt caa act gct gcg ggc      433
Thr Leu Pro Tyr Ser Gly Asn Tyr Glu Arg Leu Gln Thr Ala Ala Gly
            130                 135                 140 aaa ata agg gaa aat att ccg ctt gga ctc cca gct ttg gac agt gcc      481
Lys Ile Arg Glu Asn Ile Pro Leu Gly Leu Pro Ala Leu Asp Ser Ala
        145                 150                 155 att acc act ttg ttt tac tac aac gcc aat tct gct gcg tcg gca ctt      529
Ile Thr Thr Leu Phe Tyr Tyr Asn Ala Asn Ser Ala Ala Ser Ala Leu
    160                 165                 170 atg gta ctc att cag tcg acg tct gag gct gcg agg tat aaa ttt att      577
Met Val Leu Ile Gln Ser Thr Ser Glu Ala Ala Arg Tyr Lys Phe Ile
175                 180                 185                 190
```

-continued

```
gag caa caa att ggg aag cgc gtt gac aaa acc ttc cta cca agt tta      625
Glu Gln Gln Ile Gly Lys Arg Val Asp Lys Thr Phe Leu Pro Ser Leu
                195                 200                 205 gca att ata agt ttg gaa aat agt tgg tct gct ctc tcc aag caa att      673
Ala Ile Ile Ser Leu Glu Asn Ser Trp Ser Ala Leu Ser Lys Gln Ile
            210                 215                 220 cag ata gcg agt act aat aat gga cag ttt gaa act cct gtt gtg ctt      721
Gln Ile Ala Ser Thr Asn Asn Gly Gln Phe Glu Thr Pro Val Val Leu
        225                 230                 235 ata aat gct caa aac caa cga gtc atg ata acc aat gtt gat gct gga      769
Ile Asn Ala Gln Asn Gln Arg Val Met Ile Thr Asn Val Asp Ala Gly
    240                 245                 250 gtt gta acc tcc aac atc gcg ttg ctg ctg aat cga aac aat atg gca      817
Val Val Thr Ser Asn Ile Ala Leu Leu Leu Asn Arg Asn Asn Met Ala
255                 260                 265                 270 gcc atg gat gac gat gtt cct atg aca cag agc ttt gga tgt gga agt      865
Ala Met Asp Asp Asp Val Pro Met Thr Gln Ser Phe Gly Cys Gly Ser
                275                 280                 285 tat gct att tag taactcgag                                            886
Tyr Ala Ile  *

<210> SEQ ID NO 4
<211> LENGTH: 289
<212> TYPE: PRT
<213> ORGANISM: Chinese Cucumber alpha-trichosanthin

<400> SEQUENCE: 4

Met Ile Arg Phe Leu Val Leu Ser Leu Leu Ile Leu Thr Leu Phe Leu
 1               5                  10                  15

Thr Thr Pro Ala Val Glu Gly Asp Val Ser Phe Arg Leu Ser Gly Ala
            20                  25                  30

Thr Ser Ser Ser Tyr Gly Val Phe Ile Ser Asn Leu Arg Lys Ala Leu
        35                  40                  45

Pro Asn Glu Arg Lys Leu Tyr Asp Ile Pro Leu Leu Arg Ser Ser Leu
    50                  55                  60

Pro Gly Ser Gln Arg Tyr Ala Leu Ile His Leu Thr Asn Tyr Ala Asp
65                  70                  75                  80

Glu Thr Ile Ser Val Ala Ile Asp Val Thr Asn Val Tyr Ile Met Gly
                85                  90                  95

Tyr Arg Ala Gly Asp Thr Ser Tyr Phe Phe Asn Glu Ala Ser Ala Thr
            100                 105                 110

Glu Ala Ala Lys Tyr Val Phe Lys Asp Ala Met Arg Lys Val Thr Leu
        115                 120                 125

Pro Tyr Ser Gly Asn Tyr Glu Arg Leu Gln Thr Ala Ala Gly Lys Ile
    130                 135                 140

Arg Glu Asn Ile Pro Leu Gly Leu Pro Ala Leu Asp Ser Ala Ile Thr
145                 150                 155                 160

Thr Leu Phe Tyr Tyr Asn Ala Asn Ser Ala Ala Ser Ala Leu Met Val
                165                 170                 175

Leu Ile Gln Ser Thr Ser Glu Ala Ala Arg Tyr Lys Phe Ile Glu Gln
            180                 185                 190

Gln Ile Gly Lys Arg Val Asp Lys Thr Phe Leu Pro Ser Leu Ala Ile
        195                 200                 205

Ile Ser Leu Glu Asn Ser Trp Ser Ala Leu Ser Lys Gln Ile Gln Ile
    210                 215                 220

Ala Ser Thr Asn Asn Gly Gln Phe Glu Thr Pro Val Val Leu Ile Asn
```

```
                225                 230                 235                 240
Ala Gln Asn Gln Arg Val Met Ile Thr Asn Val Asp Ala Gly Val Val
                    245                 250                 255

Thr Ser Asn Ile Ala Leu Leu Leu Asn Arg Asn Asn Met Ala Ala Met
            260                 265                 270

Asp Asp Asp Val Pro Met Thr Gln Ser Phe Gly Cys Gly Ser Tyr Ala
        275                 280                 285

Ile

<210> SEQ ID NO 5
<211> LENGTH: 1452
<212> TYPE: DNA
<213> ORGANISM: Oryza sativa
<220> FEATURE:
<221> NAME/KEY: CDS
<222> LOCATION: (12)...(1316)
<223> OTHER INFORMATION: CLONE: alpha-amylase
      linear DNA (genomic)

<400> SEQUENCE: 5
cctcgaggtg c atg cag gtg ctg aac acc atg gtg aac aaa cac ttc ttg        50
             Met Gln Val Leu Asn Thr Met Val Asn Lys His Phe Leu
              1               5                  10 tcc ctt tcg gtc ctc atc gtc ctc ctt ggc ctc tcc tcc aac ttg aca        98
Ser Leu Ser Val Leu Ile Val Leu Leu Gly Leu Ser Ser Asn Leu Thr
    15                  20                  25 gcc ggg caa gtc ctg ttt cag gga ttc aac tgg gag tcg tgg aag gag       146
Ala Gly Gln Val Leu Phe Gln Gly Phe Asn Trp Glu Ser Trp Lys Glu
 30                  35                  40                  45 aat ggc ggg tgg tac aac ttc ctg atg ggc aag gtg gac gac atc gcc       194
Asn Gly Gly Trp Tyr Asn Phe Leu Met Gly Lys Val Asp Asp Ile Ala
                 50                  55                  60 gca gcc ggc atc acc cac gtc tgg ctc cct ccg ccg tct cac tct gtc       242
Ala Ala Gly Ile Thr His Val Trp Leu Pro Pro Pro Ser His Ser Val
             65                  70                  75 ggc gag caa ggc tac atg cct ggg cgg ctg tac gat ctg gac gcg tct       290
Gly Glu Gln Gly Tyr Met Pro Gly Arg Leu Tyr Asp Leu Asp Ala Ser
         80                  85                  90 aag tac ggc aac gag gcg cag ctc aag tcg ctg atc gag gcg ttc cat       338
Lys Tyr Gly Asn Glu Ala Gln Leu Lys Ser Leu Ile Glu Ala Phe His
     95                  100                 105 ggc aag ggc gtc cag gtg atc gcc gac atc gtc atc aac cac cgc acg       386
Gly Lys Gly Val Gln Val Ile Ala Asp Ile Val Ile Asn His Arg Thr
110                 115                 120                 125 gcg gag cac aag gac ggc cgc ggc atc tac tgc ctc ttc gag ggc ggg       434
Ala Glu His Lys Asp Gly Arg Gly Ile Tyr Cys Leu Phe Glu Gly Gly
                130                 135                 140 acg ccc gac tcc cgc ctc gac tgg ggc ccg cac atg atc tgc cgc gac       482
Thr Pro Asp Ser Arg Leu Asp Trp Gly Pro His Met Ile Cys Arg Asp
            145                 150                 155 gac ccc tac ggc gat ggc acc ggc aac ccg gac acc ggc gcc gac ttc       530
Asp Pro Tyr Gly Asp Gly Thr Gly Asn Pro Asp Thr Gly Ala Asp Phe
        160                 165                 170 gcc gcc gcg ccg gac atc gac cac ctc aac aag cgc gtc cag cgg gag       578
Ala Ala Ala Pro Asp Ile Asp His Leu Asn Lys Arg Val Gln Arg Glu
    175                 180                 185 ctc att ggc tgg ctc gac tgg ctc aag atg gac atc ggc ttc gac gcg       626
Leu Ile Gly Trp Leu Asp Trp Leu Lys Met Asp Ile Gly Phe Asp Ala
190                 195                 200                 205 tgg cgc ctc gac ttc gcc aag ggc tac tcc gcc gac atg gca aag atc       674
```

-continued

```
Trp Arg Leu Asp Phe Ala Lys Gly Tyr Ser Ala Asp Met Ala Lys Ile
                205                 210                 215                 220 tac atc gac gcc acc gag ccg agc ttc gcc gtg gcc gag ata tgg acg           722
Tyr Ile Asp Ala Thr Glu Pro Ser Phe Ala Val Ala Glu Ile Trp Thr
                225                 230                 235 tcc atg gcg aac ggc ggg gac ggc aag ccg aac tac gac cag aac gcg           770
Ser Met Ala Asn Gly Gly Asp Gly Lys Pro Asn Tyr Asp Gln Asn Ala
                240                 245                 250 cac cgg cag gag ctg gtc aac tgg gtc gat cgt gtc ggc ggc gcc aac           818
His Arg Gln Glu Leu Val Asn Trp Val Asp Arg Val Gly Gly Ala Asn
                255                 260                 265 agc aac ggc acg gcg ttc gac ttc acc acc aag ggc atc ctc aac gtc           866
Ser Asn Gly Thr Ala Phe Asp Phe Thr Thr Lys Gly Ile Leu Asn Val
270                 275                 280                 285 gcc gtg gag ggc gag ctg tgg cgc ctc cgc ggc gag gac ggc aag gcg           914
Ala Val Glu Gly Glu Leu Trp Arg Leu Arg Gly Glu Asp Gly Lys Ala
                290                 295                 300 ccc ggc atg atc ggg tgg tgg ccg gcc aag gcg acg acc ttc gtc gac           962
Pro Gly Met Ile Gly Trp Trp Pro Ala Lys Ala Thr Thr Phe Val Asp
                305                 310                 315 aac cac gac acc ggc tcg acg cag cac ctg tgg ccg ttc ccc tcc gac          1010
Asn His Asp Thr Gly Ser Thr Gln His Leu Trp Pro Phe Pro Ser Asp
                320                 325                 330 aag gtc atg cag ggc tac gca tac atc ctc acc cac ccc ggc aac cca          1058
Lys Val Met Gln Gly Tyr Ala Tyr Ile Leu Thr His Pro Gly Asn Pro
                335                 340                 345 tgc atc ttc tac gac cat ttc ttc gat tgg ggt ctc aag gag gag atc          1106
Cys Ile Phe Tyr Asp His Phe Phe Asp Trp Gly Leu Lys Glu Glu Ile
350                 355                 360                 365 gag cgc ctg gtg tca atc aga aac cgg cag ggg atc cac ccg gcg agc          1154
Glu Arg Leu Val Ser Ile Arg Asn Arg Gln Gly Ile His Pro Ala Ser
                370                 375                 380 gag ctg cgc atc atg gaa gct gac agc gat ctc tac ctc gcg gag atc          1202
Glu Leu Arg Ile Met Glu Ala Asp Ser Asp Leu Tyr Leu Ala Glu Ile
                385                 390                 395 gat ggc aag gtg atc aca aag att gga cca aga tac gac gtc gaa cac          1250
Asp Gly Lys Val Ile Thr Lys Ile Gly Pro Arg Tyr Asp Val Glu His
                400                 405                 410 ctc atc ccc gaa ggc ttc cag gtc gtc gcg cac ggt gat ggc tac gca          1298
Leu Ile Pro Glu Gly Phe Gln Val Val Ala His Gly Asp Gly Tyr Ala
415                 420                 425 atc tgg gag aaa atc tga gcgcacgatg acagactct cagtttagca                  1346
Ile Trp Glu Lys Ile *
430 gatttaacct gcgatttta ccctgaccgg tatacgtata tacgtgccgg caacgagctg         1406 tatccgatcc gaattacgga tgcaattgtc cacgaagtcc tcgagg                       1452
```

<210> SEQ ID NO 6
<211> LENGTH: 434
<212> TYPE: PRT
<213> ORGANISM: Oryza sativa
<220> FEATURE:
<223> OTHER INFORMATION: CLONE: alpha-amylase
       protein

<400> SEQUENCE: 6

```
Met Gln Val Leu Asn Thr Met Val Asn Lys His Phe Leu Ser Leu Ser
1               5                   10                  15

Val Leu Ile Val Leu Leu Gly Leu Ser Ser Asn Leu Thr Ala Gly Gln
                20                  25                  30
```

-continued

```
Val Leu Phe Gln Gly Phe Asn Trp Glu Ser Trp Lys Glu Asn Gly Gly
             35                  40                  45

Trp Tyr Asn Phe Leu Met Gly Lys Val Asp Asp Ile Ala Ala Ala Gly
         50                  55                  60

Ile Thr His Val Trp Leu Pro Pro Ser His Ser Val Gly Glu Gln
 65                  70                  75                  80

Gly Tyr Met Pro Gly Arg Leu Tyr Asp Leu Asp Ala Ser Lys Tyr Gly
                 85                  90                  95

Asn Glu Ala Gln Leu Lys Ser Leu Ile Glu Ala Phe His Gly Lys Gly
                100                 105                 110

Val Gln Val Ile Ala Asp Ile Val Ile Asn His Arg Thr Ala Glu His
            115                 120                 125

Lys Asp Gly Arg Gly Ile Tyr Cys Leu Phe Glu Gly Gly Thr Pro Asp
130                 135                 140

Ser Arg Leu Asp Trp Gly Pro His Met Ile Cys Arg Asp Asp Pro Tyr
145                 150                 155                 160

Gly Asp Gly Thr Gly Asn Pro Asp Thr Gly Ala Asp Phe Ala Ala Ala
                165                 170                 175

Pro Asp Ile Asp His Leu Asn Lys Arg Val Gln Arg Glu Leu Ile Gly
            180                 185                 190

Trp Leu Asp Trp Leu Lys Met Asp Ile Gly Phe Asp Ala Trp Arg Leu
        195                 200                 205

Asp Phe Ala Lys Gly Tyr Ser Ala Asp Met Ala Lys Ile Tyr Ile Asp
        210                 215                 220

Ala Thr Glu Pro Ser Phe Ala Val Ala Glu Ile Trp Thr Ser Met Ala
225                 230                 235                 240

Asn Gly Gly Asp Gly Lys Pro Asn Tyr Asp Gln Asn Ala His Arg Gln
                245                 250                 255

Glu Leu Val Asn Trp Val Asp Arg Val Gly Gly Ala Asn Ser Asn Gly
            260                 265                 270

Thr Ala Phe Asp Phe Thr Thr Lys Gly Ile Leu Asn Val Ala Val Glu
        275                 280                 285

Gly Glu Leu Trp Arg Leu Arg Gly Glu Asp Gly Lys Ala Pro Gly Met
    290                 295                 300

Ile Gly Trp Trp Pro Ala Lys Ala Thr Thr Phe Val Asp Asn His Asp
305                 310                 315                 320

Thr Gly Ser Thr Gln His Leu Trp Pro Phe Pro Ser Asp Lys Val Met
                325                 330                 335

Gln Gly Tyr Ala Tyr Ile Leu Thr His Pro Gly Asn Pro Cys Ile Phe
            340                 345                 350

Tyr Asp His Phe Phe Asp Trp Gly Leu Lys Glu Glu Ile Glu Arg Leu
        355                 360                 365

Val Ser Ile Arg Asn Arg Gln Gly Ile His Pro Ala Ser Glu Leu Arg
    370                 375                 380

Ile Met Glu Ala Asp Ser Asp Leu Tyr Leu Ala Glu Ile Asp Gly Lys
385                 390                 395                 400

Val Ile Thr Lys Ile Gly Pro Arg Tyr Asp Val Glu His Leu Ile Pro
                405                 410                 415

Glu Gly Phe Gln Val Val Ala His Gly Asp Gly Tyr Ala Ile Trp Glu
            420                 425                 430

Lys Ile
```

-continued

```
<210> SEQ ID NO 7
<211> LENGTH: 709
<212> TYPE: DNA
<213> ORGANISM: Homo sapiens
<220> FEATURE:
<221> NAME/KEY: transit_peptide
<222> LOCATION: (26)...(241)
<223> OTHER INFORMATION: CLONE: alpha-hemoglobin
      linear cDNA to mRNA
<220> FEATURE:
<221> NAME/KEY: CDS
<222> LOCATION: (245)...(670)

<400> SEQUENCE: 7
ctcgagggga tctgatcttt caagaatggc acaaattaac aacatggcac aagggataca      60
aacccttaat cccaattcca atttccataa accccaagtt cctaaatctt caagttttct    120 tgttttgga tctaaaaaac tgaaaaattc agcaaattct atgttggttt tgaaaaaaga    180 ttcaatttt atgcaaaagt tttgttcctt taggatttca gcaggtggta gagtttcttg    240 catg gtg ctg tct cct gcc gac aag acc aac gtc aag gcc gcc tgg ggc      289
     Val Leu Ser Pro Ala Asp Lys Thr Asn Val Lys Ala Ala Trp Gly
     1               5                  10                  15 aag gtt ggc gcg cac gct ggc gag tat ggt gcg gag gcc ctg gag agg        337
Lys Val Gly Ala His Ala Gly Glu Tyr Gly Ala Glu Ala Leu Glu Arg
                20                  25                  30 atg ttc ctg tcc ttc ccc acc acc aag acc tac ttc ccg cac ttc gac        385
Met Phe Leu Ser Phe Pro Thr Thr Lys Thr Tyr Phe Pro His Phe Asp
            35                  40                  45 ctg agc cac ggc tct gcc cag gtt aag ggc cac ggc aag aag gtg gcc        433
Leu Ser His Gly Ser Ala Gln Val Lys Gly His Gly Lys Lys Val Ala
        50                  55                  60 gac gcg ctg acc aac gcc gtg gcg cac gtg gac gac atg ccc aac gcg        481
Asp Ala Leu Thr Asn Ala Val Ala His Val Asp Asp Met Pro Asn Ala
    65                  70                  75 ctg tcc gcc ctg agc gac ctg cac gcg cac aag ctt cgg gtg gac ccg        529
Leu Ser Ala Leu Ser Asp Leu His Ala His Lys Leu Arg Val Asp Pro
80                  85                  90                  95 gtc aac ttc aag ctc cta agc cac tgc ctg ctg gtg acc ctg gcc gcc        577
Val Asn Phe Lys Leu Leu Ser His Cys Leu Leu Val Thr Leu Ala Ala
                100                 105                 110 cac ctc ccc gcc gag ttc acc cct gcg gtg cac gcc tcc ctg gac aag        625
His Leu Pro Ala Glu Phe Thr Pro Ala Val His Ala Ser Leu Asp Lys
            115                 120                 125 ttc ctg gct tct gtg agc acc gtg ctg acc tcc aaa tac cgt taa            670
Phe Leu Ala Ser Val Ser Thr Val Leu Thr Ser Lys Tyr Arg *
        130                 135                 140 gctggagcct cggtagccgt tcctcctgcc cggtcgacc                              709

<210> SEQ ID NO 8
<211> LENGTH: 141
<212> TYPE: PRT
<213> ORGANISM: Homo sapiens

<400> SEQUENCE: 8

Val Leu Ser Pro Ala Asp Lys Thr Asn Val Lys Ala Ala Trp Gly Lys
1               5                  10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
```

```
                 50                  55                  60
Ala Leu Thr Asn Ala Val His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 9
<211> LENGTH: 743
<212> TYPE: DNA
<213> ORGANISM: Homo sapiens
<220> FEATURE:
<221> NAME/KEY: transit_peptide
<222> LOCATION: (26)...(241)
<223> OTHER INFORMATION: CLONE: beta-hemoglobin
      linear cDNA to mRNA
<220> FEATURE:
<221> NAME/KEY: CDS
<222> LOCATION: (245)...(685)

<400> SEQUENCE: 9
ctcgagggga tctgatcttt caagaatggc acaaattaac aacatggcac aagggataca      60 aaccctttaat cccaattcca atttccataa accccaagtt cctaaatctt caagttttct    120 tgttttttgga tctaaaaaac tgaaaaattc agcaaattct atgttggttt tgaaaaaaga    180
ttcaattttt atgcaaaagt tttgttcctt taggatttca gcaggtggta gagtttcttg    240 catg gtg cac ctg act cct gag gag aag tct gcc gtt act gcc ctg tgg      289
     Val His Leu Thr Pro Glu Glu Lys Ser Ala Val Thr Ala Leu Trp
      1               5                  10                  15 ggc aag gtg aac gtg gat gaa gtt ggt ggt gag gcc ctg ggc agg ctg      337
Gly Lys Val Asn Val Asp Glu Val Gly Gly Glu Ala Leu Gly Arg Leu
                 20                  25                  30 ctg gtg gtc tac cct tgg acc cag agg ttc ttt gag tcc ttt ggg gat      385
Leu Val Val Tyr Pro Trp Thr Gln Arg Phe Phe Glu Ser Phe Gly Asp
             35                  40                  45 ctg tcc act cct gat gct gtt atg ggc aac cct aag gtg aag gct cat      433
Leu Ser Thr Pro Asp Ala Val Met Gly Asn Pro Lys Val Lys Ala His
         50                  55                  60 ggc aag aaa gtg ctc ggt gcc ttt agt gat ggc ctg gct cac ctg gac      481
Gly Lys Lys Val Leu Gly Ala Phe Ser Asp Gly Leu Ala His Leu Asp
 65                  70                  75 aac ctc aag ggc acc ttt gcc aca ctg agt gag ctg cac tgt gac aag      529
Asn Leu Lys Gly Thr Phe Ala Thr Leu Ser Glu Leu His Cys Asp Lys
 80                  85                  90                  95 ctg cac gtg gat cct gag agc ttc agg ctc cta ggc aac gtg ctg gtc      577
Leu His Val Asp Pro Glu Ser Phe Arg Leu Leu Gly Asn Val Leu Val
                100                 105                 110 tgt gtg ctg gcg cat cac ttt ggc aaa gaa ttc acc cca cca gtg cag      625
Cys Val Leu Ala His His Phe Gly Lys Glu Phe Thr Pro Pro Val Gln
            115                 120                 125 gct gcc tat cag aaa gtg gtg gct ggt gtg gct aat gcc ctg gcc cac      673
Ala Ala Tyr Gln Lys Val Val Ala Gly Val Ala Asn Ala Leu Ala His
        130                 135                 140 aag tat cac taa gctcgctttc ttgctgtcca atttctatta aaggttcctt          725
Lys Tyr His *
```

-continued

145 gtggggtcg aggtcgac                                                  743

<210> SEQ ID NO 10
<211> LENGTH: 146
<212> TYPE: PRT
<213> ORGANISM: Homo sapiens

<400> SEQUENCE: 10

Val His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Ser Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 11
<211> LENGTH: 16
<212> TYPE: PRT
<213> ORGANISM: alkalophilic Bacillus sp
<220> FEATURE:
<221> NAME/KEY: NON_TER
<222> LOCATION: (0)...(0)
<223> OTHER INFORMATION: CLONE: beta-cyclodextrin
      Strain: 38-2

<400> SEQUENCE: 11

Ala Pro Asp Thr Ser Val Ser Asn Lys Gln Asn Phe Ser Thr Asp Val
 1               5                  10                  15

<210> SEQ ID NO 12
<211> LENGTH: 47
<212> TYPE: DNA
<213> ORGANISM: Artificial Sequence
<220> FEATURE:
<223> OTHER INFORMATION: Primer

<400> SEQUENCE: 12
gggctcgaga tttaggtgac actatagtat ttttacaaca attacca              47

<210> SEQ ID NO 13
<211> LENGTH: 13
<212> TYPE: DNA
<213> ORGANISM: Tobamovirus
<220> FEATURE:
<221> NAME/KEY: 5'clip
<222> LOCATION: (0)...(0)
<223> OTHER INFORMATION: At 5" end

```
<400> SEQUENCE: 13
ctcgaggatg atc                                                    13

<210> SEQ ID NO 14
<211> LENGTH: 12
<212> TYPE: DNA
<213> ORGANISM: alpha-trichosanthin

<400> SEQUENCE: 14
tcgaggatga tc                                                     12

<210> SEQ ID NO 15
<211> LENGTH: 108
<212> TYPE: DNA
<213> ORGANISM: Artificial Sequence
<220> FEATURE:
<221> NAME/KEY: CDS
<222> LOCATION: (19)...(108)
<223> OTHER INFORMATION: Tobamovirus

<400> SEQUENCE: 15
gttttaaata cgctcgag gat gat cag att ctt agt cct ctc ttt gct aat      51
                    Asp Asp Gln Ile Leu Ser Pro Leu Phe Ala Asn
                     1               5                  10 tct cac ctc ttc cta aca act cct gct gtg gag ggc gat gtt agc ttc     99
Ser His Leu Phe Leu Thr Thr Pro Ala Val Glu Gly Asp Val Ser Phe
         15                  20                  25 cgt tta tca                                                        108
Arg Leu Ser
         30

<210> SEQ ID NO 16
<211> LENGTH: 30
<212> TYPE: PRT
<213> ORGANISM: Tobamovirus

<400> SEQUENCE: 16

Asp Asp Gln Ile Leu Ser Pro Leu Phe Ala Asn Ser His Leu Phe Leu
 1               5                  10                  15

Thr Thr Pro Ala Val Glu Gly Asp Val Ser Phe Arg Leu Ser
             20                  25                  30

<210> SEQ ID NO 17
<211> LENGTH: 15
<212> TYPE: DNA
<213> ORGANISM: Tobamovirus
<220> FEATURE:
<221> NAME/KEY: 3'clip
<222> LOCATION: (0)...(0)
<223> OTHER INFORMATION: At 3' end

<400> SEQUENCE: 17
atttagtaac tcgag                                                   15

<210> SEQ ID NO 18
<211> LENGTH: 12
<212> TYPE: DNA
<213> ORGANISM: Tobacco mosaic virua

<400> SEQUENCE: 18
ttaaatatgt ct                                                      12

<210> SEQ ID NO 19
```

-continued

```
<211> LENGTH: 12
<212> TYPE: DNA
<213> ORGANISM: ORSV

<400> SEQUENCE: 19
tgaaatatgt ct                                                        12
```